(12) United States Patent
Okhamafe et al.

(10) Patent No.: US 8,614,216 B2
(45) Date of Patent: Dec. 24, 2013

(54) CRYSTALLINE AND OTHER FORMS OF 4-AMINO-5-FLUORO-3-[6-(4-METHYL-PIPERAZIN-1-YL)-1H-BENZIMIDAZOL-2-YL]-1H-QUINOLIN-2-ONE LACTIC ACID SALTS

(75) Inventors: Augustus O Okhamafe, Concord, CA (US); Joyce Chou, El Cerrito, CA (US); Rampurna Gullapalli, San Bruno, CA (US); Eric Harwood, Seattle, WA (US); David Ryckman, San Diego, CA (US); Shuguang Zhu, San Diego, CA (US); Xiao Shang, Bellevue, WA (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 13/457,867

(22) Filed: Apr. 27, 2012

(65) Prior Publication Data

US 2012/0208825 A1 Aug. 16, 2012

Related U.S. Application Data

(63) Continuation of application No. 11/915,005, filed as application No. PCT/US2006/020296 on May 23, 2006, now abandoned.

(60) Provisional application No. 60/683,999, filed on May 23, 2005.

(51) Int. Cl.
*A61K 31/497* (2006.01)
*A01N 43/82* (2006.01)
*A61K 31/41* (2006.01)

(52) U.S. Cl.
USPC ..................... 514/253.07; 544/363

(58) Field of Classification Search
None
See application file for complete search history.

(56) References Cited

U.S. PATENT DOCUMENTS

| | | |
|---|---|---|
| 3,663,606 A | 5/1972 | Yoshikazu |
| 4,659,657 A | 4/1987 | Harnisch et al. |
| 4,882,342 A | 11/1989 | Von Der Saal et al. |
| 5,073,492 A | 12/1991 | Chen et al. |
| 5,151,360 A | 9/1992 | Handa et al. |
| 5,330,992 A | 7/1994 | Eissenstat et al. |
| 5,414,088 A | 5/1995 | Von Der Saal et al. |
| 5,480,883 A | 1/1996 | Spada et al. |
| 5,585,380 A | 12/1996 | Bianco et al. |
| 5,646,153 A | 7/1997 | Spada et al. |
| 5,710,158 A | 1/1998 | Myers et al. |
| 5,763,441 A | 6/1998 | App et al. |
| 5,792,771 A | 8/1998 | App et al. |
| 5,801,212 A | 9/1998 | Okamoto et al. |
| 5,855,866 A | 1/1999 | Thorpe et al. |
| RE36,256 E | 7/1999 | Spada et al. |
| 5,942,385 A | 8/1999 | Hirth |
| 5,981,569 A | 11/1999 | App et al. |
| 6,057,320 A | 5/2000 | Spada et al. |
| 6,111,110 A | 8/2000 | Brennan et al. |
| 6,137,010 A | 10/2000 | Joo et al. |
| 6,174,912 B1 | 1/2001 | Beck et al. |
| 6,258,951 B1 | 7/2001 | Lohmann et al. |
| 6,268,391 B1 | 7/2001 | Dickerson et al. |
| 6,303,600 B1 | 10/2001 | Cox et al. |
| 6,306,874 B1 | 10/2001 | Fraley et al. |
| 6,313,138 B1 | 11/2001 | Fraley et al. |
| RE37,650 E | 4/2002 | Myers et al. |
| 6,420,382 B2 | 7/2002 | Fraley et al. |
| 6,479,512 B1 | 11/2002 | Fraley et al. |
| 6,593,344 B1 | 7/2003 | Biedermann et al. |
| 6,605,617 B2 | 8/2003 | Renhowe et al. |
| 6,756,383 B2 | 6/2004 | Renhowe et al. |
| 6,759,417 B2 | 7/2004 | Renhowe et al. |
| 6,762,194 B2 | 7/2004 | Renhowe et al. |
| 6,774,237 B2 | 8/2004 | Renhowe et al. |
| 6,774,327 B1 | 8/2004 | Wong |
| 6,800,760 B2 | 10/2004 | Renhowe et al. |
| 7,064,215 B2 | 6/2006 | Renhowe et al. |
| 7,179,912 B2 | 2/2007 | Halbrook et al. |
| 7,470,709 B2 | 12/2008 | Barsanti et al. |
| 7,495,104 B2 | 2/2009 | Miwa et al. |
| 7,825,132 B2 | 11/2010 | Cai et al. ........................ 514/314 |
| 7,838,527 B2 | 11/2010 | Hannah et al. ............ 514/255.02 |
| 2002/0103230 A1 | 8/2002 | Renhowe et al. |

(Continued)

FOREIGN PATENT DOCUMENTS

| | | |
|---|---|---|
| DE | 2363459 | 6/1975 |
| DE | 3634066 | 4/1988 |
| DE | 19841985 | 3/2000 |
| EP | 0 290 153 | 11/1988 |
| EP | 0 508 800 | 10/1992 |

(Continued)

OTHER PUBLICATIONS

Remington: The Science and Practice of Pharmacy, Chapter 34, Section X-ray Powder Diffraction (XRPD), 21st Edition, (2005) p. 659.*

Gullory, Generation of Polymorphs, Hydrates, Solvates and Amorphous Solids in Polymorphism in Pharmaceutical Solids 183-220 (HG Brittain ed., 1999).

(Continued)

*Primary Examiner* — James D Anderson
*Assistant Examiner* — William Lee
(74) *Attorney, Agent, or Firm* — Gregory Ferraro

(57) ABSTRACT

The present invention relates to non-hydrate crystalline forms of 4-amino-5-fluoro-3-[6-(4-methylpiperazin-1-yl)-1H-benzimidazol-2-yl]-1H-quinolin-2-one lactic acid salts, solid pharmaceutical formulations containing the same and methods of use. The present invention also relates to crystalline hydrates of 4-amino-5-fluoro-3-[6-(4-methylpiperazin-1-yl)-1H-benzimidazol-2-yl]-1H-quinolin-2-one lactic acid salts, pharmaceutical formulations containing the same and methods of use related thereto. The present invention further relates to crystalline solvates of 4-amino-5-fluoro-3-[6-(4-methylpiperazin-1-yl)-1H-benzimidazol-2-yl]-1H-quinolin-2-one lactic acid salts.

27 Claims, 13 Drawing Sheets

(56) References Cited

U.S. PATENT DOCUMENTS

| | | |
|---|---|---|
| 2002/0107392 A1 | 8/2002 | Renhowe et al. |
| 2002/0165218 A1 | 11/2002 | Halbrook et al. |
| 2003/0028018 A1 | 2/2003 | Renhowe et al. |
| 2003/0087854 A1 | 5/2003 | Monia et al. |
| 2003/0158224 A1 | 8/2003 | Renhowe et al. |
| 2003/0159702 A1 | 8/2003 | Lindell et al. |
| 2003/0207883 A1 | 11/2003 | Renhowe et al. |
| 2004/0002518 A1 | 1/2004 | Renhowe et al. |
| 2004/0006101 A1 | 1/2004 | Renhowe et al. |
| 2004/0092535 A1 | 5/2004 | Barsanti et al. |
| 2004/0097545 A1 | 5/2004 | Renhowe et al. |
| 2004/0220196 A1 | 11/2004 | Hannah et al. |
| 2005/0054672 A1 | 3/2005 | Renhowe et al. |
| 2005/0137399 A1 | 6/2005 | Cai et al. |
| 2005/0203101 A1 | 9/2005 | Barsanti et al. |
| 2005/0209247 A1 | 9/2005 | Cai et al. |
| 2005/0256157 A1 | 11/2005 | Gesner et al. |
| 2005/0261307 A1 | 11/2005 | Cai et al. |
| 2006/0261307 A1 | 11/2006 | Black et al. |

FOREIGN PATENT DOCUMENTS

| | | |
|---|---|---|
| EP | 0 509 717 | 10/1992 |
| EP | 0 747 771 | 12/1996 |
| EP | 0 797 376 | 9/1997 |
| EP | 1 086 705 | 5/1999 |
| HU | P0104752 | 7/2002 |
| JP | 59-130284 | 7/1984 |
| JP | 63230687 | 9/1988 |
| JP | 63-258903 | 10/1988 |
| JP | 6-9952 | 1/1994 |
| JP | 7-43896 | 2/1995 |
| JP | 8-29973 | 2/1996 |
| JP | 2003171280 | 6/2003 |
| WO | WO 91/04974 | 4/1991 |
| WO | WO 92/18483 | 10/1992 |
| WO | WO 92/20642 | 11/1992 |
| WO | WO 95/15758 | 6/1995 |
| WO | WO 95/18801 | 7/1995 |
| WO | WO 97/03069 | 1/1997 |
| WO | WO 97/34876 | 9/1997 |
| WO | WO 97/48894 | 12/1997 |
| WO | WO 98/13350 | 4/1998 |
| WO | WO 00/00481 | 6/1998 |
| WO | WO 00/11709 | 8/1998 |
| WO | WO 99/10349 | 8/1998 |
| WO | WO 98/55124 | 12/1998 |
| WO | WO 99/16755 | 4/1999 |
| WO | WO 99/48868 | 9/1999 |
| WO | WO 99/50263 | 10/1999 |
| WO | WO 00/27379 | 11/1999 |
| WO | WO 99/65897 | 12/1999 |
| WO | WO 00/03990 | 1/2000 |
| WO | WO 00/20400 | 4/2000 |
| WO | WO 01/02369 | 6/2000 |
| WO | WO 00/58315 | 10/2000 |
| WO | WO 01/29025 | 10/2000 |
| WO | WO 00/71129 | 11/2000 |
| WO | WO 00/74683 | 12/2000 |
| WO | WO 01/52875 | 1/2001 |
| WO | WO 01/52904 | 1/2001 |
| WO | WO 01/53268 | 1/2001 |
| WO | WO 01/55114 | 1/2001 |
| WO | WO 01/12169 | 2/2001 |
| WO | WO 01/60814 | 2/2001 |
| WO | WO 01/74296 | 3/2001 |
| WO | WO 01/28993 | 4/2001 |
| WO | WO 01/62251 | 8/2001 |
| WO | WO 01/62252 | 8/2001 |
| WO | WO 02/26716 | 9/2001 |
| WO | WO 02/18383 | 3/2002 |
| WO | WO 02/22598 | 3/2002 |
| WO | WO 02/32861 | 4/2002 |
| WO | WO 02/058697 | 8/2002 |
| WO | WO 03/004488 | 1/2003 |
| WO | WO 03/033472 | 4/2003 |
| WO | WO 03/087095 | 10/2003 |
| WO | WO 2004/018419 | 3/2004 |
| WO | WO 2004/030620 | 4/2004 |
| WO | WO 2004/031401 | 4/2004 |
| WO | WO2004043389 | 5/2004 |
| WO | WO 2004/063151 | 7/2004 |
| WO | WO 2004/063170 | 7/2004 |
| WO | WO 2004/087153 | 10/2004 |
| WO | WO 2005/009967 | 2/2005 |
| WO | WO 2005/046589 | 5/2005 |
| WO | WO 2005/047244 | 5/2005 |
| WO | WO2005046590 | 5/2005 |
| WO | WO 2005/053692 | 6/2005 |
| WO | WO2005082340 | 9/2005 |
| WO | WO2006081445 | 8/2006 |
| WO | WO 2006/127926 | 11/2006 |

OTHER PUBLICATIONS

Morrisette et al., Advanced Drug Delivery Reviews, 56, 275-300 (2004).
Caira, Mino R., "Crystalline polymorphism of Organic Compounds"; Topcs in Current Chemistry, vol. 198, Springer Verlag 1998.
Extended European Search Report for EP Appln. No. 10178683.8 completed Nov. 10, 2010.
Extended European Search Report for EP Appln. No. 10178789.3 completed Nov. 10, 2010.
Brittain H.G.(editor), et al., "Polymorphism in pharmaceutical solids," Publihsed by Informa Healthcare; Grant (chapter 1); pp. 1-31 and J.K. Guillory (chapter 5); pp. 183-226, Mar. 3, 1999.
Jain et al., "Polymorphism in Pharmacy," Indian Drugs, 1986, 23(6), 315-329.
Vippagunta et al, Crystalline Solids, Advance Drug Delivery Reviews (2001), 48:3-26.
Andre, T., et al., "CPT-11 (Irinotecan) Addition to Bimonthly, High-dose Leucovorin and Bolus and Continuous-infusion 5-Fluorouracil (FOLFIRI) for Pretreated Metastic Colorectal Cancer," European Journal of Cancer, vol. 35, No. 9, 1999, pp. 1343-1347. Compound Summary also attached.
Magne, N., et al., "Sequence-dependent effects of ZD 1839 (Iressa) in combination with cytotoxic treatment in human head and neck cancer," British Journal of Cancer, 2002, pp. 819-827.
Noble, et al., "Protein Kinase Inhibitors: Insights into Drug Design from Structure," Science, vol. 303, Mar. 19, 2004, pp. 1800-1805.
Antonios-McCrea, W. R. et al., "LHMDS mediated tandem acylation-cyclization of 2-aminobenzenecarbonitriles with 2-benzymidazol-2-yl acetates: a short and efficient route to the synthesis of 4-amino-3-benzimidazol-2-ylhydroquinolin-2-ones," Tetrahedron Letters, vol. 47, 2006, pp. 657-660; published by Elsevier Ltd.
Berge, et al., "Pharmaceuticals Salts," J. Pharm. Sci., vol. 66, No. 1, pp. 1-19, 1977.
CAS printout for 300591-52-0 Registry File, entry date into Registry File Oct. 31, 2000.
CAS printout for 304876-79-7 Registry File, entry date into Registry File Nov. 29, 2000.
Charvat, T. et al., "Diethyl Acetonedicarboxylate—a Precursor for the Synthesis of New Substituted 4-Aminoquinolines and Fused 4-Aminopyridines," Monatshefte für Chemie, vol. 126, 1995, pp. 333-340.
Lopes de Menezes, D. E. et al., "CHIR-258: A Potent Inhibitor of FLT3 Kinase in Experimental Tumor Xenograft Models of Human Acute Myelogenous Leukemia," Clin. Cancer Res., Jul. 15, 2005, vol. 11, No. 14, pp. 5281-5291.
Trudel, S. et al., "CHIR-258, a novel, multitargeted tyrosine kinase inhibitor for the potential treatment of t(4;14) multiple myeloma," Blood, Apr. 1, 2005, vol. 105, No. 7, pp. 2941-2948.
Ukrainets, I., "Effective Synthesis of 3-(Benzimidazol-2-yl)-4-Hydroxy-2-Oxo-1,2-Dihydroquinolines." Tet. Lett., vol. 36, No. 42, pp. 7747-7748, 1995, published by Elsevier Science Ltd., Great Britain.

(56) References Cited

OTHER PUBLICATIONS

Ukrainets, I., et al., "2-Carbethoxymethyl-4H-3,1-Benzoxazin-4-One. 3. Condensation of o-Phenylenediamine," pp. 198-200, translated from *Khimiya Gerotsiklicheskikh Soedinii*, No. 2, pp. 239-241, Feb. 1992, published by Plenum Publ. Corp., London, Great Britain.
Ukrainets, I., et al., "4-Hydroxy-2-Quinolones 7. Synthesis and Biological Properties of 1-R-3-(2-Benzimidazolyl)4-Hydroxy-2-Quinolones," pp. 92-94, translated for *Khimiya Geterotsiklicheskikh Soedinii*, No. 1, pp. 105-108, Jan. 1993, published by Plenum Publ. Corp., London, Great Britain.
Ukrainets, I., et al., "4-Hydroxy-2-Quinolones. 16. Condensation of N-R-Substituted Amides of 2-Carboxy-Malonanilic Acid With o-Phenylenediamine," pp. 941-944, translated from *Khimiya Geterotsiklicheskikh Soedinii*, vol. 8, pp. 1105-1108, Aug. 1993, published by Plenum Publ. Corp., London, Great Britain.
Ukrainets, I., et al., "4-Hydroxy-2-Quinolones. 32. Synthesis and Antithyroid Activity of Thio Analogs of 1H-2-OXO-3-(2-Benzimidazolyl)-4-HydroxyQuinoline," *Chem. Heterocyclic Comp.*, vol. 33, No. 5, pp. 692-696, 1997, published by Kluwer Academic Publishers, London, Great Britain.
Veronese, A. C. et al., "Tin (IV) Chloride-promoted Synthesis of 4-Aminopyridines and 4-Aminoquinolines," *Tetrahedron*, vol. 51, No. 45, 1995, pp. 12277-12284; published by Elsevier Science Ltd.
Zhao, H. et al., "ATR-Mediated Checkpoint Pathways Regulate Phosphorylation and Activation of Human Chk1." *Molecular and Cellular Biology*, vol. 21, No. 13, pp. 4129-4139, Jul. 2001; published by American Society for Microbiology.
Aprelikova, O., et al ; Cancer Res., vol. 52, pp. 746-748, Feb. 1, 1992, published by the American Association for Cancer Research, Stanfors University Libraries, High Wire Press, California, USA.
Bastin, et al ; Organic Process Research & Development, vol. 4, pp. 427-435, 2000.
Beals, C.R. et al ; Science , vol. 275, pp. 1930-1933, Mar. 28, 1997.
Brewanger, B. et al ; Cancer Cell, vol. 2, Nov. 2002, pp. 377-386; published by Cell Press.
Brownlees, J., et al ; NeuroReportm vol. 8, No. 15, pp. 3251-3255, Oct. 20, 1997; published by Rapid Science.
Carla Heise, et al ; Abstract and presentation matrial for presentation at the American Assocation for Cancer Research meeting held in Apr. 2002.
Carmeliet, P. et al ; Nature, 407, pp. 249-257 (2000).
Cecil, Textbox of Medicine, 21st Edition (2000). Goldman & Bennett (Editors), W.B. Saunders Company(Publisher), Chapter 198, pp. 1060-1074.
Chan. T.A. et al ; Nature, vol. 401, pp. 616-620, Oct. 7, 1999; published by Macmillan Magazines Ltd.
Chen, G. et al ; J. Neurochem, vol. 72, No. 3, 1999, pp. 1327-1330: published by Lippincott Williams & Wilkins Inc. Philadelphia.
Chasi, M. et al ; Blood, vol. 97, No. 3, pp. 729-736, 1published by the American Society f Hematology, (2001).
Connoly, D., et al ; J.Biol.Chem., vol. 264, pp. 20017-20024, 1989, published by The American Society For Biochemistry and Molecular Biology, Inc., Stanford University Libraries High Wire Press, California.
Connoly, D., et al ; J.Clin.Invest., vol. 84, pp. 1470-1478, Nov. 1989, published by The American Society for Clinical Investogation., Stanford University Libraries High Wire Press, California, USA.
Cross, A., et al ; Biochem J., vol. 303, pp. 21-26, 1994; (printed in Great Britain).
Dalton, et al ; Hematology, Am.Soc.Hematol.Educ.Program, 2001, 157-77.
Dankbar, B., et al ; Blood, 2000, vol. 5(8), pp. 2630-2636.
Dermer, G.B., Biotechnology, 1994, vol. 12, p. 320.
DeVries, C., et al ; Science, vol. 255, pp. 898-991, Feb. 21, 1992, published by The American Society for the Advanement of Science, Standford University Libraries High Wire Press, California, USA.
Doukas, M.A., et al ; Exp. Hematol., vol. 14, pp. 215-221, 1986. published by International Society for Experimental Hematology.
European Search Report dated Feb. 28, 2006, for EP 05017665.0.

Ferrara, N.,K et al; Endocrinol. Rev., vol. 18, No. 1, pp. 4-25, 1997, published by The Endocrine Society, Stanford University Libraries High Wire Press, California, USA.
Fluckiger-Isler, R.E. et al ; Biochem. J., vol. 292, pp. 85-91, 1993; (printed in Great Britain).
Folkman, J., Scientific American, vol. 275, pp. 150-154, Sep. 1996. published by Scientific American, Inc., New York, New York, USA.
Gontero, et al; European Urology, vol. 46, pp. 298-311, (2004).
Grand, et al ; Leukemia, 2004, vol. 18, pp. 962-966.
Gruber., G, et al; Blood, 1999, vol. 94(3), pp. 1077-1085.
Gura, T., Science, 1997, vol. 278, pp. 1041-1042.
Hammond, W.P. et al; Blood, vol. 55, No. 1, pp. 26-28, Jan. 1980.
Heinrich, M.C. et al; J.Clin. Oncol., vol. 20, No. 6, pp. 1692-1703, Mar. 15, 2002.
Hennequin, L.F., et al ; J.Med.Chem., vol. 42, No. 26, pp. 5369-5389, 1999; published by American Chemical Society, Washington, D.C.
Hirao, A. et al ; Science, vol. 287, pp. 1824-1827, Mar. 10, 2000.
Hussong, J.W. et al , Blood, 2000, vol. 95(1). pp. 309-313; The American Society of Hematology.
International Search Report for PCT/US04/36956 dated Oct. 2, 2006.
International Search Report for PCT/US/2005/005316 dated Nov. 28, 2005.
Karbel, R.S., Carcinogenesis, 2000, vol. 21(3), pp. 505-515; Oxford University Press.
Kirstein, CA 145:201781, abstract only of Recent Patents on Anti-cancer Drug Discovery, vol. 1(2), pp. 153-161 (2006).
Klein, P.S. et al; Proc.Natl.Acad.Sci.USA vol. 93, pp. 8455-8459, Aug. 1996.
Lee, J. et al ; Molecular Biology of the Cell, vol. 12, pp. 551-556, Mar. 2001; published by the American Society for Cell Biology.
Lee, S.H. et al ; Clin. Cancer Res., May 15, 2005, vol. 11, No. 10; pp. 3633-3641.
Leung, D., et al ; Science, vol. 246, pp. 1306-1309. Dec. 8, 1989, published by The American Society for the Advancement of Science, Stanford University Libraries High Wire Press, California, USA.
Levies, M. et al ; Blood, vol. 99, No. 11, pp. 3885-3891, Jun. 1, 2002; published by the American Society of Hematology.
Liu Q. et al ; Genes & Development, vol. 14, 2000, pp. 1448-1459, published by Cold Springs Harbor Labratory Press.
Lopez-Girona, A. et al; Nature, vol. 397, pp. 172-175, Jan. 14, 1999 ; published by Macmillan Magazines Ltd.
Lovestone, S. et al; Current Biology, vol. 4, pp. 1077-1086, Dec. 1, 1994; published by Elsevier Science Ltd.
Lundberg, L.G. et al; American Journal of Pathology, 2000, vol. 157(1), pp. 15-19.
Lymboussaki, A., Academic Dissertation, University of Helsinki, Molecular/Cancer Biology Labratory and Department of Pathology, Haartman Institute, 1999.
Maguire, M.P., et al; J.Med.Chem., vol. 37, No. 14, pp. 2129-2137, 1994: published by American Chemical Society, Washington, D.C.
Majolini, M.B. et al ; Leukemia and Lymphoma, vol. 35 (3-4), 1999, pp. 245-254 ; published by OPA (Overseas Publishers Assocation), N.V.
Massilon, D. et al; Biochem. J., vol. 299, pp. 123-128, 1994; printed in Great Britain.
Matel, S., et al; Rev.Chim., vol. 33, No. 6, pp. 527-530, 1989, published by the Central Institute of Chemistry, Bucharest, Romania.
McMahon, G., The Oncologist 2000, vol. 5 (suppl.), pp. 3-10 (2000).
Menzel, T. et al ; Blood, 996, vol. 87(3), pp. 1056-1063, (1996).
Milaure, B. et al ; Nature, vol. 367, pp. 576-579 (1994); published by Nature Publishing Group.
MSNBC News Services. "Mixed results on new cancer drug," Nov. 9, 2000.
Mustoen, T., et al ; J. Cell Biology, vol. 129, No. 4, pp. 895-898, May 1999, published by The Rockfeller University Press, New York, New York, USA.
Nonaka, S. et al ; Proc.Natl.Acad.Sci. USA, vol. 95, pp. 2642-2647, Mar. 1998.
Parker, L.L. et al ; Science, vol. 257, pp. 1955-1957, Sep. 25, 1992.
Pei, J-J. et al ; Journal of Neuropathology and Experimental Neurology, vol. 56, No. 1, pp. 70-78, Jan. 1997, published by the American of Neuropathologists.
Peng, G-Y. et al ; Sciencem vol. 277, pp. 1501-1505, Sep. 5, 1997.

(56) References Cited

OTHER PUBLICATIONS

Pindeo, H.M. et al; The Oncologist 2000, vol. 5 (suppl. 1). pp. 1-2 (2000).
Ploute, J., et al ; EMBO J., vol. 8, No. 12, pp. 3801-3806, 1989, published by the IRL Press.
Quinn, T., et al ; Proc.Natl.Acad.Sci.USA, vol. 90, pp. 7533-7537, Aug. 1993.
Saito, Y. et al ; Biochem, J., vol. 303, pp. 27-31, 1994; printed in Great Britain.
Salmon, S.E., et al ; Basic & Clonical Pharmacology, Seventh Edition , edited by B. Ketzung, Appleton & Lange, pp. 29, 881-884 (1998).
Sanchez, Y. et al ; Science, vol. 277, p. 1497-1501. Sep. 5, 1997.
Shibuya, M., et al ; Oncoene, vol. 5, pp. 519-524, 1990, published by Macmillan Press Ltd., Stockton Press Company, Great Britain.
Simeister, G. et al ; Cancer Research , vol. 59, Jul. 1, 1999, pp. 3185-3191.
Smolich, B.D. et al ; Blood, vol. 97, No. 5, pp. 1413-1421, Mar. 1, 2001; published by The American Society of Hematology.
Stambolic, V. et al ; Current Biology m vol. 6, No. 12, pp. 1664-1668, 1996; published by Current Biology Ltd. ISSN 0960-9822.
Stover, D.R., Current Opinion in Drug Discovery & Development, vol. 2, No. 4, pp. 274-285, 1999; published by PharmaPress Lrd., London , United Kingdom.
Sun, T-Q. et al ; Nature Cell Biology, vol. 3, pp. 628-636, Jul. 2001; published by Macmillan Magazines Ltd.
Susa, M. et al ; TIPS, vol. 21, Dec. 2000, pp. 489-495; published by Elsevier Science Ltd.
Takashima, A. et al ; Proc.Natl.Acad.Sci. USA, vol. 95, pp. 9637-9641, Aug. 1998; published by The National Academy of Sciences.
Takasahima, A. et al ; Proc.Natl.Acad.Sci.USA, vol. 90, pp. 7789-7793, Aug. 1993.
Terman, B., et al ; Oncogene, vol. 6, pp. 1677-1683, published by Macmillan Press Ltd., Stockton Press Company. Great Britain, (1991).
Thomas, M.O., R.J. et al ; J. of the American Geriatrics Society, vol. 43, No. 11, Nov. 1995; published by American Genatrics Society.
Ullrich, A., et al ; Cell, vol. 61, pp. 203-212, Apr. 20, 1990, published by Cell Press, Cambridge, Massachusetts, USA.
Valtola, R. et al ; American Journal of Pathology, vol. 154, No. 5, May 1999, pp. 1381-1390; published by American Society for Investigative Pathology.
Van der Geer, P., et al ; Annu.Rev.Cell.Biol., vol. 10, pp. 251-337, 1994; published by Annual Reviews, Inc., Palo Alto, California, USA.
Vogelstein, B. et al ; Nature m vol. 408, pp. 307-310, Nov. 16, 2000, published by Macmillan Magazines Ltd.
Welsh, G.I. et al ; Biochem.J., vol. 294, pp. 625-629, 1993I printed in Great Britain.
Winstead, E., NCI Cancer Bulletin, vol. 4, No. 5, pp. 1-2, 2007.
Yamasaki, Y. et al ; Tohoku J.Exp.Med, vol. 183, pp. 173-183, 1997.
Yao, et al ; Journal of Neuro-Oncology, vol. 76, pp. 219-225, 2006.
Yoo, et al ; Yonsei Medical Journal, vol. 39, No. 1, pp. 27-36, 1998.
Zeng, et al ; The Journal of Cell Biology, vol. 174, No. 7, pp. 1059-1069, 2006.
Zetter, B.R., Annu.Rev.Med., 1998, vol. 49, pp. 407-424; published by Annual Review Inc.
Zhang, Z. et al; Nature, vol. 395, pp. 698-702, Oct. 15, 1998, published by Macmillan Publishers Ltd.
Beck, J.R., J. Org. Chem., vol. 37, No. 21, 1972, pp. 3224-3226.
Beebe, J.S. et al., Cancer Research, vol. 63, pp. 7301-7309, Nov. 2003.
Carling, R. W. et al., J. Med. Chem., vol. 40, 1997, pp. 754-765, published by American Chemical Society.
Cecil, Textbook of Medicine, 21st Edition (2000), Goldman & Bennett (Editors), W.B. Saunders Company (Publisher), Chapter 198, pp. 1060-1074.
Foekens, et al., Cancer Research, 2001, vol. 61, pp. 5407-5414.
Gewald, K. et al., Chem. Ber., vol. 124, 1991, pp. 1237-1241, Eng. Abstract provided; published by VCH Vertagsgeselischaft mbH.
Glade-Bender, J. et al., Expert Opinion on Biological Therapy, vol. 3, No. 2, Apr. 2003, pp. 263-276.
Guideline for the Format and Content of the Human Pharmacokinetic and Bioavailability Section of an Application, Center for Drugs and Biologics, FDA, Department of Health & Human Services, pp. 1-18, Feb. 1997.
Hiyama, T. et al., Tetrahedron Letters, vol. 23, No. 15, 1982, pp. 1597-1600, published by Pergamon Press Ltd.
Jackman, A.L., et al, European Journal of Cancer, vol. 35, Suppl. 1, Mar. 1999, pp. S3-S8.
Johnson et al., British Journal of Cancer, vol. 84, No. 10, 2001, pp. 1424-1431.
Kreimayer, A. et al., J. Med. Chem., vol. 42, 1999, pp. 4394-4404; published by American Chemical Society.
Morin, Michael J., Oncogene, 2000, pp. 6574-6583.
Parham, W. E. et al., J. Org. Chem., vol. 41, No. 7, 1976, pp. 1187-1191.
Schafer, H. et al., Journal f. prakt. Chemie, Band 321, Heft 4, 1979, pp. 695-698, Eng. Abstract included.
Suggitt et al., Clinical Cancer Research, vol. 11, 2005, pp. 971-981.
Veronese, A. C. et al., J. Chem Research (S), 1988, pp. 246-247.
Wedge, S. R. et al., Cancer Research, vol. 82, pp. 4645-4655, Aug. 15, 2002.
Byrn S. et al., "Pharmaceutical Solids. A Strategic Approach to Regulatory Considerations", Pharmaceutical Research, 12(7): 945-954, 1995.
Byrn S. et al., "Solid State Chemistry of Drugs", Second Edition, 1999, chapter 1; pp. 23-25 and chapter 11; pp. 233-247.
Smith, B. D. et al, Blood, 2004, 103:3669-3676.
Mustonen, T. et al, J. Cell Biology 129, 895-898 (1995).
Slamon, D. J. etal, N. Engl. J. Med. 2001; 344:783-792.
Demetri, G. D. et al, N. Engl. J. Med., 2002; 347-472-480.
Druker, B. J. et al., N. Engl. J. Med., 2001;344:1031-1037.
Levis, M. et al., Blood 99, 11; 2002.
Paterson, J. L. et al. Br. J. Haematol. 2004; 124:595-603.
Trudel, S. et al. Blood,2004; 103:3521-3528.
Li, Z. et al. Blood,20 2001; 97:2413-2419.
Pollett, J. B. et al, Blood, 2002;100;3819-3821.
Plowright, E. E. et al, Blood, 2000; 95:992-998.
Chesi, M. et al. Blood, 1998; 92:3025-3034.
Chesi, M. et al, Nat. Genet, 1997, 16:260-265.
Quinn, T. et al, Proc. Natl. Acad. Sci. 90,7533-7537 (1993).
Connolly, D. et al, J. Biol. Chem. 264,20017-20024 (1989).
Chang,H. et al., Br. J. Haematol., 2004; 125:64-66.
Moreau, P. et al. Blood, 2002; 100:1579-1583.
Keats, J. J. etal, Blood, 2003, 101:1520-1529.
Plouet, J. et al, EMBO J 8, 3801-3806 (1989).
Attal, M. et al, N. Engl. J. Med., 1996: 335:91-97.
Barlogie, B. et al. Blood, 1997; 89:789-793.
Kuehi, W. M. et al, Nat RevCancer, 2002:2:175-187.
Avet-Loiseau, H. et al, Blood, 2002, 99:2185-2191.
Fonseca, R. et al. Blood, 2003; 101:4569-4575.
U.S. Appl. No. 10/452,786, filed Jun. 2, 2003.
U.S. Appl. No. 10/613,411, filed Jul. 3, 2003.
U.S. Appl. No. 10/644,055, filed Aug. 19, 2003.
U.S. Appl. No. 10/839,793, filed May 5, 2004.
U.S. Appl. No. 10/982,543, filed Nov. 5, 2004.
U.S. Appl. No. 10/706,328, filed Nov. 12, 2003.
U.S. Appl. No. 10/982,757, filed Nov. 5, 2004.
Angiogenesis Foundation "New study shows that acute myeloid leukemia is angiogenesis-dependent" Jan. 4, 2000, www.angio.org/newsandviews/archive2000/jan42000.html.
List of compounds purchased from various vendors (3 pages) Aug. 17, 1998.

\* cited by examiner

Powder X-ray Diffraction Pattern of Form C

Powder X-ray Diffraction Pattern of Form D

Powder X-ray Diffraction Pattern of Form E

Powder X-ray Diffraction Pattern of 1,4-Dioxane Hemisolvate

Powder X-ray Diffraction Pattern of Benzene Hemisolvate

PXRD of Mesomorphic Form H

PXRD Pattern of Form I

CRYSTALLINE AND OTHER FORMS OF 4-AMINO-5-FLUORO-3-[6-(4-METHYL-PIPERAZIN-1-YL)-1H-BENZIMIDAZOL-2-YL]-1H-QUINOLIN-2-ONE LACTIC ACID SALTS

This application is a continuation of application Ser. No. 11/915,005, which is National Stage of International Application No. PCT/US2006/020296 filed on May 23, 2006, which claims benefit of U.S. provisional Application No. 60/683,999 filed on May 23, 2005, the entire disclosures of which are hereby incorporated by reference.

FIELD OF THE INVENTION

The present invention relates to non-hydrate crystalline forms of 4-amino-5-fluoro-3-[6-(4-methylpiperazin-1-yl)-1H-benzimidazol-2-yl]-1H-quinolin-2-one lactic acid salts, pharmaceutical formulations containing the same and methods of use related thereto. The present invention also relates to crystalline hydrates of 4-amino-5-fluoro-3-[6-(4-methylpiperazin-1-yl)-1H-benzimidazol-2-yl]-1H-quinolin-2-one lactic acid salts, pharmaceutical formulations containing the same and methods of use related thereto. The present invention further relates to crystalline solvates of 4-amino-5-fluoro-3-[6-(4-methylpiperazin-1-yl)-1H-benzimidazol-2-yl]-1H-quinolin-2-one lactic acid salts. The present invention also relates to amorphous and mesomorphic forms of 4-amino-5-fluoro-3-[6-(4-methylpiperazin-1-yl)-1H-benzimidazol-2-yl]-1H-quinolin-2-one lactic acid salts.

BACKGROUND OF THE INVENTION

Capillaries reach into almost all tissues of the human body and supply tissues with oxygen and nutrients as well as removing waste products. Under typical conditions, the endothelial cells lining the capillaries do not divide, and capillaries, therefore, do not normally increase in number or size in a human adult. Under certain normal conditions, however, such as when a tissue is damaged, or during certain parts of the menstrual cycle, the capillaries begin to proliferate rapidly. This process of forming new capillaries from pre-existing blood vessels is known as angiogenesis or neovascularization. See Folkman, J. Scientific American 275, 150-154 (1996). Angiogenesis during wound healing is an example of pathophysiological neovascularization during adult life. During wound healing, the additional capillaries provide a supply of oxygen and nutrients, promote granulation tissue, and aid in waste removal. After termination of the healing process, the capillaries normally regress. Lymboussaki, A. "Vascular Endothelial Growth Factors and their Receptors in Embryos, Adults, and in Tumors" Academic Dissertation, University of Helsinki, Molecular/Cancer Biology Laboratory and Department of Pathology, Haartman Institute, (1999).

Angiogenesis also plays an important role in the growth of cancer cells. It is known that once a nest of cancer cells reaches a certain size, roughly 1 to 2 mm in diameter, the cancer cells must develop a blood supply in order for the tumor to grow larger as diffusion will not be sufficient to supply the cancer cells with enough oxygen and nutrients. Thus, inhibition of angiogenesis is expected to halt the growth of cancer cells.

Receptor tyrosine kinases (RTKs) are transmembrane polypeptides that regulate developmental cell growth and differentiation, remodeling and regeneration of adult tissues. Mustonen, T. et al., J. Cell Biology 129, 895-898 (1995); van der Geer, P. et al. Ann Rev. Cell Biol. 10, 251-337 (1994). Polypeptide ligands known as growth factors or cytokines, are known to activate RTKs. Signaling RTKs involves ligand binding and a shift in conformation in the external domain of the receptor resulting in its dimerization. Lymboussaki, A. "Vascular Endothelial Growth Factors and their Receptors in Embryos, Adults, and in Tumors" Academic Dissertation, University of Helsinki, Molecular/Cancer Biology Laboratory and Department of Pathology, Haartman Institute, (1999); Ullrich, A. et al., Cell 61, 203-212 (1990). Binding of the ligand to the RTK results in receptor trans-phosphorylation at specific tyrosine residues and subsequent activation of the catalytic domains for the phosphorylation of cytoplasmic substrates. Id.

FLT-3 is a receptor tyrosine kinase belonging to the PDGF Receptor family expressed on acute myelogenous leukemia (AML) cells in a majority of patients and can be present in wildtype form or have activating mutations that result in constitutively active kinase function. An internal tandem repeat (ITD) mutation is expressed in about 25% of AML patients and has been associated with poor prognosis in AML patients. Levis, M. et al., Blood 99, 11; 2002.

c-Kit is another receptor tyrosine kinase belonging to the PDGF Receptor family and is normally expressed in hematopoietic progenitor, mast and germ cells. C-kit expression has been implicated in a number of cancers including mast cell leukemia, germ cell tumors, small-cell lung carcinoma, gastrointestinal stromal tumors, acute myelogenous leukemia (AML), neuroblastoma, melanoma, ovarian carcinoma, breast carcinoma. Heinrich, M. C. et al., J. Clin. One. 20, 6 1692-1703, 2002 (review article); Smolich, B. D. et al., Blood, 97, 5; 1413-1421.

c-ABL is a tyrosine kinase that was originally identified as an oncogene product from the genome of the Abelson murine leukemia virus. About 90% of chronic myelogenous leukemia (CML), 20-30% of acute lymphoblastic leukemia (ALL) and about 1% of acute myeloblastic leukemia (AML) have a reciprocal translocation between chromosome 9 and 22. The translocation results in the 'Philadelphia' chromosome and is the reason for the expression of a chimeric BCR/ABL transcript.

FGFR3 is a tyrosine kinase associated with various cancers. Fibroblast growth factor receptor 3 (FGFR3) is a class IV receptor tyrosine kinase. FGFR3 is deregulated due to a t(4,14) translocation in about 15-20% of multiple myeloma patients. This translocation causes the expression of a functional FGFR3 that can respond to FGF1 in e.g., the bone microenvironment. In some cases, activating mutations that make FGFR3 ligand independent have been identified. These activating FGFR3 mutations have been found to cause Ras-like tumor progression and evidence exists that similar signaling pathways are utilized (Chesi, et al., Blood 2001 97 729-736.).

CSF-1 (colony-stimulating factor-1) and its receptor Macrophage CSFR-1 (Fms) are required for macrophage proliferation and differentiation as well as placental development. It is expressed during pregnancy and lactation in the mammary gland. Abnormal expression of CSFR1 has been correlated with advanced stage and poor prognosis in breast cancer patients.

C-Met is a receptor tyrosine kinase that binds HGF (hepatocyte growth factor). C-Met is implicated in tumorigenesis, tumor progression and metastasis of multiple tumors including colon cancer, multiple myeloma, small and non small cell lung cancer and renal cell carcinoma. C-Met has been found mutated, amplified, and overexpressed in multiple cancers.

Two subfamilies of RTKs are specific to the vascular endothelium. These include the vascular endothelial growth factor (VEGF) subfamily and the Tie receptor subfamily. Class V RTKs include VEGFR-1, VEGFR-2, and VEGFR-3. Shibuya, M. et al., Oncogene 5, 519-525 (1990); Terman, B. et al., Oncogene 6, 1677-1683 (1991); Aprelikova, O. et al., Cancer Res. 52, 746-748 (1992).

Members of the VEGF subfamily have been described as being able to induce vascular permeability and endothelial cell proliferation and further identified as a major inducer of angiogenesis and vasculogenesis. Ferrara, N. et al., Endocrinol. Rev. 18, 4-25 (1997). VEGF is known to specifically bind to RTKs including VEGFR-1 and VEGFR-2. DeVries, C. et al., Science 255, 989-991 (1992); Quinn, T. et al., Proc. Natl. Acad. Sci. 90, 7533-7537 (1993). VEGF stimulates the migration and proliferation of endothelial cells and induces angiogenesis both in vitro and in vivo. Connolly, D. et al., J. Biol. Chem. 264, 20017-20024 (1989); Connolly, D. et al., J. Clin. Invest. 84, 1470-1478 (1989); Ferrara, N. et al., Endocrino. Rew. 18, 4-25 (1997); Leung, D. et al., Science 246, 1306-1309 (1989); Plouet, J. et al., EMBO J. 8, 3801-3806 (1989).

Because angiogenesis is known to be critical to the growth of cancer and to be controlled by VEGF and VEGF-RTK, substantial efforts have been undertaken to develop therapeutics that are antagonists of VEGF-RTK to thereby inhibit or retard angiogenesis, and, hopefully, interfere or stop tumor proliferation.

Class III RTKs are characterized by an extracellular region composed of five immunoglobulin-like domains and by a split tyrosine kinase domain. Some of the Class III RTKs which are inhibited by the compounds of Formula I include, but are not limited to, KIT, FMS, FLT3, PDGFRα, and PDGFRβ.

Class IV RTKs contain three immunoglobulin-like domains in their extracellular regions. For example, FGFR is a class IV RTK which is inhibited by the compounds of Formula I.

Examples of Class V RTKs that are inhibited by the compound of Formula I include, but are not limited to, VEGFR-1, VEGFR-2, and VEGFR-3.

As a result of inhibition of various RTKs, other ligand-stimulated cellular functions are blocked, including activation of downstream signaling molecules, cellular proliferation and survival. Agents which act as inhibitors of specific RTKs are useful in the treatment of disseminated disease and leukemia, as well as solid tumors, outside of the agent's antiangiogenic activity. That is, compounds such as those described in WO 01/60814, which have a broad range of activity at different RTKs and PTKs, are antiangiogenic agents as well as antitumor agents.

Multiple myeloma (MM), a disease of malignant B cells, is characterized by the accumulation of clonal plasma cells in the bone marrow (BM) and osteolytic bone lesions. Autologous stem cell transplant (ASCT) and advances in supportive care have had a significant impact on the disease and long-term survival. Attal, M. et al., *N. Engl. J. Med.*, 1996; 335: 91-97; and Barlogie, B. et al., *Blood*, 1997; 89:789-793. However, patients invariably relapse, and MM remains a universal fatal disease. The identification of nonrandom chromosomal translocations in MM has resulted in the development of powerful prognostic tools and the identification of novel molecular targets. Nearly half of patients with MM overexpress a putative oncogene, dysregulated by one of five recurrent immunoglobulin heavy (IgH) translocations: 11q13 (cyclin D1), 6p21 (cyclin D3), 4p16 (FGFR3 and MMSET), 16q23 (c-maf) and 20q11 (mafB). Kuehl, W. M. et al., *Nat Rev Cancer,* 2002; 2:175-187; and Avet-Loiseau, H. et al., *Blood,* 2002; 99:2185-2191. These translocations likely represent an early and possibly seminal event in the development of MM. More recently, it has become clear that these specific IgH translocations impart prognostic significance. Particularly, the t(4; 14) translocation with occurs in approximately 20% of patients appears to confer a particularly poor prognosis for MM, with no apparent therapeutic benefit to ASCT. Fonseca, R. et al., *Blood,* 2003; 101:4569-4575; Keats, J. J. et al., *Blood,* 2003; 101:1520-1529; Moreau, P. et al., *Blood,* 2002; 100:1579-1583; and Chang, H. et al., *Br. J. Haematol.,* 2004; 125:64-68. Clearly, novel treatment approaches are required for these patients.

The t(4; 14) translocation is unusual in that it appears to dysregulate two potential oncogenes, MMSET on der(4) and FGFR3 on der(14). Chesi, M. et al., *Nat. Genet.,* 1997; 16:260-265; and Chesi, M. et al., *Blood,* 1998; 92:3025-3034. Whether dysregulation of either or both of these genes is critical for MM pathogenesis is not known, however several lines of evidence support a role for FGFR3 in tumor initiation and progression. Activation of WT FGFR3, a RTK, promotes proliferation and survival in myeloma cells and is weakly transforming in a hematopoetic mouse model. Plowright, E. E. et al., *Blood,* 2000; 95:992-998; Chesi, M. et al., *Blood,* 2001; 97:729-736; and Pollett, J. B. et al., *Blood,* 2002; 100: 3819-3821. Subsequent acquisition of activating mutations of FGFR3 in some MM are associated with progression to late stage myeloma and are strongly transforming in several experimental models. Chesi, M. et al., *Blood,* 2001; 97:729-736; and Li, Z. et al., *Blood,* 2001; 97:2413-2419. In vitro studies suggest that FGFR3 can impart chemoresistance, an observation supported by clinical data that demonstrate poor responses to conventional chemotherapy and shortened median survival of t(4; 14) MM patients. Fonseca, R. et al., *Blood,* 2003; 101:4569-4575; Keats, J. J. et al., *Blood,* 2003; 101:1520-1529; Moreau, P. et al., *Blood,* 2002; 100:1579-1583; and Chang, H. et al., *Br. J. Haematol.,* 2004; 125:64-68. These findings suggest that ectopic expression of FGFR3 may play a significant, albeit not a singular, role in myeloma oncogenesis thus making this RTK a target for molecular based therapy.

Inhibition of FGFR3 in t(4; 14) MM cell lines induces cytotoxic responses demonstrating that these cells remain dependent on FGFR3 signaling despite the complexity of genetic alterations in these cells derived from end stage patients. Trudel, S. et al., *Blood,* 2004; 103:3521-3528; Paterson, J. L. et al., *Br. J. Haematol.,* 2004; 124:595-603; and Grand, E. K. et al., *Leukemia,* 2004; 18:962-966. These observations are congruent with the results of receptor tyrosine inactivation in a range of human malignancies where clinical successes have been documented and encourage the clinical development of FGFR3 inhibitors for the treatment of these poor-prognosis patients. Druker, B. J. et al., *N Engl. J. Med.,* 2001; 344:1031-1037; Demetri, G. D. et al., *N. Engl. J. Med.,* 2002; 347:472-480; Slamon, D. J. et al., *N. Engl. J. Med.* 2001; 344:783-792; and Smith, B. D. et al., *Blood,* 2004; 103:3669-3676.

In particular, certain quinoline compounds have been shown to be useful as protein kinase inhibitors. An example quinoline inhibitor is 4-amino-5-fluoro-3-[6-(4-methylpiperazin-1-yl)-1H-benzimidazol-2-yl]-1H-quinolin-2-one, as well as tautomers and salts thereof; the structure of which is provided below as Formula I. Use and preparation of this compound and its salts, including the mono-lactic acid salt, are described in U.S. Ser. Nos. 10/982,757, 10/982,543, 10/706,328, and 10/644,055, each of which is incorporated herein by reference in its entirety. Related compounds are the subject of U.S. Pat. Nos. 6,605,617, 6,774,237, and 6,800,760, each of which is incorporated herein by reference in its entirety.

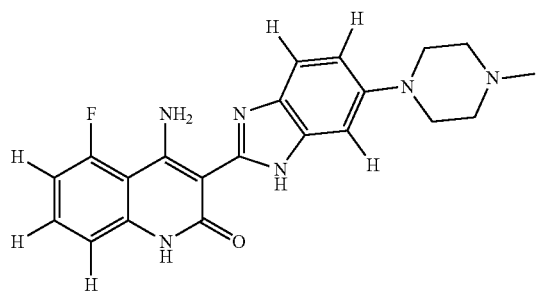

It is well known that the crystalline form of a particular drug is often an important determinant of the drug's ease of preparation, hygroscopicity, stability, solubility, storage stability, ease of formulation, rate of dissolution in the GIT fluids and in vivo bioavailability. Crystalline forms occur where the same composition of matter crystallizes in a different lattice arrangement resulting in different thermodynamic properties and stabilities specific to the particular crystalline form. Crystalline forms may also include different hydrates or solvates of the same compound. In deciding which form is preferable, the numerous properties of the forms are compared and the preferred form chosen based on the many physical property variables. It is entirely possible that one form can be preferable in some circumstances where certain aspects such as ease of preparation, stability, etc are deemed to be critical. In other situations, a different form may be preferred for greater dissolution, rate and/or superior bioavailability.

Because improved drug formulations, showing, for example, better bioavailability or better stability are consistently sought, there is an ongoing need for new or purer polymorphic forms (i.e., crystalline forms) of existing drug molecules. The crystalline forms of 4-amino-5-fluoro-3-[6-(4-methylpiperazin-1-yl)-1H-benzimidazol-2-yl]-1H-quinolin-2-one lactic acid described herein help meet these and other needs.

SUMMARY OF THE INVENTION

The present invention provides a solid formulation of a lactic acid salt of the compound of formula I:

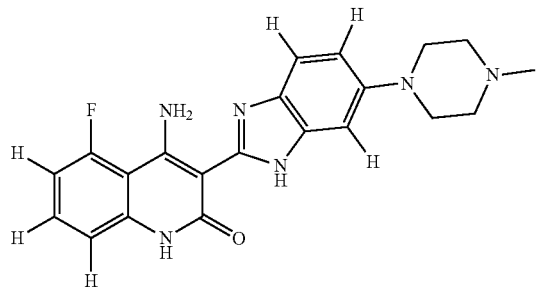

for oral administration, wherein the formulation comprises a non-hydrate crystalline form of a lactic acid salt the compound of formula I.

In some embodiments, the non-hydrate crystalline form is Form A.

In some embodiments, Form A is prepared or is obtainable by stirring the compound of formula I in a solution comprising water, organic solvent and lactic acid.

In some embodiments, the organic solvent is an alcohol.

In some embodiments, the organic solvent is selected from the group consisting of ethanol and isopropanpl.

In some embodiments, the solution comprises about 6.5% water.

In some embodiments, the lactic acid salt of formula I is a mono-lactic acid salt.

In some embodiments, the solid formulation is in powder form.

The present invention further provides methods of treating a patient with a powder formulation of a lactic acid salt of a compound of formula I, comprising orally administering the powder formulation, wherein the powder formulation comprises a non-hydrate crystalline form of a lactic acid salt of compound of formula I.

In some embodiments, the non-hydrate crystalline form is Form A.

In some embodiments, the patient is a cancer patient.

In some embodiments, the patient is diagnosed with multiple myeloma (MM), acute myelogenous leukemia (AML), prostate cancer, breast cancer, colon cancer, or melanoma.

In some embodiments, the patient is a refractory patient.

In some embodiments, the dose comprises 0.25 to 30 mg/kg of the lactic acid salt of the compound of formula I.

In some embodiments, the formulation is prepared or is obtainable in the form of a pill, tablet, capsule, or a caplet.

In some embodiments, the formulation is in solid form at the time of administration.

The present invention further provides a crystalline form (Form A) of a lactic acid salt of the compound of formula I wherein the crystalline form, has an X-ray powder diffraction pattern comprising characteristic peaks, in terms of 2θ, at about 5.7° and about 25.9°.

In some embodiments, the X-ray powder diffraction pattern further comprises a characteristic peak, in terms of 2θ, at about 15.9°.

In some embodiments, the X-ray powder diffraction pattern further comprises a characteristic peak, in terms of 2θ, at about 12.4°.

In some embodiments, the X-ray powder diffraction pattern further comprises a characteristic peak, in terms of 2θ, at about 17.0°.

The present invention further provides a crystalline form (Form A) of a lactic acid salt of the compound of formula I wherein the crystalline form, has an X-ray powder diffraction pattern comprising at least 3 characteristic peaks, in terms of 2θ, selected from at about 5.7, about 11.3, about 12.4, about 15.3, about 15.9, about 17.0, about 19.1, about 19.7, about 20.5, about 20.9, about 22.8, about 23.4, about 23.7, about 24.7, about 25.0, about 25.9, about 26.9, and about 31.2 degrees.

In some embodiments, the crystalline form has an X-ray powder diffraction pattern substantially as shown in FIG. 1.

In some embodiments, the crystalline form has a differential scanning calorimetry thermogram showing an endotherm at about 213° C.

In some embodiments, the crystalline form has a differential scanning calorimetry thermogram substantially as shown in FIG. 2.

The present invention further provides compositions comprising crystalline Form A.

In some embodiments, at least about 50% by weight of total lactic acid salt of the compound of formula I in the composition is present as Form A.

In some embodiments, at least about 70% by weight of total lactic acid salt of the compound of formula I in the composition is present as Form A.

In some embodiments, at least about 80% by weight of total lactic acid salt of the compound of formula I in the composition is present as Form A.

In some embodiments, at least about 90% by weight of total lactic acid salt of the compound of formula I in the composition is present as Form A.

In some embodiments, at least about 95% by weight of total lactic acid salt of the compound of formula I in the composition is present as Form A.

In some embodiments, at least about 97% by weight of total lactic acid salt of the compound of formula I in the composition is present as Form A.

In some embodiments, at least about 98% by weight of total lactic acid salt of the compound of formula I in the composition is present as Form A.

In some embodiments, at least about 99% by weight of total lactic acid salt of the compound of formula I in the composition is present as Form A.

In some embodiments, the composition further comprises a pharmaceutically acceptable carrier.

In some embodiments, the composition consists essentially of the lactic acid salt of the compound of formula I wherein at least 95% by weight of the lactic acid salt of the compound of formula I is present in the composition as the Form A.

In some embodiments, the composition consists essentially of the lactic acid salt of the compound of formula I wherein at least 97% by weight of the lactic acid salt of the compound of formula I is present in the composition as the Form A.

In some embodiments, the composition consists essentially of the lactic acid salt of the compound of formula I wherein at least 98% by weight of the lactic acid salt of the compound of formula I is present in the composition as the Form A.

In some embodiments, the composition consists essentially of the lactic acid salt of the compound of formula I wherein at least 99% by weight of the lactic acid salt of the compound of formula I is present in the composition as the Form A.

The present invention further provides methods of preparing crystalline Form A comprising stirring the compound of formula I in a solution comprising water, organic solvent and lactic acid.

In some embodiments, organic solvent is an alcohol.

In some embodiments, organic solvent is selected from the group consisting of ethanol and isopropanol.

In some embodiments, the solution comprises about 6.5% water.

The present invention further provides a crystalline form prepared by any one of the methods described herein.

The present invention further provides a crystalline hydrate of a lactic acid salt of a compound of Formula I.

In some embodiments of the crystalline hydrates of the invention, the molar ratio of the hydrate water to the lactic acid salt of the compound of Formula I is about 1 or about 6.

In some embodiments of the crystalline hydrates of the invention, the hydrate is a monohydrate or hexahydrate.

In some embodiments of the crystalline hydrates of the invention, the lactic salt is a is a mono-lactic acid salt.

The present invention provides a crystalline hydrate (Form B) of a lactic acid salt of a compound of Formula I wherein the crystalline form has an X-ray powder diffraction pattern comprising characteristic peaks, in terms of 2θ, at about 17.6°, about 19.3° and about 26.0°.

In some embodiments, the X-ray powder diffraction pattern further comprises characteristic peaks, in terms of 2θ, at about 23.3°, about 23.5° and about 28.2°.

In some embodiments, the X-ray powder diffraction pattern further comprises characteristic peaks, in terms of 2θ, at about 11.9°, about 15.3°, about 16.1°, and about 18.5°.

In some embodiments, the X-ray powder diffraction pattern further comprises characteristic peaks, in terms of 2θ, at about 10.2° and about 12.9°.

In some embodiments, the X-ray powder diffraction pattern comprises at least 3 characteristic peaks, in terms of 2θ, selected from:

at about 10.2, about 11.3, about 11.6, about 11.9, about 12.9, about 15.3, about 15.6, about 16.1, about 17.6, about 18.5, about 19.3, about 22.3, about 23.3, about 23.5, about 23.9, about 26.0, about 28.2, about 29.3, about 29.8, about 30.7, about 32.2, about 32.6, about 33.1 and about 34.3°.

In some embodiments, the X-ray powder diffraction pattern is substantially as shown in FIG. 6.

In some embodiments, the crystalline form has a differential scanning calorimetry thermogram showing an endotherm at about 155° C.

In some embodiments, the crystalline form has a differential scanning calorimetry thermogram substantially as described herein.

The present invention further provides compositions comprising crystalline hydrates of a lactic acid salt of a compound of Formula I.

In some embodiments, the molar ratio of the hydrate water to the lactic acid salt of the compound of Formula I is about 1 or about 6.

In some embodiments, the hydrate is a monohydrate or hexahydrate.

In some embodiments, the lactic salt is a is a mono-lactic acid salt.

The present invention further provides compositions comprising crystalline Form B.

In some embodiments, at least about 50% by weight of hydrate of lactic acid salt of the compound of formula I in the composition is present as Form B.

In some embodiments, at least about 70% by weight of hydrate of lactic acid salt of the compound of formula I in the composition is present as Form B.

In some embodiments, at least about 80% by weight of hydrate of lactic acid salt of the compound of formula I in the composition is present as Form B.

In some embodiments, at least about 90% by weight of hydrate of lactic acid salt of the compound of formula I in the composition is present as Form B.

In some embodiments, at least about 95% by weight of hydrate of lactic acid salt of the compound of formula I in the composition is present as Form B.

In some embodiments, at least about 99% by weight of hydrate of lactic acid salt of the compound of formula I in the composition is present as Form B.

In some embodiments, the composition further comprises a pharmaceutically acceptable carrier.

The present invention further provides methods of preparing crystalline Form B comprising suspending Form A in a solution comprising water and an organic solvent at a temperature of about 20° C. to about 60° C., wherein said water is present in said solution in an amount of about 5% to about 20% by volume.

In some embodiments, the organic solvent comprises an alcohol, a ketone, an organic nitrile, or mixture thereof.

In some embodiments, the organic solvent comprises one or more of ethanol, acetone, methyl ethyl ketone, and acetonitrile.

In some embodiments, Form B is prepared by suspending Form A in a solution comprising water and an organic solvent at a temperature of about 20° C. to about 60° C., wherein said water is present in said solution in an amount of about 5% to about 20% by volume.

The present invention further provides a crystalline hydrate (Form C) wherein the crystalline form has an X-ray powder diffraction pattern comprising characteristic peaks, in terms of 2θ, at from about 3.2° to about 3.6°, at from about 6.5° to about 7.1°, and at from about 9.8° to about 10.6°.

In some embodiments, the X-ray powder diffraction pattern further comprises a characteristic peak, in terms of 2θ, at from about 13.3° to about 14.1°.

In some embodiments, the X-ray powder diffraction pattern further comprises a characteristic peak, in terms of 2θ, at about 27.3 to about 27.5°.

In some embodiments, the X-ray powder diffraction pattern further comprises characteristic peaks, in terms of 2θ, at from about 17.6° to about 17.8°, and at from about 24.7° to about 24.9°.

In some embodiments, the X-ray powder diffraction pattern comprises at least 3 characteristic peaks, in terms of 2θ, selected from:

at from about 3.2 to about 3.6, at from about 6.5 to about 7.1, at from about 9.8 to about 10.6, at from about 13.3 to about 14.1, at from about 17.6 to about 17.8, at about 18.8, at about 20.2, at from about 24.7 to about 24.9, at about 27.3 to about 27.5, at about 28.0, and at from about 29.0 to about 29.3°.

In some embodiments, the X-ray powder diffraction pattern is substantially as shown in FIG. 7 or as described herein.

In some embodiments, the crystalline hydrate of has a differential scanning calorimetry thermogram showing a prominent endotherm at about 150° C.

In some embodiments, the crystalline hydrate of has a differential scanning calorimetry thermogram substantially as described herein.

The present invention further provides compositions comprising crystalline Form C.

In some embodiments, at least about 50% by weight of hydrate of lactic acid salt of the compound of formula I in the composition is present as Form C.

In some embodiments, at least about 70% by weight of hydrate of lactic acid salt of the compound of formula I in the composition is present as Form C.

In some embodiments, at least about 80% by weight of hydrate of lactic acid salt of the compound of formula I in the composition is present as Form C.

In some embodiments, at least about 90% by weight of hydrate of lactic acid salt of the compound of formula I in the composition is present as Form C.

In some embodiments, at least about 95% by weight of hydrate of lactic acid salt of the compound of formula I in the composition is present as Form C.

In some embodiments, at least about 99% by weight of hydrate of lactic acid salt of the compound of formula I in the composition is present as Form C.

In some embodiments, the composition further comprises a pharmaceutically acceptable carrier.

The present invention further provides methods of preparing crystalline Form C comprising contacting the amorphous form of said lactic acid salt of said compound of Formula I with a relative humidity of from about 50% to about 75% at a temperature of from about 40° C. to about 80° C.

In some embodiments, the contacting is performed for at least about 6 hours.

In some embodiments, Form C is prepared by contacting the amorphous form of said lactic acid salt of said compound of Formula I with a relative humidity of from about 50% to about 75% at a temperature of from about 40° C. to about 80° C.

The present invention further provides methods of preparing a crystalline hydrate of a lactic acid salt of a compound of Formula I comprising diffusing organic solvent vapor into an aqueous solution of said lactic acid salt of said compound of Formula I at a temperature of about 0° C. to about 10° C.

In some embodiments, the molar ratio of the hydrate water to the lactic acid salt of the compound of Formula I in the crystalline hydrate is about 1 or about 6.

In some embodiments, the crystalline hydrate is a monohydrate or hexahydrate.

In some embodiments, the lactic salt in the crystalline hydrate is a is a mono-lactic acid salt.

In some embodiments, the crystalline hydrate is Form C.

In some embodiments, the organic solvent comprises an organic nitrile.

In some embodiments, the organic nitrile is acetonitrile.

In some embodiments, the temperature is about 5° C.

In some embodiments, a crystalline hydrate of a lactic acid salt of a compound of Formula I is prepared by the method of diffusing organic solvent vapor into an aqueous solution of said lactic acid salt of said compound of Formula I at a temperature of about 0° C. to about 10° C.

In some embodiments, a crystalline hydrate of a lactic acid salt of a compound of Formula I is prepared by the method of diffusing organic solvent vapor into an aqueous solution of said lactic acid salt of said compound of Formula I at a temperature of about 0° C. to about 10° C.

In some embodiments, a crystalline hydrate of a lactic acid salt of a compound of Formula I is prepared by the method of diffusing organic solvent vapor into an aqueous solution of said lactic acid salt of said compound of Formula I at a temperature of about 0° C. to about 10° C., wherein the molar ratio of the hydrate water to the lactic acid salt of the compound of Formula I in the crystalline hydrate is about 1 or about 6.

In some embodiments, a crystalline hydrate of a lactic acid salt of a compound of Formula I is prepared by the method of diffusing organic solvent vapor into an aqueous solution of said lactic acid salt of said compound of Formula I at a temperature of about 0° C. to about 10° C., wherein the crystalline hydrate is a monohydrate or hexahydrate.

In some embodiments, a crystalline hydrate of a lactic acid salt of a compound of Formula I is prepared by the method of diffusing organic solvent vapor into an aqueous solution of said lactic acid salt of said compound of Formula I at a temperature of about 0° C. to about 10° C., wherein the lactic salt in the crystalline hydrate is a is a mono-lactic acid salt.

In some embodiments, Form C is prepared by the method of diffusing organic solvent vapor into an aqueous solution of said lactic acid salt of said compound of Formula I at a temperature of about 0° C. to about 10° C., wherein the lactic salt in the crystalline hydrate is a is a mono-lactic acid salt.

The present invention provides a crystalline hydrate (Form D) of a lactic acid salt of a compound of Formula I wherein the crystalline form has an X-ray powder diffraction pattern comprising characteristic peaks, in terms of 2θ, at about 4.0° and at about 27.2°.

In some embodiments, the X-ray powder diffraction pattern further comprises a characteristic peak, in terms of 2θ, at about 22.0°.

In some embodiments, the X-ray powder diffraction pattern further comprises characteristic peaks, in terms of 2θ, at about 14.3° and at about 16.4°.

In some embodiments, the X-ray powder diffraction pattern further comprises characteristic peaks, in terms of 2θ, at about 8.0° and at about 20.1°.

In some embodiments, the X-ray powder diffraction pattern comprises at least 3 characteristic peaks, in terms of 2θ, selected from: at about 4.0, about 8.0, about 11.5, about 12.0, about 14.3, about 15.8, about 16.4, about 20.1, about 21.2, about 22.0, about 23.6, about 27.2 and about 27.9 degrees.

In some embodiments, the X-ray powder diffraction pattern is substantially as shown in FIG. 8.

In some embodiments, the crystalline form has a differential scanning calorimetry thermogram showing an endotherm at about 73° C., an endotherm at about 145° C., an exotherm at about 160° C., and an endotherm at about 189° C.

In some embodiments, the crystalline form has a differential scanning calorimetry thermogram substantially as described herein.

The present invention further provides compositions comprising crystalline Form D.

In some embodiments, at least about 50% by weight of hydrate of lactic acid salt of the compound of formula I in the composition is present as Form D.

In some embodiments, at least about 70% by weight of hydrate of lactic acid salt of the compound of formula I in the composition is present as Form D.

In some embodiments, at least about 80% by weight of hydrate of lactic acid salt of the compound of formula I in the composition is present as Form D.

In some embodiments, at least about 90% by weight of hydrate of lactic acid salt of the compound of formula I in the composition is present as Form D.

In some embodiments, at least about 95% by weight of hydrate of lactic acid salt of the compound of formula I in the composition is present as Form D.

In some embodiments, at least about 99% by weight of hydrate of lactic acid salt of the compound of formula I in the composition is present as Form D.

In some embodiments, the composition further comprises a pharmaceutically acceptable carrier.

The present invention further provides methods of preparing crystalline Form D comprising contacting the amorphous form of said lactic acid salt of said compound of Formula I with an inert atmosphere having a relative humidity of about 30% or less at a temperature of from about 80° C. to about 150° C.

In some embodiments, the temperature is about 120° C.

In some embodiments, the contacting is performed for at least about 5 hours.

In some embodiments, a hydrate of a lactic acid salt of a compound of Formula I is prepared by the method of contacting the amorphous form of said lactic acid salt of said compound of Formula I with an inert atmosphere having a relative humidity of about 30% or less at a temperature of from about 80° C. to about 150° C.

In some embodiments, Form D is prepared by the method of contacting the amorphous form of said lactic acid salt of said compound of Formula I with an inert atmosphere having a relative humidity of about 30% or less at a temperature of from about 80° C. to about 150° C.

The present invention further provides a crystalline hydrate (Form E) of a lactic acid salt of a compound of Formula I wherein the crystalline form has an X-ray powder diffraction pattern comprising characteristic peaks, in terms of 2θ, at about 13.4° and at about 25.5°.

In some embodiments, the X-ray powder diffraction pattern further comprises characteristic peaks, in terms of 2θ, at about 22.6°, at about 24.1°, at about 25.0°, and at about 27.7°.

In some embodiments, the X-ray powder diffraction pattern further comprises characteristic peaks, in terms of 2θ, at about 12.1° and at about 18.1°.

In some embodiments, the X-ray powder diffraction pattern further comprises characteristic peaks, in terms of 2θ, at about 6.1° and at about 8.4°.

In some embodiments, the X-ray powder diffraction pattern comprises at least 3 characteristic peaks, in terms of 2θ, selected from:
at about 6.1, about 8.4, about 8.7, about 12.1, about 13.4, about 14.9, about 18.1, about 19.0, about 20.1, about 21.1 about 21.5, about 22.6, about 24.1, about 24.5, about 25.0, about 25.5, about 27.7, about 30.1, and about 30.6 degrees.

In some embodiments, the X-ray powder diffraction pattern is substantially as shown in FIG. 9.

In some embodiments, the crystalline form has a differential scanning calorimetry thermogram showing an endotherm at about 76° C., and an endotherm at about 128° C.

In some embodiments, the crystalline form has a differential scanning calorimetry thermogram substantially as described herein.

The present invention further provides compositions comprising crystalline Form E.

In some embodiments, at least about 50% by weight of hydrate of lactic acid salt of the compound of formula I in the composition is present as Form E.

In some embodiments, at least about 70% by weight of hydrate of lactic acid salt of the compound of formula I in the composition is present as Form E.

In some embodiments, at least about 80% by weight of hydrate of lactic acid salt of the compound of formula I in the composition is present as Form E.

In some embodiments, at least about 90% by weight of hydrate of lactic acid salt of the compound of formula I in the composition is present as Form E.

In some embodiments, at least about 95% by weight of hydrate of lactic acid salt of the compound of formula I in the composition is present as Form E.

In some embodiments, at least about 99% by weight of hydrate of lactic acid salt of the compound of formula I in the composition is present as Form E.

In some embodiments, the composition further comprises a pharmaceutically acceptable carrier.

The present invention further provides methods of preparing crystalline Form E comprising suspending Form A in water.

In some embodiments, a hydrate of a lactic acid salt of a compound of Formula I is prepared by the method of suspending Form A in water.

In some embodiments, Form E is prepared by the method of suspending Form A in water.

The present invention further provides methods of preparing crystalline Form E comprising seeding an aqueous solution of a lactic acid salt of the compound of Formula I with seed crystals of crystalline Form E, wherein the concentration of said solution is about 100 to about 200 mg/mL.

In some embodiments, a hydrate of a lactic acid salt of a compound of Formula I is prepared by the method of seeding an aqueous solution of a lactic acid salt of the compound of Formula I with seed crystals of crystalline Form E, wherein the concentration of said solution is about 100 to about 200 mg/mL.

In some embodiments, Form E is prepared by the method of seeding an aqueous solution of a lactic acid salt of the compound of Formula I with seed crystals of crystalline Form E, wherein the concentration of said solution is about 100 to about 200 mg/mL.

The present invention further provides methods of preparing crystalline Form E comprising crystallizing a lactic acid salt of the compound of Formula I in a solvent, wherein the solvent comprises about 1 to about 10% by volume of water and about 90 to about 99% by volume of an organic solvent.

In some embodiments, the solvent comprises about 4% by volume of water.

In some embodiments, the organic solvent comprises THF or ethyl acetate.

In some embodiments, crystallizing Form B is facilitated by suspending the amorphous form of a lactic acid salt of said compound of Formula I in a solvent, at a temperature of about 5° C., for a time of at least about 5 days, wherein said solvent comprises about 5% water by volume and about 95% acetonitrile by volume.

The present invention further provides methods of preparing crystalline Form E comprising adding an aqueous solution of a lactic acid salt of a compound of Formula I to a solvent at a temperature of about 2° C. to about 30° C., wherein the concentration of the aqueous solution is about 100 to about 400 mg/mL, and the solvent comprises ethyl acetate and tetrahydrofuran.

In some embodiments, the ratio of the aqueous solution to the ethyl acetate to the tetrahydrofuran is about 1:10:5 by volume.

In some embodiments, a hydrate of a lactic acid salt of a compound of Formula I is prepared by the method of adding an aqueous solution of a lactic acid salt of a compound of Formula I to a solvent at a temperature of about 2° C. to about 30° C., wherein the concentration of the aqueous solution is about 100 to about 400 mg/mL, and the solvent comprises ethyl acetate and tetrahydrofuran.

In some embodiments, Form E is prepared by the method of adding an aqueous solution of a lactic acid salt of a compound of Formula I to a solvent at a temperature of about 2° C. to about 30° C., wherein the concentration of the aqueous solution is about 100 to about 400 mg/mL, and the solvent comprises ethyl acetate and tetrahydrofuran.

The present invention also provides for solid compositions (i.e., formulations) for oral administration containing a crystalline hydrate form of a lactic acid salt of the compound of Formula I.

In some embodiments, the molar ratio of the hydrate water to the lactic acid salt of the compound of Formula I in the crystalline hydrate is about 1 or about 6.

In some embodiments, the crystalline hydrate is a monohydrate or hexahydrate.

In some embodiments, the lactic salt in the crystalline hydrate is a is a mono-lactic acid salt.

In some embodiments, the crystalline hydrate is Form B.
In some embodiments, the crystalline hydrate is Form C.
In some embodiments, the crystalline hydrate is Form D.
In some embodiments, the crystalline hydrate is Form E.
In some embodiments, the formulation is in the form of a powder.

In some embodiments, the crystalline hydrate remains substantially intact under ambient conditions for a period greater than about 36 hours.

In some embodiments, the crystalline hydrate remains substantially intact under ambient conditions for a period greater than about 1 week.

In some embodiments, the crystalline hydrate remains substantially intact under ambient conditions for a period greater than about 1 month.

In some embodiments, the crystalline hydrate remains substantially intact under ambient conditions for a period greater than about 6 months.

In some embodiments, the crystalline hydrate remains substantially intact under ambient conditions for a period greater than about 1 year.

The present invention also provides a dosage form which contains solid formulations described herein containing a crystalline hydrate form of a lactic acid salt of the compound of Formula I.

In some embodiments, the dosage form is a pill, tablet, capsule, or caplet.

The present invention further provides methods of treating a patient comprising administering to the patient a formulation comprising a crystalline hydrate form of a lactic acid salt of the compound of Formula I.

In some embodiments, the molar ratio of the hydrate water to the lactic acid salt of the compound of Formula I in the crystalline hydrate is about 1 or about 6.

In some embodiments, the crystalline hydrate is a monohydrate or hexahydrate.

In some embodiments, the lactic salt in the crystalline hydrate is a is a mono-lactic acid salt.

In some embodiments, the crystalline hydrate is Form B.
In some embodiments, the crystalline hydrate is Form C.
In some embodiments, the crystalline hydrate is Form D.
In some embodiments, the crystalline hydrate is Form E.
In some embodiments, the patient is a cancer patient.
In some embodiments, the patient has been diagnosed with multiple myeloma (MM), acute myelogenous leukemia (AML), prostate cancer, breast cancer, colon cancer, or melanoma.

In some embodiments, the patient is a refractory patient.
In some embodiments, the patient is treated with a dose that is less than the maximum tolerated dose (MTD). In further embodiments, the dose comprises 0.25 to 30 mg/kg of the lactic acid salt of the compound of formula I.

In some embodiments, the formulation is in solid form at the time of administration.

The present invention further provides a mesomorphic form (Form H) of a hydrate of lactic acid salt of the compound of Formula I wherein the mesomorphic form has an X-ray powder diffraction pattern comprising characteristic peaks, in terms of 2θ, at about 3.5° and at about 26.4°.

In some embodiments, the X-ray powder diffraction pattern further comprises a characteristic peak, in terms of 2θ, at about 16.7°.

In some embodiments, the X-ray powder diffraction pattern further comprises a characteristic peak, in terms of 2θ, at about 20.6°.

In some embodiments, the X-ray powder diffraction pattern further comprises a characteristic peak, in terms of 2θ, at about 6.9°.

In some embodiments, the X-ray powder diffraction pattern is substantially as shown in FIG. 12.

The present invention further provides methods of preparing the mesomorphic Form H, comprising adding an aqueous solution of a lactic acid salt of the compound of Formula I to a solvent at a temperature of about 0 to about 10° C., wherein the concentration of the aqueous solution is about 100 to about 350 mg/mL; and the solvent comprises acetonitrile.

In some embodiments, the ratio of the aqueous solution to the acetonitrile is about 1:10 by volume.

In some embodiments, the mixture obtained by the addition is allowed to stand at about 0 to about 10° C. for at least about 24 hours.

In some embodiments, the mixture obtained by the addition is allowed to stand at about 2° C. for at least about 24 hours.

In some embodiments, Form H is prepared by the method of adding an aqueous solution of a lactic acid salt of the compound of Formula I to a solvent at a temperature of about 0 to about 10° C., wherein the concentration of the aqueous solution is about 100 to about 350 mg/mL; and the solvent comprises acetonitrile.

The present invention further provides methods of preparing the mesomorphic Form H, comprising evaporating an aqueous solution of a lactic acid salt of the compound of Formula I at a temperature of about 20 to about 30° C.

In some embodiments, Form H is prepared by the method of evaporating an aqueous solution of a lactic acid salt of the compound of Formula I at a temperature of about 20 to about 30° C.

In some embodiments of Form H, the lactic acid salt of said compound of Formula I is a mono-lactic acid salt.

The present invention further provides compositions comprising mesomorphic Form H.

In some embodiments, at least about 50% by weight of hydrate of lactic acid salt of the compound of formula I in the composition is present as Form H.

In some embodiments, at least about 70% by weight of hydrate of lactic acid salt of the compound of formula I in the composition is present as Form H.

In some embodiments, at least about 80% by weight of hydrate of lactic acid salt of the compound of formula I in the composition is present as Form H.

In some embodiments, at least about 90% by weight of hydrate of lactic acid salt of the compound of formula I in the composition is present as Form H.

In some embodiments, at least about 95% by weight of hydrate of lactic acid salt of the compound of formula I in the composition is present as Form H.

In some embodiments, at least about 99% by weight of hydrate of lactic acid salt of the compound of formula I in the composition is present as Form H.

In some embodiments, the composition further comprises a pharmaceutically acceptable carrier.

The present invention provides a crystalline hydrate (Form I) of a lactic acid salt of a compound of Formula I wherein the crystalline form has an X-ray powder diffraction pattern comprising characteristic peaks, in terms of 2θ, at about 2.3° and at about 11.9°.

In some embodiments, the X-ray powder diffraction pattern further comprises characteristic peaks, in terms of 2θ, at about 9.8° and about 15.7°.

In some embodiments, the X-ray powder diffraction pattern further comprises characteristic peaks, in terms of 2θ, at about 8.1° and about 21.5°.

In some embodiments, the X-ray powder diffraction pattern is substantially as shown in FIG. 13.

In some embodiments, the lactic acid salt is a mono-lactic acid salt.

The present invention further provides compositions comprising crystalline Form I.

In some embodiments, the composition further comprises water.

In some embodiments, the composition further comprises a pharmaceutically acceptable carrier.

The present invention further provides methods of treating a patient comprising administering to the patient a pharmaceutical formulation containing crystalline Form I.

In some embodiments, the patient is a cancer patient.

In some embodiments, the patient has been diagnosed with multiple myeloma (MM), acute myelogenous leukemia (AML), prostate cancer, breast cancer, colon cancer, or melanoma.

In some embodiments, the patient is a refractory patient.

The present invention further provides a method of preparing Form I comprising combining Form A with a solvent containing at least about 50% by volume of water.

In some embodiments, Form I is prepared by the method of combining Form A with a solvent containing at least about 50% by volume of water.

The present invention further provides a crystalline solvate of a lactic acid salt of the compound of Formula I.

In some embodiments, the solvate is a 1,4-dioxane-solvate.

The present invention further provides a crystalline 1,4-dioxane-solvate of a lactic acid salt of the compound of Formula I wherein the solvate has an X-ray powder diffraction pattern comprising characteristic peaks, in terms of 2θ, at about 5.2° and at about 25.0°.

In some embodiments, the X-ray powder diffraction pattern further comprises characteristic peaks, in terms of 2θ, at about 21.2° and about 15.2°.

In some embodiments, the X-ray powder diffraction pattern further comprises characteristic peaks, in terms of 2θ, at about 10.4° and about 26.0°.

In some embodiments, the X-ray powder diffraction pattern is substantially as shown in FIG. 10.

In some embodiments, the solvate is a hemisolvate.

The present invention further provides compositions comprising a crystalline solvate of a lactic acid salt of the compound of Formula I.

In some embodiments, the solvate is a 1,4-dioxane-solvate.

The present invention further provides compositions comprising a crystalline 1,4-dioxane-solvate of a lactic acid salt of the compound of Formula I wherein the solvate has an X-ray powder diffraction pattern comprising characteristic peaks, in terms of 2θ, at about 5.2° and at about 25.0°.

In some embodiments, the X-ray powder diffraction pattern further comprises characteristic peaks, in terms of 2θ, at about 21.2° and about 15.2°.

In some embodiments, the X-ray powder diffraction pattern further comprises characteristic peaks, in terms of 2θ, at about 10.4° and about 26.0°.

In some embodiments, the X-ray powder diffraction pattern is substantially as shown in FIG. 10.

In some embodiments, the composition further comprises a pharmaceutically acceptable carrier.

The present invention further provides methods of preparing a crystalline 1,4-dioxane-solvate of a lactic acid salt of the compound of Formula I comprising crystallizing the 1,4-dioxane-solvate from a solution containing 1,4-dioxane.

In some embodiments, a crystalline 1,4-dioxane-solvate of a lactic acid salt of the compound of Formula I is prepared by the method of crystallizing the 1,4-dioxane-solvate from a solution containing 1,4-dioxane.

In some embodiments, the solvate is a mono-lactic acid salt.

The present invention further provides a crystalline benzene-solvate of a lactic acid salt of the compound of Formula I.

In some embodiments, the solvate is a hemisolvate.

In some embodiments, the solvate is a mono-lactic acid salt.

The present invention further provides a crystalline benzene-solvate of a lactic acid salt of the compound of Formula I wherein the solvate has an X-ray powder diffraction pattern comprising characteristic peaks, in terms of 2θ, at about 5.4° and at about 24.7°.

In some embodiments, the X-ray powder diffraction pattern further comprises characteristic peaks, in terms of 2θ, at about 10.3° and about 21.5°.

In some embodiments, the X-ray powder diffraction pattern further comprises characteristic peaks, in terms of 2θ, at about 15.2° and about 27.3°.

In some embodiments, the X-ray powder diffraction pattern is substantially as shown in FIG. 11.

In some embodiments, the solvate is a hemisolvate.

The present invention further provides compositions comprising a crystalline benzene-solvate of a lactic acid salt of the compound of Formula I.

The present invention further provides compositions comprising a crystalline benzene-solvate of a lactic acid salt of the compound of Formula I wherein the solvate has an X-ray powder diffraction pattern comprising characteristic peaks, in terms of 2θ, at about 5.4° and at about 24.7°.

In some embodiments, the X-ray powder diffraction pattern further comprises characteristic peaks, in terms of 2θ, at about 10.3° and about 21.5°.

In some embodiments, the X-ray powder diffraction pattern further comprises characteristic peaks, in terms of 2θ, at about 15.2° and about 27.3°.

In some embodiments, the X-ray powder diffraction pattern is substantially as shown in FIG. 11.

In some embodiments, the solvate is a hemisolvate.

In some embodiments, the composition further comprises a pharmaceutically acceptable carrier.

The present invention further provides methods preparing a crystalline benzene-solvate of a lactic acid salt of the compound of Formula I comprising crystallizing the crystalline benzene-solvate from a solution comprising benzene.

In some embodiments, a crystalline benzene-solvate of a lactic acid salt of the compound of Formula I is prepared by crystallizing the crystalline benzene-solvate from a solution comprising benzene.

The present invention further provides any crystalline form described herein or formulation thereof for use in therapy.

The present invention further provides any crystalline form described herein or formulation thereof for use in the preparation of a medicament for use in therapy.

DETAILED DESCRIPTION

Non-Hydrate Crystalline Forms: Form A

In a first aspect, the present invention provides, inter alia, formulations, such as solid (e.g., powder) formulations for oral administration, of a lactic acid salt of the compound of formula I:

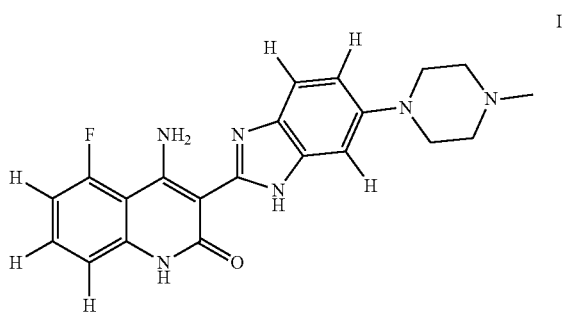 [SMILES: CN1CCN(c2ccc3nc(-c4c(N)c5c(F)cccc5[nH]c4=O)[nH]c3c2)CC1]

A lactic acid salt which is present in the formulations of the invention contains a non-hydrate crystalline form of the lactic acid salt of the compound of formula I. By "non-hydrate crystalline form" is meant any lactic acid salt of the compound of formula I which is in substantially anhydrous form or non-solvated form, including both hygroscopic, slightly hygroscopic, and non-hygroscopic anhydrous forms. Lactic acid salts can further include mono- and di-acid salt forms, and the like. Preferably, the lactic acid salt is a mono-lactic acid salt of the compound of formula I. Di-lactic acid salts (i.e., bis-lactic acid salts), tri-lactic acid salts (i.e., tris-lactic acid salts) and intermediate and higher orders of salts are also encompassed and can be formed by the combination of greater than one equivalent of lactic acid with the compound of formula I according to routine methods of preparing acid addition salts.

In some embodiments, the non-hydrate crystalline form of the lactic acid salt of the compound of formula I is crystalline Form A. Form A can be characterized by any one or more solid state techniques such as X-ray powder diffraction (XRPD), single crystal X-ray diffraction, differential scanning calorimetry (DSC), dynamic vapor sorption (DVS), crystal morphology, solid state nuclear magnetic resonance, Raman scattering, infrared (IR) spectroscopy, and the like. In some embodiments, Form A can be identified by its XRPD pattern. In some embodiments, Form A can be identified by its DSC thermogram. In some embodiments, Form A can be identified by crystal morphology. In some embodiments, Form A can be identified by its DVS cycle. Other techniques, alone or in combination with the ones recited herein, can also be used to identify Form A.

Figure 1:
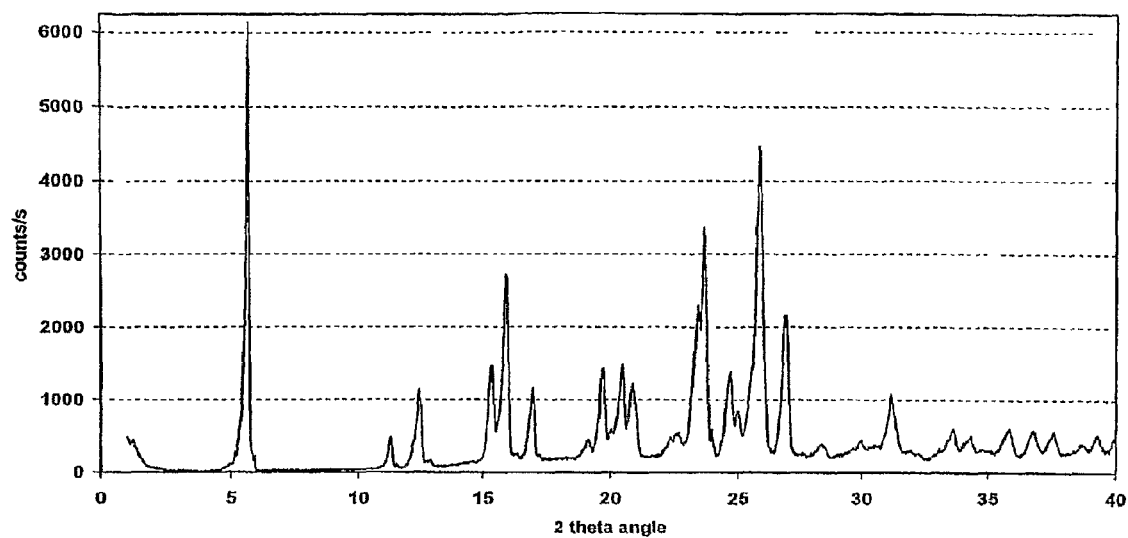
FIG. 1 shows an XRPD pattern characteristic of Form A.

Crystalline Form A is characterized as an anhydrous, non-hygroscopic crystalline form of the mono-lactic acid salt of the compound of formula I. Form A can be identified by its X-ray powder diffraction (XRPD) pattern which is provided in FIG. 1. In some embodiments, the crystalline form of the invention has an XRPD pattern substantially as shown in FIG. 1 (two-theta values provided in Example 3), where the term "substantially" in this instance indicates that two-theta values for individual peaks can vary about ±0.2°. The relative intensities of the peaks can also vary, depending upon the sample preparation technique, the sample mounting procedure and the particular instrument employed. Powder X-ray diffraction two-theta data consistent with Form A is provided in Example 3 below. As discussed above, many factors can affect the 2-theta values. Therefore, the peak assignments listed in Example 3 can vary by plus or minus about 0.2°.

Figure 2:
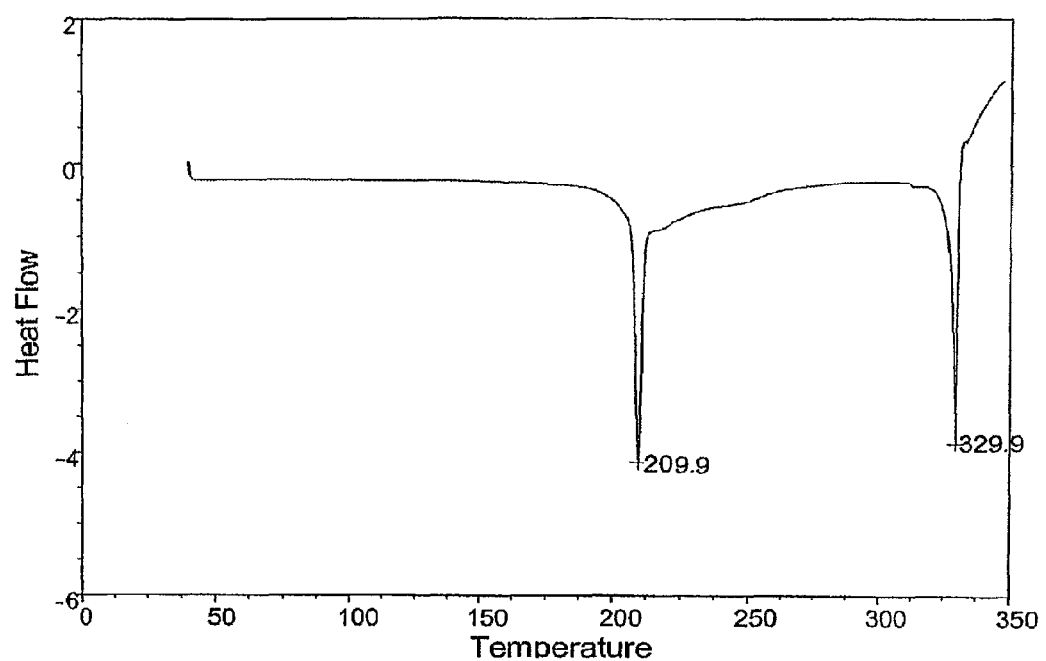
FIG. 2 shows a DSC thermogram characteristic of Form A.

The crystalline Form A of the invention can be further recognized by its differential scanning calorimetry (DSC) thermogram which has a characteristic endothermic peak 210° C. A typical DSC thermogram for a sample containing substantially pure Form A is provided in FIG. 2. In some embodiments, the crystalline form of the invention has a DSC trace substantially as shown in FIG. 2, where the term "substantially" in this instance indicates that features such as endotherms, exotherms, baseline shifts, etc. can vary about ±4° C. For DSC, it is known that the temperatures observed will depend upon the rate of temperature change as well as sample preparation technique and the particular instrument employed. Thus, the values reported herein relating to DSC thermograms can vary by plus or minus about 4° C.

Figure 3:
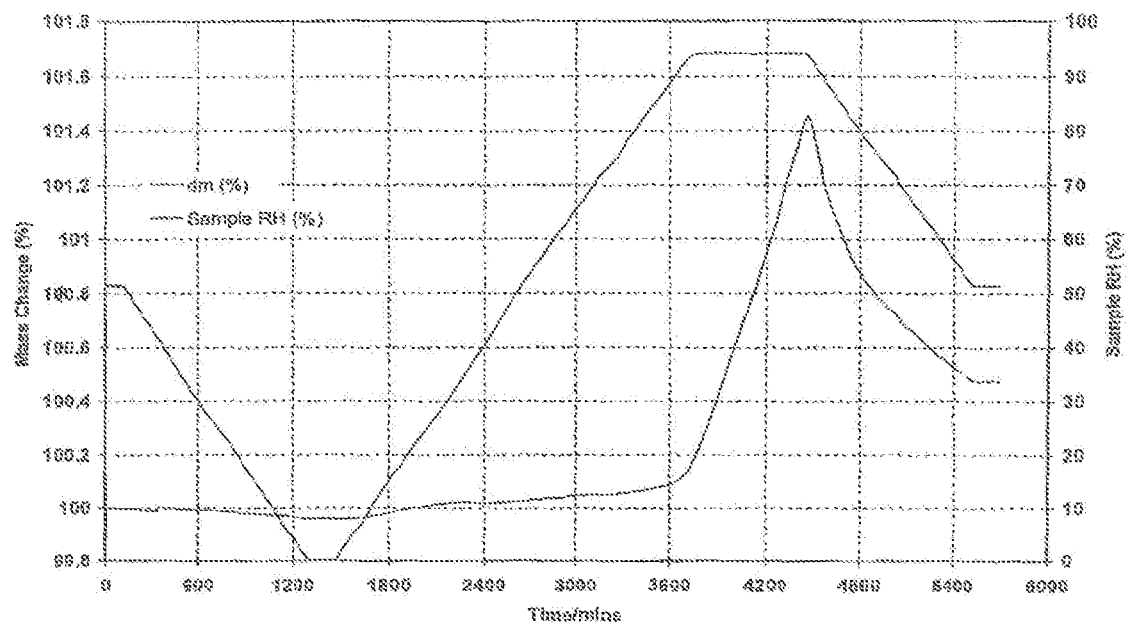
FIG. 3 shows a DVS cycle (mass change v. time) characteristic of Form A.
Figure 4:
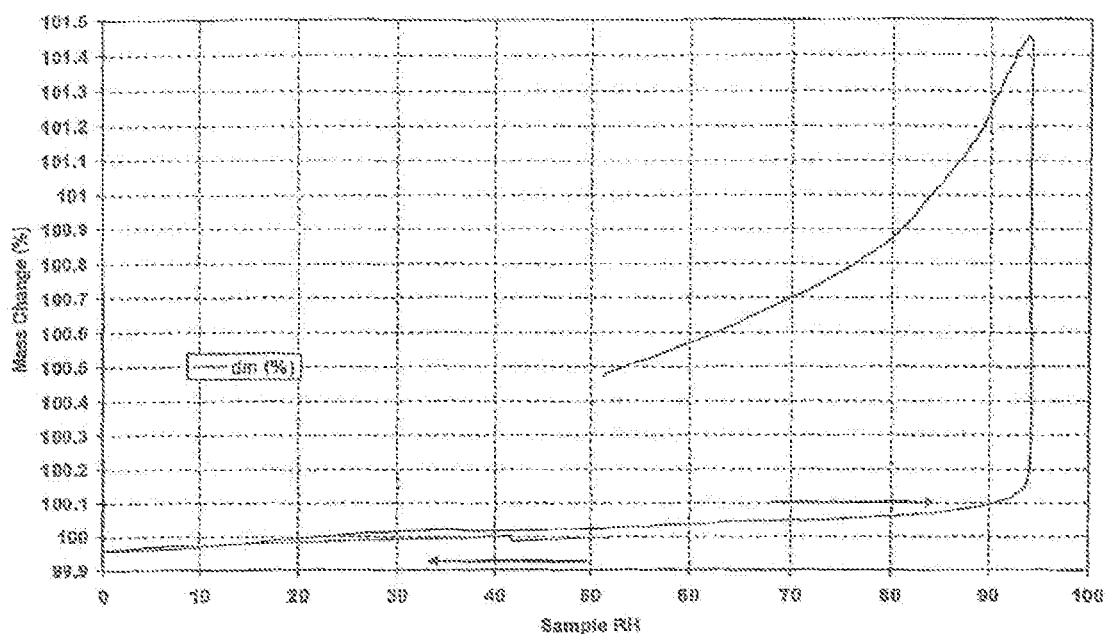
FIG. 4 shows a DVS cycle (mass change v. RH) characteristic of Form A.

Sorption/desorption data according to dynamic vapor sorption techniques, such as provided in Example 3 and FIGS. 3 and 4, further indicate that Form A can be characterized as a non-hygroscopic material.

Crystalline Form A can be prepared by any of numerous methods in the art. In some embodiments, Form A can be prepared by combining the compound of formula I with lactic acid in a solvent and precipitating crystalline Form A from the resulting solution. In some embodiments, the molar ratio of compound of formula I to lactic acid is about 10:1 to about 1:10, about 5:1 to about 1:5, about 2:1 to about 1:2, or about 1:1.

An example method for preparing Form A is as follows:

(a) suspending the compound of formula I (or the tautomers thereof) in a solvent or mixture of solvents;

(b) contacting lactic acid with the compound of formula I to provide a mixture;

(c) heating the mixture;

(d) cooling the mixture; and (e) isolating Form A.

In some embodiments, the mixture is heated and refluxed prior to cooling. In further embodiments, the isolating step includes filtering the mixture. In further embodiments, the lactic acid may be a mixture of the D and L forms of lactic acid or may be the D lactic acid or the L lactic acid.

Suitable solvents include organic solvents, such as organic solvents that can at least partially dissolve the lactic acid salt of the compound of formula I. Example organic solvents include alcohols (e.g., methanol, ethanol, ispropanol, glycols, etc.), ketones (e.g., acetone, methylethyl ketone, etc.), nitriles (e.g., acetonitrile, propionitril, etc.), hydrocarbons (heptane, hexanes, pentane, benzene, toluene, etc.), halogenated hydrocarbons (e.g., dichloromethane and the like), ethers (diethyl ether, methyl-t-butyl ether, tetrahydrofuran, etc.), dimethylformamide, dimethylsulfoxide, mixtures thereof, and the like. Suitable solvents can further include mixtures of organic solvents and water. In some embodiments, the weight percent of water in the organic solvent is less than about 10%, less than about 9%, less than about 8%, less than about 7%, less than about 6%, less than about 5%, less than about 4%, less than about 3%, less than about 2.5%, less than about 2%, less than about 1.5%, less than about 1%, less than about 0.5%, or less than about 0.2%. In some embodiments, the solvent used in the method of preparing the salt is a protic solvent. In other embodiments of the invention, the solvent used in the method of preparing the salt is selected from the group consisting of methanol, ethanol, propanol, isopropanol, butanol, 2-butanol, acetone, butanone, dioxanes, water, tetrahydrofuran, and combinations of these. In some embodiments, the solvent contains an alcohol such as ethanol or isopropanol. In some embodiments, the solvent contains a mixture of alcohol and water such as, for example, less than about 10% water, less than about 7.5% water, 6.5% water, less than about 5% water, less than about 2.5% water, or less than about 1% water. In some embodiments, the solvent is acetone. In some embodiments, the solvent is tetrahydrofuran optionally containing water (e.g., about 10% by weight). In some embodiments, the solvent is acetonitrile. In some embodiments, the solvent is heptane containing 1% Tween 80. In some embodiments, the solvent is toluene.

Precipitation of crystalline Form A of the invention from solution can be carried out by any suitable manner according to routine methods. For example, solutions of a lactic acid salt of the compound of Formula I can be evaporated, cooled, treated with antisolvent, or combinations thereof. Treatment with antisolvent can be carried out by layering or vapor diffusion techniques. Suitable antisolvents include organic solvents, as well as water, that are miscible with the crystallizing solvent, yet are relatively poor solvents for the subject compound.

The methods for preparation of Form A provided herein can result in substantially pure Form A (e.g., compositions containing less than about 20%, about 10%, about 5%, or about 3% by weight of impurities, amorphous material and/or other crystalline forms) as well as mixtures enriched in Form A (e.g., mixtures containing greater than about 50% by weight Form A relative to, for example, impurities, amorphous material or other crystalline forms). Accordingly, the present invention further provides compositions containing Form A. In some embodiments, at least about 50%, at least about 70%, at least about 80%, at least about 90%, at least about 95%, at least about 97%, at least about 98%, or at least about 99% by weight of total lactic acid salt of the compound of formula I in a composition is present as Form A. In further embodiments, compositions of the present invention consist essentially of a lactic acid salt of the compound of formula I where at least about 95%, at least about 97%, at least about 98%, or at least about 99% of the lactic acid salt of the compound of formula I is present in the composition as Form A. In further embodiments, compositions of the present invention consist essentially of a lactic acid salt of the compound of formula I where at least about 98.0%, at least about 98.1%, at least about 98.2%, at least about 98.3%, at least about 98.4%, at least about 98.5%, at least about 98.6%, at least about 98.7%, at least about 98.8%, at least about 98.9%, at least about 99.0%, at least about 99.1%, at least about 99.2%, at least about 99.3%, at least about 99.4%, at least about 99.5%, at least about 99.6%, at least about 99.7%, at least about 99.8%, at least about 99.9%, of the lactic acid salt of the compound of formula I is present in the composition as Form A. In some embodiments, the remainder lactic acid salt of the compound of formula I is present in amorphous form or one or more other crystalline forms (including solvates and hydrates). Amounts of different crystalline forms of in a composition can be determined by routine spectroscopic methods, such as X-ray powder diffraction, DSC, and the like. The instant invention also provides for solid compositions (i.e., formulations) containing a non-hydrate crystalline form of a lactic acid salt of the compound of Formula I (e.g., Form A) with pharmaceutically acceptable carriers, excipients, binders, diluents or the like, to treat or ameliorate a variety of disorders related to the activity of VEGF-RTK, more particularly for example, angiogenesis associated with cancer. Pharmaceutically acceptable excipients, diluents, binders, carriers and the like include, but are not limited to, microcrystalline cellulose, lactose, dibasic calcium phosphate, tribasic calcium phosphate, sodium starch glycolate (NaSG), crospovidone, crosscarmellose (CC), sodium lauryl sulfate (SLS), Tween, polyethylene glycol (PEG), povidone, hydroxypropyl cellulose (HPMC), Mg stearate, Ca stearate, stearic acid, sodium stearate fumarate, and silicon dioxide. In some embodiments, the compositions are in powder form suitable for compaction, tableting, and/or oral administration.

In some embodiments, the solid compositions of the invention include a therapeutically effective dose of a non-hydrate crystalline form of a lactic acid salt of the compound of formula I (e.g., Form A). A therapeutically effective dose refers to that amount of lactic acid salt of the compound of formula I sufficient to result in amelioration of symptoms of a given disorder. The solid pharmaceutical compositions of the instant invention can be manufactured by methods well known in the art such as conventional granulating, mixing, dissolving, encapsulating, lyophilizing, emulsifying or levigating processes, among others. The solid compositions can be in the form of, for example, granules, powders, tablets, or capsules. The instant compositions can be formulated for various routes of administration, for example, by oral administration, by transmucosal administration, and subcutaneous administration.

In order to determine the amount of compound in a patient following administration, certain manipulative steps can be taken. Such a method is described in the U.S. Provisional Application Ser. No. 60/517,915, titled, "Methods of Treating Cancer and Related Methods" filed on Nov. 7, 2003, by Vora et al. incorporated by reference in its entirety herein.

Oral, buccal, and sublingual administration, powders, suspensions, granules, tablets, pills, capsules, gelcaps, and caplets are acceptable as solid dosage forms. These can be prepared, for example, by mixing a non-hydrate crystalline form of a lactic acid salt of the compound of formula I (e.g., Form A) with at least one additive or excipient such as a starch or other additive. Suitable additives or excipients are sucrose, lactose, cellulose sugar, mannitol, maltitol, dextran, sorbitol, starch, agar, alginates, chitins, chitosans, pectins, tragacanth gum, gum arabic, gelatins, collagens, casein, albumin, synthetic or semi-synthetic polymers or glycerides, methyl cellulose, hydroxypropylmethyl-cellulose, and/or polyvinylpyrrolidone. Optionally, oral dosage forms can contain other ingredients to aid in administration, such as an inactive diluent, or lubricants such as magnesium stearate, or preservatives such as paraben or sorbic acid, or anti-oxidants such as ascorbic acid, tocopherol or cysteine, a disintegrating agent, or chelating agents such as EDTA, binders, thickeners, buffers, sweeteners, flavoring agents or perfuming agents. Additionally, dyestuffs or pigments may be added for identification. Tablets and pills may be further treated with suitable coating materials known in the art, such as moisture protective, enteric, or sustained release coatings.

In some embodiments, the compositions are supplied in a powder form in a storage container such as a vial In some embodiments, the vial is closed and in other embodiments the vial can be evacuated with an inert gas and stoppered.

Besides those representative dosage forms described above, pharmaceutically acceptable excipients and carriers are generally known to those skilled in the art and are thus included in the instant invention. Such excipients and carriers are described, for example, in "Remingtons Pharmaceutical Sciences" Mack Pub. Co., New Jersey (1991), which is incorporated herein by reference.

The formulations of the invention may be designed for to be short-acting, fast-releasing, long-acting, and sustained-releasing as described below. Thus, the pharmaceutical formulations may also be formulated for controlled release or for slow release.

The instant compositions may also comprise, for example, micelles or liposomes, or some other encapsulated form, or may be administered in an extended release form to provide a prolonged storage and/or delivery effect. Therefore, the pharmaceutical formulations may be compressed into pellets or cylinders and implanted intramuscularly or subcutaneously as depot injections or as implants such as stents. Such implants may employ known inert materials such as silicones and biodegradable polymers.

Specific dosages may be adjusted depending on conditions of disease, the age, body weight, general health conditions, sex, and diet of the subject, dose intervals, administration routes, excretion rate, and combinations of drugs. Any of the above dosage forms containing effective amounts are well within the bounds of routine experimentation and therefore, well within the scope of the instant invention.

A therapeutically effective dose may vary depending upon the route of administration and dosage form. The non-hydrate crystalline form of a lactic acid salt of the compound of Formula I (e.g., Form A) can be provided in a formulation that exhibits a high therapeutic index. The therapeutic index is typically understood to be the dose ratio between toxic and therapeutic effects which can be expressed as the ratio between $LD_{50}$ and $ED_{50}$. The $LD_{50}$ is the dose lethal to 50% of the population and the $ED_{50}$ is the dose therapeutically effective in 50% of the population. The $LD_{50}$ and $ED_{50}$ are determined by standard pharmaceutical procedures in animal cell cultures or experimental animals.

"Treating" within the context of the instant invention, means an alleviation of symptoms associated with a disorder or disease, or halt of further progression or worsening of those symptoms, or prevention or prophylaxis of the disease or disorder. For example, within the context of treating patients in need of an inhibitor of VEGF-RTK, successful treatment may include a reduction in the proliferation of capillaries feeding a tumor or diseased tissue, an alleviation of symptoms related to a cancerous growth or tumor, proliferation of capillaries, or diseased tissue, a halting in capillary proliferation, or a halting in the progression of a disease such as cancer or in the growth of cancerous cells. Treatment may also include administering the solid pharmaceutical formulations of the present invention in combination with other therapies. For example, the crystalline forms and solid pharmaceutical formulations of the present invention may be administered before, during, or after surgical procedure and/or radiation therapy. The compounds of the invention can also be administered in conjunction with other anti-cancer drugs including those used in antisense and gene therapy.

A "subject" or "patient" is meant to describe a human or vertebrate animal including a dog, cat, marmoset, horse, cow, pig, sheep, goat, elephant, giraffe, chicken, lion, monkey, owl, rat, squirrel, slender loris, mouse, hamster, chinchilla, ferret, rat, guinea pig, gerbil, rabbit and sugar glider.

In one embodiment of the invention is a method of treating a patient in need of an inhibitor of vascular endothelial growth factor receptor tyrosine kinase which includes administering an effective amount of a solid pharmaceutical formulation containing a non-hydrate crystalline form of a lactic acid salt of the compound of formula I, such as the crystalline form which is Form A, to a patient in need thereof. Preferably, the formulation is a powder formulation, suitable for oral administration.

In one embodiment of the invention is a method for inhibiting tumor growth in a patient includes administering an effective amount of a solid pharmaceutical formulation containing a non-hydrate crystalline form of a lactic acid salt of the compound of formula such as the crystalline form which is Form A, to a patient having a tumor. Preferably, the formulation is a powder formulation, suitable for oral administration.

In one embodiment of the invention is a method for inhibiting the proliferation of capillaries in a patient which includes administering an effective amount of a solid pharmaceutical formulation containing a non-hydrate crystalline form of a lactic acid salt of the compound of formula I, such as the crystalline form which is Form A, according to a patient in need. Preferably, the formulation is a powder formulation, suitable for oral administration.

In one embodiment of the invention is a method of preparing solid pharmaceutical formulations which includes mixing a non-hydrate crystalline form of a lactic acid salt of the compound of formula I, such as the crystalline form which is Form A, with a pharmaceutically acceptable carrier. Preferably, the formulation is a powder formulation, suitable for oral administration.

In further embodiments, the present invention provides a method of treating a patient with a solid formulation containing a non-hydrate crystalline form of a lactic acid salt of the compound of formula I, by oral administration of the formulation to the patient. In some embodiments, the non-hydrate crystalline form of a lactic acid salt of the compound of formula I is a mono-lactic acid salt. In some embodiments, the non-hydrate crystalline form of a lactic acid salt of the compound of formula I corresponds to Form A. In some embodiments, the solid formulation is in the form of a powder. In some embodiments, the solid formulation can be prepared by compaction or other treatment of a powder containing the non-hydrate crystalline form of a lactic acid salt of the compound of formula I. In further embodiments, the solid formulation of can be prepared in the form of a pill, tablet, capsule, or a caplet.

In some embodiments, the crystalline form of the lactic acid salt of the compound of formula I which is present in the solid formulation remains substantially a non-hydrate crystalline form, such as Form A, under ambient conditions for a period greater than about 36 hours, greater than about 1 week, greater than about 1 month, greater than about 6 months, or greater than about 1 year.

According to embodiments of methods of treating a patient, the patient can be a cancer patient. In some embodiments, the patient is diagnosed with multiple myeloma (MM), acute myelogenous leukemia (AML), prostate cancer, breast cancer, colon cancer, or melanoma. In further embodiments, the patient is a refractory patient, such as a patient showing resistance to preexisting therapeutics or treatment regimens, including prescribed/clinical dosing schedules. In some embodiments, the patient can be treated with a dose that is less than the maximum tolerated dose (MTD), such as a dose of about 0.25 to 30 mg/kg of the lactic acid salt of the compound of formula I. "MTD," as used herein, refers to the highest dose during diagnostic, prophylactic or therapeutic procedures that a body can tolerate without substantial injury. The MTD is reviewed in context of alteration of physiological function which would be predicted to alter a patients life span. Factors include: no more than 10% decrease in body weight gain relative to controls, target organ toxicity, and significant alterations in clinical pathological parameters.

In some embodiments, the solid formulations of the invention are solids at the time of administration to a patient which would include, for example, direct ingestion (e.g. via the mouth) of a pill, tablet, capsule, caplet or the like, as opposed to, for example, ingestion of a solution or suspension made by mixing a solid formulation with liquid media prior to ingestion.

In further embodiments, each unit dose containing a solid formulation of the invention is sufficient to provide at least one of:

(a) a $C_{max}$ of about 20 to 4000 ng/mL of the compound of Formula I in a subject's plasma or a $C_{max}$ of about 40 to 8000 ng/mL of the compound in the subject's blood when it is administered to the subject;

(b) about 10 to 2,000 ng/mL of the compound in a subject's plasma 24 hours after administration or about 20 to 4,000 ng/mL of the compound in the subject's blood 24 hours after administration to the subject, or (c) an AUC of about 500 to 60,000 ng*h/mL of the compound in a subject's plasma or about 750 to 120,000 ng*h/mL of the compound in the subject's blood when it is administered to the subject.

In further embodiments, each unit dose a solid formulation of the invention is sufficient to provide at least one of:

(a) a $C_{max}$ of about 50 to 500 ng/mL of the compound in the subject's plasma or a $C_{max}$ of about 100 to 1000 ng/mL of the compound in the subject's blood;

(b) about 20 to 1,000 ng/mL of the compound in the subject's plasma 24 hours after administration or about 40 to 2,000 ng/mL of the compound in the subject's blood 24 hours after administration; or (c) an AUC of about 1,000 to 30,000 ng*h/mL of the compound in the subject's plasma or about 1,500 to 60,000 ng*h/mL of the compound in the subject's blood.

In further embodiments, each unit dose containing a solid formulation of the invention is sufficient to provide at least one of:

(a) a $C_{max}$ of about 50 to 250 ng/mL of the compound in the subject's plasma or a $C_{max}$ of about 100 to 500 ng/mL of the compound in the subject's blood;

(b) about 40 to 500 ng/mL of the compound in the subject's plasma 24 hours after administration or about 80 to 1,000 ng/mL of the compound in the subject's blood 24 hours after administration; or (c) an AUC of about 2,000 to 15,000 ng*h/mL of the compound in the subject's plasma or about 3,000 to 30,000 ng*h/mL of the compound in the subject's blood.

In further embodiments, each unit dose containing a solid formulation of the invention is sufficient to provide at least one of:

(a) a $C_{max}$ of about 75 to 150 ng/mL of the compound in the subject's plasma or a $C_{max}$ of about 150 to 300 ng/mL of the compound in the subject's blood; or (b) about 40 to 250 ng/mL of the compound in the subject's plasma 24 hours after administration or about 80 to 500 ng/mL of the compound in the subject's blood 24 hours after administration.

In further embodiments, each unit dose containing a solid formulation of the invention is sufficient to provide a $C_{max}$ of about 100 to 2000 ng/mL of the compound in the subject's plasma or a $C_{max}$ of about 200 to 4000 ng/mL of the compound in the subject's blood.

In further embodiments, each unit dose containing a formulation of the invention is sufficient to provide a $C_{max}$ of 100 to 1000 ng/mL of the compound in the subject's plasma or a $C_{max}$ of about 200 to 2000 ng/mL of the compound in the subject's blood In order that the invention disclosed herein may be more efficiently understood, examples are provided below. It should be understood that these examples are for illustrative purposes only and are not to be construed as limiting the invention in any manner.

Hydrates: Forms B, C, D, and E

In a second aspect, the present invention provides, inter alia, a crystalline hydrate of a lactic acid salt of a compound of Formula I:

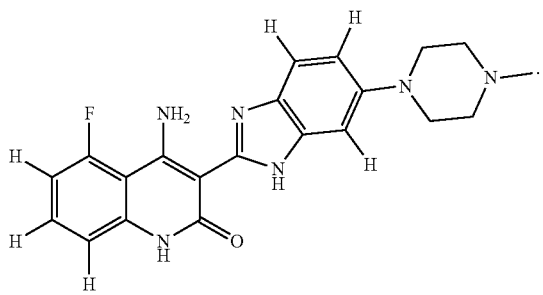

I

In some embodiments of the hydrates of the present invention, the molar ratio of the hydrate water to the lactic acid salt of the compound of Formula I is about 1 or about 6.

In some embodiments, a hydrate of the present invention is a monohydrate or hexahydrate.

In some embodiments of the monohydrates of the present invention, the molar ratio of the hydrate water to the lactic acid salt of the compound of Formula I is about 1.

In some embodiments of the hexahydrates of the present invention, the molar ratio of the hydrate water to the lactic acid salt of the compound of Formula I is from about 4 to about 6.

In some embodiments of the hexahydrates of the present invention, the molar ratio of the hydrate water to the lactic acid salt of the compound of Formula I is from about 5 to about 6.

In some embodiments of the hexahydrates of the present invention, the molar ratio of the hydrate water to the lactic acid salt of the compound of Formula I is about 6.

Hydrated lactic acid salts can further include mono- and di-acid salt forms, and the like. Preferably, the lactic acid salt is a mono-lactic acid salt of the compound of formula I. Di-lactic acid salts (i.e., bis-lactic acid salts), tri-lactic acid salts (i.e., tris-lactic acid salts) and intermediate and higher orders of salts are also encompassed and can be formed by the combination of greater than one equivalent of lactic acid with the compound of formula I according to routine methods of preparing acid addition salts. In some embodiments of the hydrates of the present invention, the lactic acid salt of the compound of Formula I is a mono-lactic acid salt.

In some embodiments, the crystalline hydrate form of the lactic acid salt of the compound of formula I is crystalline Form B, Form C, Form D or Form E.

Forms B, C, D and E can be characterized by any one or more solid state techniques such as X-ray powder diffraction (XRPD), single crystal X-ray diffraction, differential scanning calorimetry (DSC), dynamic vapor sorption (DVS), crystal morphology, solid state nuclear magnetic resonance, Raman scattering, infrared (IR) spectroscopy, thermogravimetry (TG), thermogravimetry (TG) coupled with Fourier-Transform Infrared (FTIR) spectroscopy (TG-FTIR) and the like. In some embodiments, forms B, C, D and E can be identified by their XRPD pattern. In some embodiments, forms B, C, D and E can be identified by its DSC thermogram.

In some embodiments, forms B, C, D and E can be identified by crystal morphology. In some embodiments, forms B, C, D and E can be identified by its DVS cycle. Other techniques, alone or in combination with the ones recited herein, can also be used to identify forms B, C, D and E.

Form B

Figure 6:
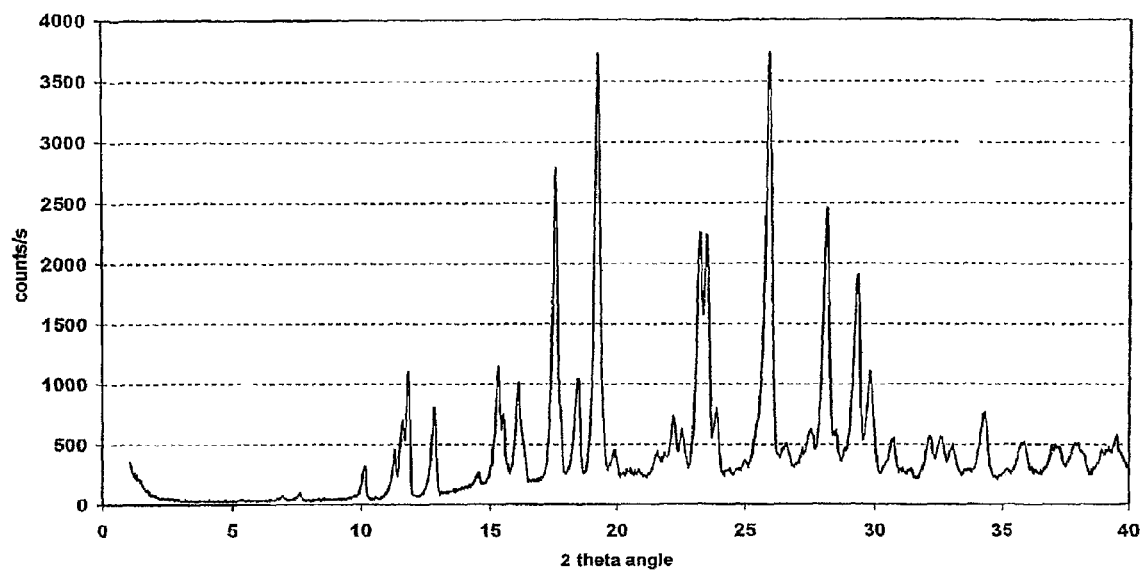
FIG. 6 shows an XRPD pattern characteristic of Form B.

In some embodiments of the present invention, the crystalline hydrate form of the lactic acid salt of the compound of formula I is crystalline Form B. Crystalline Form B is characterized as a crystalline monohydrate of a lactic acid salt of the compound of formula I. In some embodiments of Form B, the lactic acid salt is a mono-lactic acid salt. Form B can be identified by its X-ray powder diffraction (XRPD) pattern which is provided in FIG. 6. In some embodiments, the crystalline Form B of the invention has an XRPD pattern substantially as shown in FIG. 6 (two-theta values provided in Example 10), where the term "substantially" in this instance indicates that two-theta values for individual peaks can vary about ±0.2°. The relative intensities of the peaks can also vary, depending upon the sample preparation technique, the sample mounting procedure and the particular instrument employed. Powder X-ray diffraction two-theta data consistent with Form B is provided in Example 10 below. As discussed above, many factors can affect the 2-theta values. Therefore, the peak assignments listed in Example 10 can vary by plus or minus about 0.2°.

The crystalline Form B of the invention can be further recognized by its differential scanning calorimetry (DSC) thermogram which has a characteristic endotherm at about 155° C. (peak maximum) with a ΔH~100 J/g. In some embodiments, the crystalline Form B of the invention has a DSC trace substantially having the endotherm substantially as described above, it being understood that the term "substantially" in this instance indicates that features such as endotherms, exotherms, baseline shifts, etc. can vary about ±4° C. For DSC, it is known that the temperatures observed will depend upon the rate of temperature change as well as sample preparation technique and the particular instrument employed. Thus, the values reported herein relating to DSC thermograms can vary by plus or minus about 4° C.

TG-FTIR analysis of Form B samples revealed a weight loss of about 3.7%. At a heating rate of 10 K/min the weight loss started just above ambient temperature and the 3.7% of water were completely removed near 150° C. Further analysis of the water content by Karl Fischer titration (also determined to be about 3.7%) confirms that the weight loss in the TG-FTIR is essentially corresponding to the water content. Although not wishing to be bound by any particular theory, Form B is characterized as a monohydrate, since the theoretically expected water content of a monohydrate of the mono-lactic acid salt of the compound of formula I is 3.7%.

Crystalline Form B can be prepared by any of numerous methods in the art. In some embodiments, Form B can be prepared by suspending Form A in a solution which comprises water and an organic solvent at a temperature of about 20° C. to about 60° C., wherein the organic solvent comprises an alcohol, a ketone, an organic nitrile, or mixture thereof, and wherein the water is present in the solution in an amount of about 5% to about 20% by volume.

An example method for preparing Form B is as follows:
(a) suspending Form A in a solution which comprises water and an organic solvent at a temperature of about 20° C. to about 60° C. for a period of time sufficient to afford the Form B; and
(b) and isolating Form B.

Suitable organic solvents include those in which the newly-formed Form B is not readily soluble so that the Form B can be isolated. Example organic solvents include alcohols (e.g., methanol, ethanol, ispropanol, glycols, etc.), ketones (e.g., acetone, methylethyl ketone, etc.) and nitriles (e.g., acetonitrile, propionitril, etc.), mixtures thereof, and the like. In some embodiments, the organic solvent comprises one or more of ethanol, acetone, and methyl ethyl ketone. In some embodiments, the organic solvent contains an alcohol such as methanol or ethanol. In some embodiments, the organic solvent contains a ketone such as acetone or methylethyl ketone. In some embodiments, the organic solvent contains a nitrile such as acetonitrile.

The water content in the solution will typically be less than about 20% by volume. In some embodiments, the water is present in the solution in an amount of about 5% to about 20% by volume. In some embodiments, the water is present in the solution in an amount of about 5% to about 10% by volume. In some embodiments, the water is present in the solution in an amount of about 10% to about 20% by volume.

The suspending is carried out at any suitable temperature to afford Form B such as a temperature of about 20° C. to about 60° C. In some embodiments, the suspending is carried out at a temperature of about 20° C. to about 30° C. In some embodiments, the suspending is carried out at a temperature of about 23° C. In some embodiments, the suspending is carried out at a temperature of about 40° C. to about 60° C. In some embodiments, the suspending is carried out at a temperature of about 50° C.

The suspending can be carried out for a period of time sufficient to afford Form B. In some embodiments, the suspending is carried out for about 20 hours to about 100 hours. In some embodiments, the suspending is carried out for about 20 hours. In some embodiments, the suspending is carried out for about 50 hours. In some embodiments, the suspending is carried out for about 100 hours.

In some embodiments, the water is present in the solution in an amount of about 10% by volume; the organic solvent comprises one or more of ethanol, acetone, and methyl ethyl ketone; and the suspending is carried out at a temperature of about 20° C. to about 30° C. In some embodiments, the water is present in the solution in an amount of about 5% by volume; the organic solvent comprises acetonitrile; and the suspending is carried out at a temperature of about 40° C. to about 60° C.

The starting concentration of Form A in the solution can vary. It is postulated that the water in the solution is responsible for the formation of Form B (which is a hydrate). In some embodiments, the concentration of Form A in the solution is about 100 to about 140 or about 120 mg/mL.

It should be recognized that the Form A in the suspending step can be generated according to a variety of methods described herein. In some embodiments, the generation of Form A and suspending of Form A in the solution to afford Form B can be carried out in one process.

Form C

In some embodiments of the present invention, the crystalline hydrate form of the lactic acid salt of the compound of formula I is crystalline Form C. Crystalline Form C is characterized as a crystalline hydrate of a lactic acid salt of the compound of formula I, wherein the hydrate content lies between the mono- and the sesquihydrate. In some embodiments of Form C, the lactic acid salt is a mono-lactic acid salt.

Figure 7:
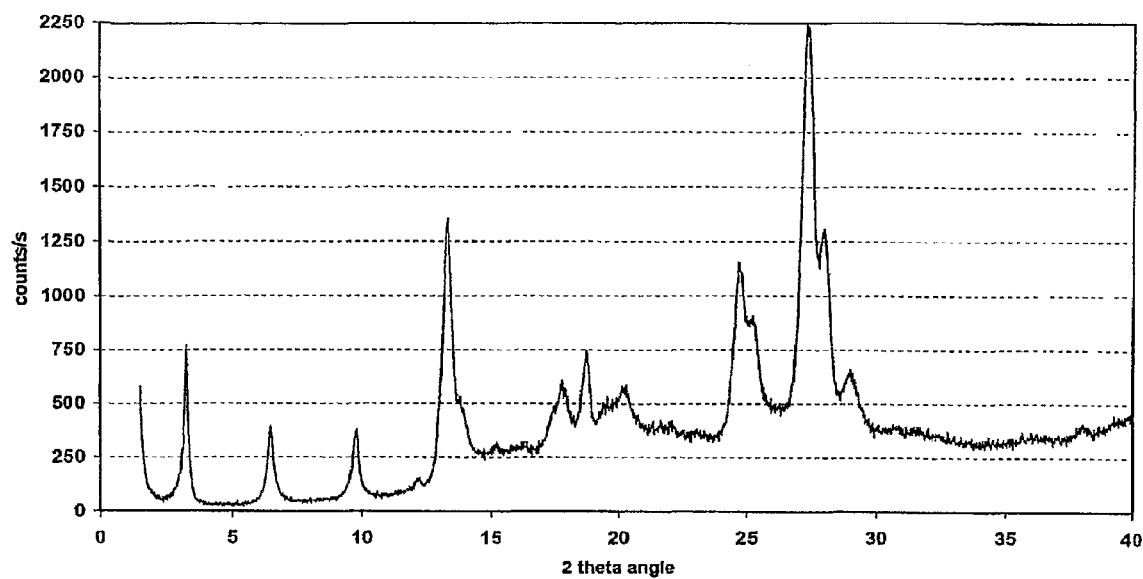
FIG. 7 shows an XRPD pattern characteristic of Form C.

Form C can be identified by its X-ray powder diffraction (XRPD) pattern as provided in FIG. 7. Relatively prominent two-theta peaks were found at from about 3.2 to about 3.6, at from about 6.5 to about 7.1, at from about 9.8 to about 10.6, at from about 13.3 to about 14.1, at from about 17.6 to about 17.8, at about 18.8, at about 20.2, at from about 24.7 to about 24.9, at about 27.3 to about 27.5, at about 28.0, and at from about 29.0 to about 29.3°. In some embodiments, the crystalline Form C of the invention has an XRPD pattern substantially as shown in FIG. 7 (two-theta values provided in Example 11), where the term "substantially" in this instance indicates that two-theta values for individual peaks can vary about ±0.2°. The relative intensities of the peaks can also vary, depending upon the sample preparation technique, the sample mounting procedure and the particular instrument employed. Powder X-ray diffraction two-theta data consistent with Form C is provided in Example 11 below. As discussed above, many factors can affect the 2-theta values. Therefore, the peak assignments listed in Example 11 can vary by plus or minus about 0.2°.

The XRPD patterns of Form C as provided in FIG. 7 can vary slightly, suggesting that Form C can adsorb variable amounts of water. A higher water content is likely to lead to a slight lattice expansion (larger d-spacings) with a concurrent shift of the XRPD peaks to smaller angles.

Crystalline Form C of the invention can be further recognized by its differential scanning calorimetry (DSC) thermogram which shows a very small exothermic signal between about 50° C. and about 80° C. which is attributed to crystallization of a small amount of residual amorphous form. Between about 80 and about 140° C. several small endothermic signals (at about 109° C., 115° C. and 127° C.) and one small exothermic signal (at about 121° C.) suggest that multiple phase transitions are taking place. These effects are followed by a strong endothermic signal (ΔH=35 J/g) with a peak near about 150° C. In some embodiments, the crystalline Form C of the invention has a DSC trace having substantially the values described above, where the term "substantially" in this instance indicates that features such as endotherms, exotherms, baseline shifts, etc. can vary about 4° C. For DSC, it is known that the temperatures observed will depend upon the rate of temperature change as well as sample preparation technique and the particular instrument employed. Thus, the values reported herein relating to DSC thermograms can vary by plus or minus about 4° C.

TG-FTIR analysis of Form C samples revealed a weight loss of about 4.6%, which corresponds to an amount that lies between the mono- and the sesquihydrate.

Investigation of Form C in a DVS experiment, such as provided in Example 11, reveals a water content of about 6.5% at the start of the measurement and about 4.8% at the end of the measurement. However, the Raman spectrum of the recovered sample corresponds substantially to Form C. Although not wishing to be bound by any particular theory, the reason for the irreversibility found for Form C is believed to be due to some remaining amorphous material that is crystallizing during the measurement. Then the water content of Form C would indeed be about 4.6%, as found for the sample used in the DSC experiment as shown herein. This amount of water would correspond to 4/3 water molecules per formula unit (i.e., sesquihydrate).

Crystalline Form C can be prepared by any of numerous methods in the art. In some embodiments, Form C can be prepared by diffusing organic solvent vapor into an aqueous solution of the lactic acid salt of the compound of Formula I at a temperature of about 0° C. to about 10° C. In some embodiments, Form C can be prepared by contacting the amorphous form of the lactic acid salt of the compound of Formula I with a relative humidity of from about 50% to about 75% at a temperature of from about 40° C. to about 80° C.

An example method for preparing Form C is as follows:

(a) diffusing organic solvent vapor into an aqueous solution of said lactic acid salt of said compound of Formula I at a temperature of about 0° C. to about 10° C. for a period of time sufficient to afford the Form C; and (b) and isolating Form C.

Suitable organic solvents include those in which the newly-formed Form C is not readily soluble so that the Form C can be isolated. Example organic solvents include alcohols (e.g., methanol, ethanol, ispropanol, glycols, etc.), ketones (e.g., acetone, methylethyl ketone, etc.) and nitriles (e.g., acetonitrile, propionitril, etc.), mixtures thereof, and the like. In some embodiments, the organic solvent contains an organic nitrile such as acetonitrile.

In some embodiments, more organic solvent (whose vapor was used in the diffusing) can be optionally added to the mixture in step (a) after Form C is formed at a temperature of about 0° C. to about 10° C.

The diffusing can be carried out at a suitable temperature such as about 0° C. to about 10° C. to afford Form C. In some embodiments, the diffusing is carried out at a temperature of about 5° C.

The diffusing is carried out for a period of time sufficient to afford Form C. In some embodiments, the diffusing is carried out for about 20 hours to about 100 hours.

The concentration of the lactic acid salt of the compound of Formula I in solution can vary. In some embodiments, concentration is about 100 mg/mL or greater. In some embodiments, concentration is about 200 mg/mL or greater. In some embodiments, concentration is about 300 mg/mL or greater. In some embodiments, concentration is from about 300 mg/mL to about 400 mg/mL.

Another example method for preparing Form C is carried out by:

contacting the amorphous form of the lactic acid salt of the compound of Formula I with a relative humidity of from about 50% to about 75% at a temperature of from about 40° C. to about 80° C. for a period of time sufficient to afford the Form C.

The amorphous form can be prepared by the method described herein in Example 8.

The contacting can be carried out at a temperature of from about 40° C. to about 80° C. In some embodiments, the temperature is from about 60° C. to about 80° C. In some embodiments, the temperature is from about 70° C. to about 80° C. In some embodiments, the temperature is about 80° C. In some embodiments, the temperature is from about 40° C. to about 60° C. In some embodiments, the temperature is from about 40° C. to about 50° C. In some embodiments, the temperature is about 50° C.

The contacting can be carried out for a period of time sufficient to afford the Form C. In some embodiments, the contacting lasts about 6 hours or longer. In some embodiments, the contacting lasts about 20 hours or longer. In some embodiments, the contacting lasts about 1 day or longer. In some embodiments, the contacting lasts about 2 days or longer. In some embodiments, the contacting lasts about 3 days or longer. In some embodiments, the contacting lasts about 4 days or longer. Although not wishing to be bound by any particular theory, it is postulated that during the contacting the higher the temperature is, a relatively shorter the time period is needed for the formation of Form C.

Figure 5:
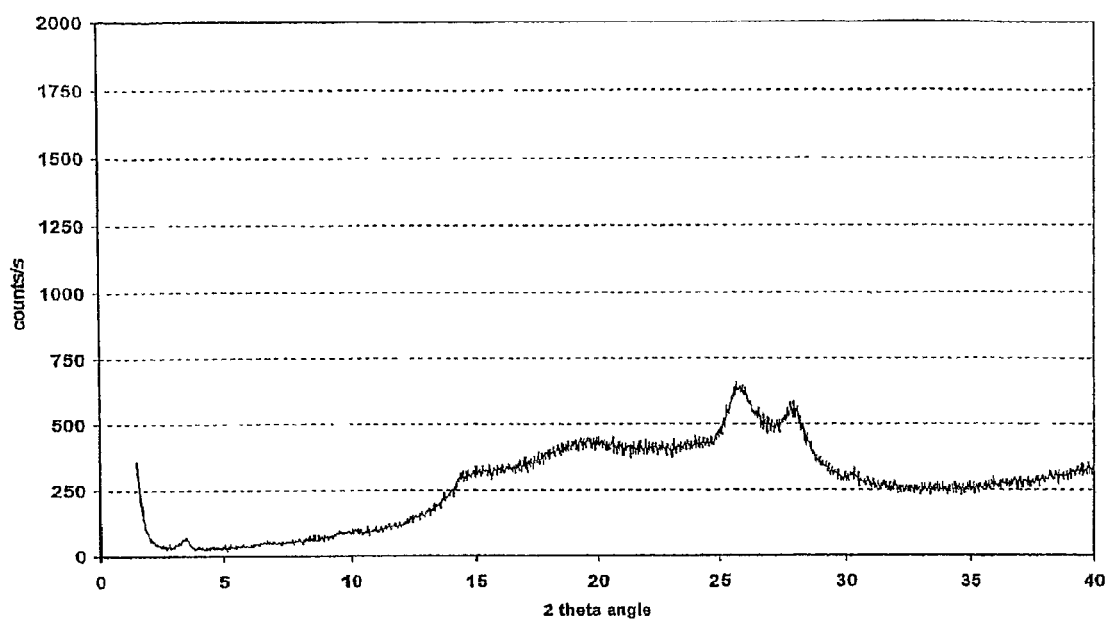
FIG. 5 shows an XRPD pattern characteristic of the amorphous form.

As used herein, "the amorphous form" refers to the anhydrous, non-crystalline form of a lactic acid salt of the compound of formula I which can be prepared, for example, by the lyophilization method described in Example 8. The amorphous form samples can be characterized by XRPD patterns and DSC (as shown in Examples 8 and 9). Typical example XRPD patterns of the amorphous form is provided in FIG. 5.

Form D

In some embodiments of the present invention, the crystalline hydrate form of a lactic acid salt of the compound of formula I is crystalline Form D. In some embodiments of Form D, the lactic acid salt is a mono-lactic acid salt.

Figure 8:
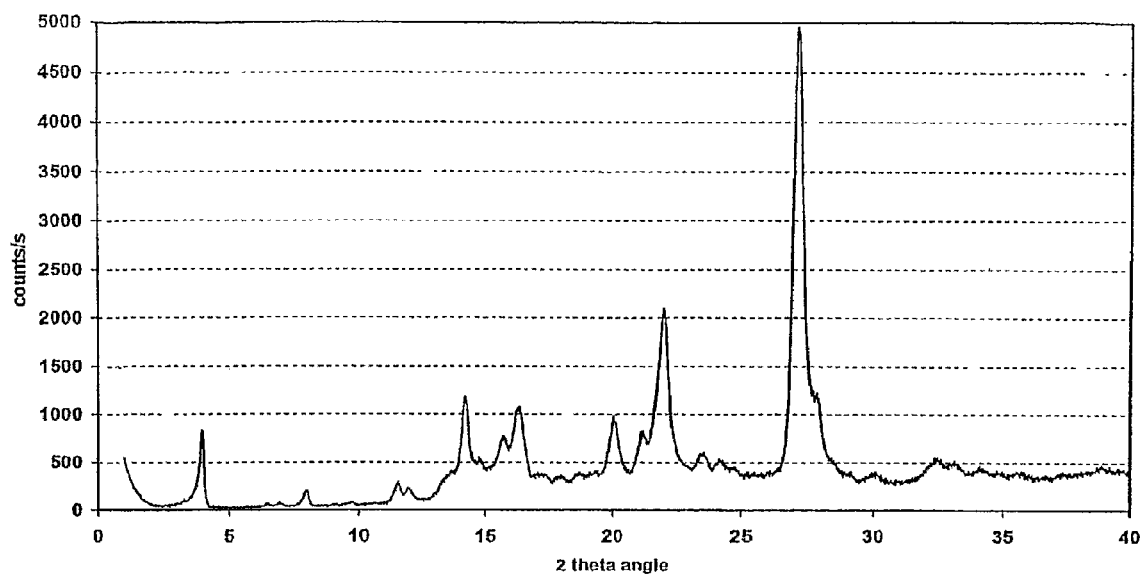
FIG. 8 shows an XRPD pattern characteristic of Form D.

Form D can be identified by its X-ray powder diffraction (XRPD) pattern, one example of which is provided in FIG. 8. Relatively prominent two-theta peaks were at about 4.0, about 8.0, about 11.5, about 12.0, about 14.3, about 15.8, about 16.4, about 20.1, about 21.2, about 22.0, about 23.6, about 27.2 and about 27.9 degrees. In some embodiments, the crystalline Font; D of the invention has an XRPD pattern substantially as shown in FIG. 8 (two-theta values provided in Example 12), where the term "substantially" in this instance indicates that two-theta values for individual peaks can vary about ±0.2°. The relative intensities of the peaks can also vary, depending upon the sample preparation technique, the sample mounting procedure and the particular instrument employed. Powder X-ray diffraction two-theta data consistent with Form D is provided in Example 12 below. As discussed above, many factors can affect the 2-theta values. Therefore, the peak assignments listed in Example 12 can vary by plus or minus about 0.2°.

The crystalline Form D of the invention can be further recognized by its differential scanning calorimetry (DSC) thermogram which shows multiple transitions with an endothermic signal near about 75° C. ($\Delta H\sim 13$ J/g), followed by a second endothermic signal near about 147° C. ($\Delta H\sim 27$ J/g) and an exothermic signal near about 163° C., and a further endothermic signal near about 191° C. ($\Delta H\sim 31$ J/g). In some embodiments, the crystalline Form D of the invention has a DSC trace substantially as described above, where the term "substantially" in this instance indicates that features such as endotherms, exotherms, baseline shifts, etc. can vary about ±4° C. For DSC, it is known that the temperatures observed will depend upon the rate of temperature change as well as sample preparation technique and the particular instrument employed. Thus, the values reported herein relating to DSC thermograms can vary by plus or minus about 4° C.

When a freshly-prepared sample of Form D (see preparation in Example 12) was analyzed by TG-FTIR, Karl Fischer titration, and DVS data are provided in Example 12. TG-FTIR and Karl Fischer titration indicated a weight loss attributed to water. Thus Form D is a hydrate such as a monohydrate.

Crystalline Form D can be prepared by any of numerous methods in the art. In some embodiments, Form D can be prepared by contacting the amorphous form of the lactic acid salt of the compound of Formula I with an inert atmosphere having a relative humidity of about 30% or less at a temperature of from about 80° C. to about 150° C.

The amorphous form can be prepared by the method described herein in Example 8. The contacting is carried out at a relative humidity of about 30% or less. In some embodiments, the relative humidity of about 20% or less. In some embodiments, the relative humidity of about 10% or less. In some embodiments, the relative humidity of about 5% or less. The contacting can be carried out in an inert atmosphere which is substantially free of water.

The contacting can further be carried out at a temperature of from about 80° C. to about 150° C. In some embodiments, the temperature is from about 100° C. to about 120° C. In some embodiments, the temperature is from about 110° C. to about 120° C. In some embodiments, the temperature is about 110° C. In some embodiments, the temperature is about 120° C.

The contacting is carried out for a period of time sufficient to afford the Form C. In some embodiments, the contacting lasts about 4 hours or longer. In some embodiments, the contacting lasts about 5 hours or longer. In some embodiments, the contacting lasts about 5 hours or longer.

Form E

In some embodiments of the present invention, the crystalline hydrate form of a lactic acid salt of the compound of formula I is crystalline Form E. In some embodiments, crystalline Form E is characterized as a crystalline multihydrate, such as a hexahydrate of a lactic acid salt of the compound of formula I. In some embodiments of Form E, the lactic acid salt is a mono-lactic acid salt. In some embodiments of Form E, the molar ratio of hydrate-water content to the lactic acid salt is from about 4 to about 6. In some embodiments of Form E, the molar ratio of hydrate-water content to the lactic acid salt is from about 5 to about 6. In some embodiments of Form E, the molar ratio of hydrate-water content to the lactic acid salt is about 6.

Figure 9:
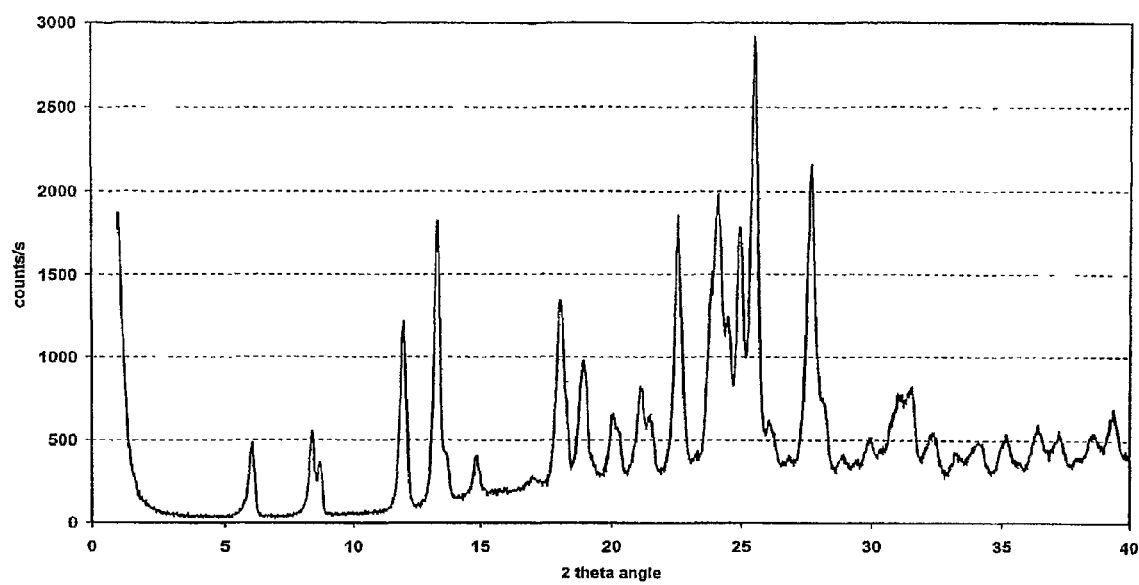
FIG. 9 shows an XRPD pattern characteristic of Form E.

Form E can be identified by its X-ray powder diffraction (XRPD) pattern, one example of which is provided in is provided in FIG. 9. Relatively prominent two-theta peaks were at about 6.1, about 8.4, about 8.7, about 12.1, about 13.4, about 14.9, about 18.1, about 19.0, about 20.1, about 21.1 about 21.5, about 22.6, about 24.1, about 24.5, about 25.0, about 25.5, about 27.7, about 30.1, and about 30.6 degrees. In some embodiments, the crystalline Form E of the invention has an XRPD pattern substantially as shown in FIG. 9 (two-theta values provided in Example 13), where the term "substantially" in this instance indicates that two-theta values for individual peaks can vary about ±0.2°. The relative intensities of the peaks can also vary, depending upon the sample preparation technique, the sample mounting procedure and the particular instrument employed. Powder X-ray diffraction two-theta data consistent with Form E is provided in Example 13 below. As discussed above, many factors can affect the 2-theta values. Therefore, the peak assignments listed in Example 13 can vary by plus or minus about 0.2°.

The crystalline Form E of the invention can be further recognized by its differential scanning calorimetry (DSC) thermogram which shows multiple transitions. The most prominent peak corresponds to an endothermic signal near about 76° C. ($\Delta H \sim 71$ J/g), which is followed by a small endothermic and a small exothermic signal at about 90° C. and about 93° C., respectively, and a stronger endothermic signal near about 128° C. ($\Delta H \sim 36$ J/g). In some embodiments, the crystalline Form E of the invention has a DSC trace substantially as described above, where the term "substantially" in this instance indicates that features such as endotherms, exotherms, baseline shifts, etc. can vary about ±4° C. For DSC, it is known that the temperatures observed will depend upon the rate of temperature change as well as sample preparation technique and the particular instrument employed. Thus, the values reported herein relating to DSC thermograms can vary by plus or minus about 4° C.

TG analysis of Form E revealed a weight loss of from about 9% to about 18%. At a heating rate of 10 K/min the weight loss started just above ambient temperature and the water was substantially removed near 160° C. Samples containing 18% weight loss (corresponding to hydrate water loss) suggests that Form E can be a hexahydrate Investigation of Form E in a DVS experiment, revealed that Foran E is relatively stable under humid conditions at a temperature of about 30° C. or lower.

Crystalline Form E can be prepared by any of numerous methods in the art. In some embodiments, Form E can be prepared by suspending Form A in water. In some embodiments, Form E can be prepared by seeding an aqueous solution of a lactic acid salt of said compound of Formula I with seed crystals of crystalline Form E, wherein the concentration of the solution is about 100 to about 200 mg/mL. In some embodiments, Form E can be prepared by crystallizing a lactic acid salt of said compound of Formula I in a solvent, wherein the solvent contains about 1 to about 10% by volume of water and about 90 to about 99% by volume of an organic solvent. In some embodiments, Form E can be prepared by suspending the amorphous form of a lactic acid salt of said compound of Formula I in a solvent, at a temperature of about 5° C., for a time of at least about 5 days, wherein the solvent comprises about 5% water by volume and about 95% acetonitrile by volume. In some embodiments, Form E can be prepared by adding an aqueous solution of said lactic acid salt of said compound of Formula I to a solvent at a temperature of about 2° C. to about 30° C., wherein the concentration of said aqueous solution is about 100 to about 300 mg/mL, and said solvent comprises ethyl acetate and tetrahydrofuran.

In some embodiments, the amount of Form A in the water is from about 100 mg/mL to about 400 mg/mL. In some embodiments, the amount is from about 100 mg/mL to about 200 mg/mL In some embodiments, the amount is from about 200 mg/mL to about 400 mg/mL. In some embodiments, the amount is from about 300 mg/mL to about 400 mg/mL. In some embodiments, the amount is from about 350 mg/mL to about 400 mg/mL.

In some embodiments, the suspending can be carried out at a temperature of about 20° C. to about 30° C. to afford Form E. In some embodiments, the suspending is carried out at a temperature of about 23° C.

The suspending is carried out for a period of time sufficient to afford Form E. In some embodiments, the suspending is carried out for about 15 hours to about 100 hours. In some embodiments, the suspending is carried out for about 24 hours. In some embodiments, the suspending is carried out for about 48 hours.

Another example method for preparing Form E is by seeding an aqueous solution of a lactic acid salt of said compound of Formula I with seed crystals of crystalline Form E, wherein the concentration of the solution is about 100 to about 200 mg/mL so that Form E is formed, then the Form E can be isolated.

In some embodiments, the concentration of the solution is from about 100 to about 200 mg/mL. In some embodiments, the concentration of the solution is from about 150 to about 200 mg/mL. In some embodiments, the concentration of the solution is from about 180 to about 200 mg/mL. In some embodiments, the concentration of the solution is about 200 mg/mL.

In some embodiments, the amount of seeding of crystalline Form E relative to the solution is from about 30 to about 50 mg/mL. In some embodiments, the amount of seeding crystalline Form E relative to the solution is from about 40 mg/mL.

A further example method for preparing Form E is by crystallizing a lactic acid salt of the compound of Formula I in a solvent, wherein the solvent contains about 1 to about 10% by volume of water and about 90 to about 99% by volume of an organic solvent. A typical procedure is as follows:

(a) mixing the compound of formula I with a solvent, wherein the solvent contains about 1 to about 10% by volume of water and about 90 to about 99% by volume of an organic solvent;

(b) heating the mixture;

(c) cooling the mixture; and (d) isolating Form E.

Suitable organic solvents include those in which (and/or in combination with water) Form E is not readily soluble at about a temperature of about 25° C. or lower so that the Form E can be isolated. Example organic solvents include an ether such as THF or an ester such as ethyl acetate. In some embodiments, the organic solvent contains THF. In some embodiments, the organic solvent contains ethyl acetate. In some embodiments, the amount of the compound of formula I in the solvent is from about 10 mg/mL to about 20 mg/mL. In some embodiments, the amount of the compound of formula I in the solvent is bout 15 mg/mL.

The mixture is heated to a temperature at which the compound of formula I is dissolved in the solvent. In some embodiments, the mixture is heated to a temperature near the boiling temperature of the solution to facilitate the dissolution of the compound of formula I.

The mixture (i.e., the solution) can be cooled down to a temperature to facilitate the precipitation of Form E from the mixture. In some embodiments, the mixture is cooled down to a temperature of about 25° C. or lower. In some embodiments, the mixture is cooled down to a temperature of about 15° C. or lower. In some embodiments, the mixture is cooled down to a temperature of about 10° C. or lower. In some embodiments, the mixture is cooled down to a temperature of about 5° C. or lower.

In some embodiments, the crystalline Form E can be obtained from the amorphous form (an example preparation of which is described in Example 9). One example method for preparing Form E is by suspending the amorphous form of a lactic acid salt of the compound of Formula I in a solvent, at a temperature of about 5° C., for a time of at least about 5 days, wherein the solvent comprises about 5% water by volume and about 95% acetonitrile by volume. Then the obtained Form E is isolated from the resulting suspension.

A further example method for preparing Form E is by adding an aqueous solution of the lactic acid salt of the compound of Formula I to a solvent at a temperature of about 2° C. to about 30° C., wherein the concentration of the aqueous solution is about 100 to about 300 mg/mL, and the solvent comprises ethyl acetate and tetrahydrofuran. One example procedure of such a method is as follows:

(a) adding an aqueous solution of the lactic acid salt of the compound of Formula I to a first solvent at a temperature of about 2° C. to about 30° C. to form a first mixture, wherein the concentration of the aqueous solution is about 100 to about 400 mg/mL;

(b) adding a second solvent to the first mixture at a temperature of about 2° C. to about 30° C. to form a second mixture;

(c) mixing the second mixture at a temperature of about 2° C. to about 30° C. for a period of time sufficient to form the Form E; and (d) isolating the Form E.

In some embodiments, the steps (a)-(c) are carried out at a temperature of about 2° C. to about 20° C. In some embodiments, the steps (a)-(c) are carried out at a temperature of about 2° C. to about 10° C. In some embodiments, the steps (a)-(c) are carried out at a temperature of about 2° C. to about 5° C.

In some embodiments, the concentration of the aqueous solution is about 200 to about 400 mg/mL. In some embodiments, the concentration of the aqueous solution is about 300 to about 400 mg/mL. In some embodiments, the concentration of the aqueous solution is about 300 to about 350 mg/mL.

In some embodiments, the first solvent comprises an ether such as THF. In some embodiments, the first solvent comprises THF. In some embodiments, the ratio by volume of the THF to the aqueous solution is about 5:1.

In some embodiments, the second solvent comprises an ester such as ethyl acetate. In some embodiments, the second solvent comprises ethyl acetate. In some embodiments, the ratio by volume of the ethyl acetate to the aqueous solution is about 10:1.

In some embodiments, the first solvent comprises THF, and the second solvent comprises ethyl acetate. In some further embodiments, the ratio of the aqueous solution to ethyl acetate to tetrahydrofuran is about 1:10:5 by volume in the second mixture.

The second mixture can be mixed for a time sufficient to form the Form E. In some embodiments, the second mixture is mixed for a time of about 4 hours or longer. In some embodiments, the second mixture is mixed for a time of about 10 hours or longer. In some embodiments, the second mixture is mixed for a time of about 20 hours or longer. In some embodiments, the second mixture is mixed for a time of about 25 hours or longer. In some embodiments, the second mixture is mixed for a time of about 26 hours or longer.

The methods for preparation of the crystalline hydrate forms (e.g., Form B, Form C, Form D and Form E) provided herein can result in substantially a single pure form (e.g., compositions containing less than about 20%, about 10%, about 5%, or about 3% by weight of impurities, amorphous material and/or other crystalline forms) as well as mixtures enriched in a single form (e.g., mixtures containing greater than about 50% by weight Form B relative to, for example, impurities, amorphous material or other crystalline forms). Accordingly, the present invention further provides compositions containing Form B, Form C, Form D or Form E. In some embodiments, at least about 50%, at least about 70%, at least about 80%, at least about 90%, at least about 95%, or at least about 99% by weight of total hydrate of lactic acid salt of the compound of formula I in a composition is present as Form B. In some embodiments, at least about 50%, at least about 70%, at least about 80%, at least about 90%, at least about 95%, or at least about 99% by weight of total hydrate of lactic acid salt of the compound of formula I in a composition is present as Form C. In some embodiments, at least about 50%, at least about 70%, at least about 80%, at least about 90%, at least about 95%, or at least about 99% by weight of total hydrate of lactic acid salt of the compound of formula I in a composition is present as Form D. In some embodiments, at least about 50%, at least about 70%, at least about 80%, at least about 90%, at least about 95%, or at least about 99% by weight of total hydrate of lactic acid salt of the compound of formula I in a composition is present as Form E. Amounts of different crystalline forms of in a composition can be determined by routine spectroscopic methods, such as X-ray powder diffraction, DSC, and the like.

The instant invention also provides for solid compositions (i.e., formulations) containing a crystalline hydrate form of a lactic acid salt of the compound of Formula I (e.g., Form B, Form C, Form D or Form E) with pharmaceutically acceptable carriers, excipients, binders, diluents or the like, to treat or ameliorate a variety of disorders related to the activity of VEGF-RTK, more particularly for example, angiogenesis associated with cancer. Excipients, diluents, binders, carriers and the like include, but are not limited to, microcrystalline cellulose, lactose, dibasic calcium phosphate, tribasic calcium phosphate, sodium starch glycolate (NaSG), crospovidone, crosscarmellose (CC), sodium lauryl sulfate (SLS), Tween, polyethylene glycol (PEG), povidone, hydroxypropyl cellulose (HPMC), Mg stearate, Ca stearate, stearic acid, sodium stearate fumarate, and silicon dioxide. In some embodiments, the compositions are in powder form suitable for compaction, tableting, and/or oral administration.

In some embodiments, the solid compositions of the invention include a therapeutically effective dose of a crystalline hydrate form of a lactic acid salt of the compound of formula I (e.g., Form B, Form C, Form D or Form E). A therapeutically effective dose refers to that amount of a hydrate of lactic acid salt of the compound of formula I sufficient to result in amelioration of symptoms of a given disorder. The solid pharmaceutical compositions of the instant invention can be manufactured by methods well known in the art such as conventional granulating, mixing, dissolving, encapsulating, lyophilizing, emulsifying or levigating processes, among others. The solid compositions can be in the form of, for example, granules, powders, tablets, or capsules. The instant compositions can be formulated for various routes of administration, for example, by oral administration, by transmucosal administration, and subcutaneous administration. In order to determine the amount of compound in a patient following administration, certain manipulative steps can be taken. Such a method is described in the U.S. Provisional Application Ser. No. 60/517,915, titled, "Methods of Treating Cancer and Related Methods" filed on Nov. 7, 2003, by Vora et al. incorporated by reference in its entirety herein.

Oral, buccal, and sublingual administration, powders, suspensions, granules, tablets, pills, capsules, gelcaps, and caplets are acceptable as solid dosage forms. These can be prepared, for example, by mixing a crystalline hydrate form of a lactic acid salt of the compound of formula I (e.g., Form B, Form C, Form D or Form E) with at least one additive or excipient such as a starch or other additive. Suitable additives or excipients are sucrose, lactose, cellulose sugar, mannitol, maltitol, dextran, sorbitol, starch, agar, alginates, chitins, chitosans, pectins, tragacanth gum, gum arabic, gelatins, collagens, casein, albumin, synthetic or semi-synthetic polymers or glycerides, methyl cellulose, hydroxypropylmethyl-cellulose, and/or polyvinylpyrrolidone. Optionally, oral dosage forms can contain other ingredients to aid in administration, such as an inactive diluent, or lubricants such as magnesium stearate, or preservatives such as paraben or sorbic acid, or anti-oxidants such as ascorbic acid, tocopherol or cysteine, a disintegrating agent, or chelating agents such as EDTA, binders, thickeners, buffers, sweeteners, flavoring agents or perfuming agents. Additionally, dyestuffs or pigments may be added for identification. Tablets and pills may be further treated with suitable coating materials known in the art, such as moisture protective, enteric, or sustained release coatings.

In some embodiments, the compositions containing a crystalline hydrate form of a lactic acid salt of the compound of formula I (e.g., Form B, Form C, Form D or Form E) are supplied in a powder form in a storage container such as a vial. In some embodiments, the vial is closed and in other embodiments the vial can be evacuated with an inert gas and stoppered.

Besides those representative dosage forms described above, pharmaceutically acceptable excipients and carriers are generally known to those skilled in the art and are thus included in the instant invention. Such excipients and carriers are described, for example, in "Remingtons Pharmaceutical Sciences" Mack Pub. Co., New Jersey (1991), which is incorporated herein by reference.

The formulations of the invention may be designed to be short-acting, fast-releasing, long-acting, and sustained-releasing as described below. Thus, the pharmaceutical formulations may also be formulated for controlled release or for slow release.

The instant compositions, which contain a crystalline hydrate form of a lactic acid salt of the compound of formula I (e.g., Form B, Form C, Form D or Form E), may also comprise, for example, micelles or liposomes, or some other encapsulated form, or may be administered in an extended release form to provide a prolonged storage and/or delivery effect. Therefore, the pharmaceutical formulations may be compressed into pellets or cylinders and implanted intramuscularly or subcutaneously as depot injections or as implants such as stents. Such implants may employ known inert materials such as silicones and biodegradable polymers.

Specific dosages may be adjusted depending on conditions of disease, the age, body weight, general health conditions, sex, and diet of the subject, dose intervals, administration routes, excretion rate, and combinations of drugs. Any of the above dosage forms containing effective amounts are well within the bounds of routine experimentation and therefore, well within the scope of the instant invention.

A therapeutically effective dose may vary depending upon the route of administration and dosage form. The crystalline hydrate form of a lactic acid salt of the compound of Formula I (e.g., Form B, Form C, Form D or Form E) can be provided in a formulation that exhibits a high therapeutic index. The therapeutic index is typically understood to be the dose ratio between toxic and therapeutic effects which can be expressed as the ratio between $LD_{50}$ and $ED_{50}$. The $LD_{50}$ is the dose lethal to 50% of the population and the $ED_{50}$ is the dose therapeutically effective in 50% of the population. The $LD_{50}$ and $ED_{50}$ are determined by standard pharmaceutical procedures in animal cell cultures or experimental animals.

One embodiment of the invention is a method of treating a patient in need of an inhibitor of vascular endothelial growth factor receptor tyrosine kinase which includes administering an effective amount of a solid pharmaceutical formulation, containing a crystalline hydrate form of a lactic acid salt of the compound of Formula I (e.g., Form B, Form C, Form D or Form E), to a patient in need thereof. Preferably, the formulation is a powder formulation, suitable for oral administration.

One embodiment of the invention is a method for inhibiting tumor growth in a patient includes administering an effective amount of a solid pharmaceutical formulation, containing a crystalline hydrate form of a lactic acid salt of the compound of Formula I (e.g., Form B, Form C, Form D or Form E), to a patient having a tumor. Preferably, the formulation is a powder formulation, suitable for oral administration.

One embodiment of the invention is a method for inhibiting the proliferation of capillaries in a patient which includes administering an effective amount of a solid pharmaceutical formulation, containing a crystalline hydrate form of a lactic acid salt of the compound of Formula I (e.g., Form B, Form C, Form D or Form E), according to a patient in need. Preferably, the formulation is a powder formulation, suitable for oral administration.

One embodiment of the invention is a method of preparing solid pharmaceutical formulations which includes mixing a crystalline hydrate form of a lactic acid salt of the compound of Formula I (e.g., Form B, Form C, Form D or Form E) with a pharmaceutically acceptable carrier. Preferably, the formulation is a powder formulation, suitable for oral administration.

In further embodiments, the present invention provides a method of treating a patient with a solid formulation containing a crystalline hydrate form of a lactic acid salt of the compound of Formula I (e.g., Form B, Form C, Form D or Form E), by oral administration of the formulation to the patient. In some embodiments, the crystalline hydrate form of a lactic acid salt of the compound of formula I is a mono-lactic acid salt. In some embodiments, the crystalline hydrate form of a lactic acid salt of the compound of formula I corresponds to Form B, Form C, Form D or Form E. In some embodiments, the crystalline hydrate form of a lactic acid salt of the compound of formula I corresponds to Form B. In some embodiments, the crystalline hydrate form of a lactic acid salt of the compound of formula I corresponds to Form C. In some embodiments, the crystalline hydrate form of a lactic acid salt of the compound of formula I corresponds to Form D. In some embodiments, the crystalline hydrate form of a lactic acid salt of the compound of formula I corresponds to Form E. In some embodiments, the solid formulation is in the form of a powder. In some embodiments, the solid formulation can be prepared by compaction or other treatment of a powder containing the crystalline hydrate form of a lactic acid salt of the compound of formula I. In further embodiments, the solid formulation of can be prepared in the form of a pill, tablet, capsule, or a caplet.

In some embodiments, the crystalline form of the lactic acid salt of the compound of formula I which is present in the solid formulation remains substantially a crystalline hydrate form, such as Form B, Form C, Form D or Form E, under ambient conditions for a period greater than about 36 hours, greater than about 1 week, greater than about 1 month, greater than about 6 months, or greater than about 1 year.

According to embodiments of methods of treating a patient, the patient can be a cancer patient. In some embodiments, the patient is diagnosed with multiple myeloma (MM), acute myelogenous leukemia (AML), prostate cancer, breast cancer, colon cancer, or melanoma. In further embodiments, the patient is a refractory patient, such as a patient showing resistance to preexisting therapeutics or treatment regimens, including prescribed/clinical dosing schedules. In some embodiments, the patient can be treated with a dose that is less than the maximum tolerated dose (MTD), such as a dose of about 0.25 to 30 mg/kg of the lactic acid salt of the compound of formula I. "MTD," as used herein, refers to the highest dose during diagnostic, prophylactic or therapeutic procedures that a body can tolerate without substantial injury. The MTD is reviewed in context of alteration of physiological function which would be predicted to alter a patients life span. Factors include: no more than 10% decrease in body weight gain relative to controls, target organ toxicity, and significant alterations in clinical pathological parameters.

In some embodiments, the solid formulations of the invention are solids at the time of administration to a patient which would include, for example, direct ingestion (e.g. via the mouth) of a pill, tablet, capsule, caplet or the like, as opposed to, for example, ingestion of a solution or suspension made by mixing a solid formulation with liquid media prior to ingestion.

In further embodiments, each unit dose containing a solid formulation of the invention is sufficient to provide at least one of:

(a) a $C_{max}$ of about 20 to 4000 ng/mL of the compound of Formula I in a subject's plasma or a $C_{max}$ of about 40 to 8000 ng/mL of the compound in the subject's blood when it is administered to the subject;

(b) about 10 to 2,000 ng/mL of the compound in a subject's plasma 24 hours after administration or about 20 to 4,000 ng/mL of the compound in the subject's blood 24 hours after administration to the subject, or (c) an AUC of about 500 to 60,000 ng*h/mL of the compound in a subject's plasma or about 750 to 120,000 ng*h/mL of the compound in the subject's blood when it is administered to the subject.

In further embodiments, each unit dose a solid formulation of the invention is sufficient to provide at least one of:

(a) a $C_{max}$ of about 50 to 500 ng/mL of the compound in the subject's plasma or a $C_{max}$ of about 100 to 1000 ng/mL of the compound in the subject's blood;

(b) about 20 to 1,000 ng/mL of the compound in the subject's plasma 24 hours after administration or about 40 to 2,000 ng/mL of the compound in the subject's blood 24 hours after administration; or (c) an AUC of about 1,000 to 30,000 ng*h/mL of the compound in the subject's plasma or about 1,500 to 60,000 ng*h/mL of the compound in the subject's blood.

In further embodiments, each unit dose containing a solid formulation of the invention is sufficient to provide at least one of:

(a) a $C_{max}$ of about 50 to 250 ng/mL of the compound in the subject's plasma or a $C_{max}$ of about 100 to 500 ng/mL of the compound in the subject's blood;

(b) about 40 to 500 ng/mL of the compound in the subject's plasma 24 hours after administration or about 80 to 1,000 ng/mL of the compound in the subject's blood 24 hours after administration; or (c) an AUC of about 2,000 to 15,000 ng*h/mL of the compound in the subject's plasma or about 3,000 to 30,000 ng*h/mL of the compound in the subject's blood.

In further embodiments, each unit dose containing a solid formulation of the invention is sufficient to provide at least one of:

(a) a $C_{max}$ of about 75 to 150 ng/mL of the compound in the subject's plasma or a $C_{max}$ of about 150 to 300 ng/mL of the compound in the subject's blood; or (b) about 40 to 250 ng/mL of the compound in the subject's plasma 24 hours after administration or about 80 to 500 ng/mL of the compound in the subject's blood 24 hours after administration.

In further embodiments, each unit dose containing a solid formulation of the invention is sufficient to provide a $C_{max}$ of about 100 to 2000 ng/mL of the compound in the subject's plasma or a $C_{max}$ of about 200 to 4000 ng/mL of the compound in the subject's blood.

In further embodiments, each unit dose containing a formulation of the invention is sufficient to provide a $C_{max}$ of 100 to 1000 ng/mL of the compound in the subject's plasma or a $C_{max}$ of about 200 to 2000 ng/mL of the compound in the subject's blood Form H and Form I Form H In a third aspect, the present invention provides, inter alia, a mesomorphic form (Form H) of a crystalline hydrate of a lactic acid salt of a compound of Formula I.

Form H is characterized as a solid-state forms which is partially crystalline. Such solid forms are designated herein as "mesophases" or "mesomorphic" forms. See e.g., B. Wunderlich, Macromol. Symp. 113, p. 51-65 (1997); and Thermochimica Acta 340-341 (1999).

Figure 12:
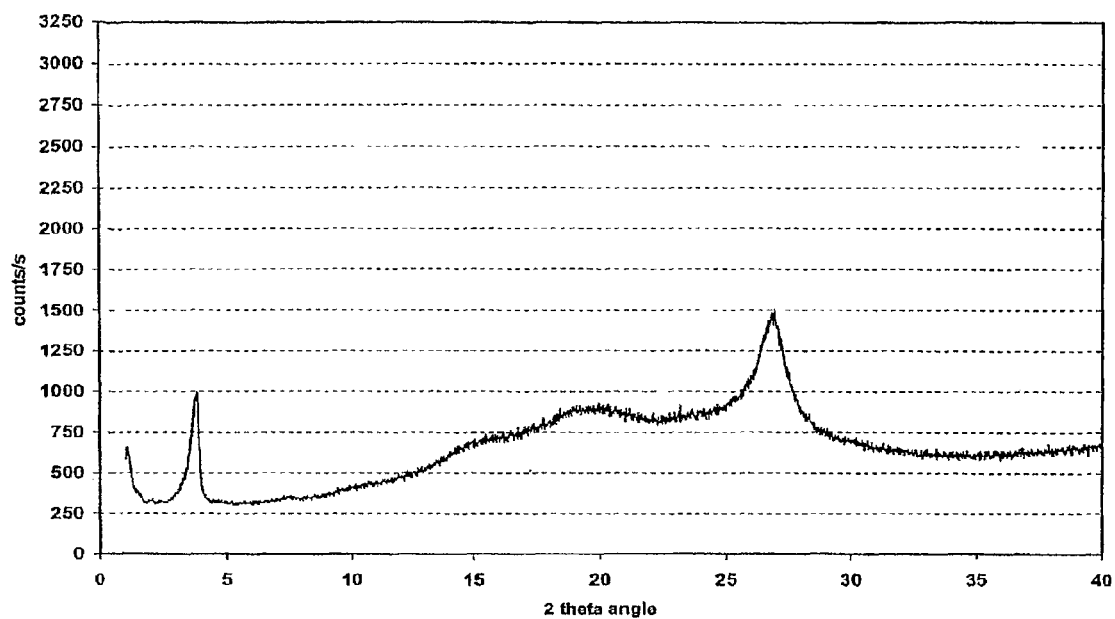
FIG. 12 shows an XRPD pattern characteristic of Form H.

Form H can be identified by its X-ray powder diffraction (XRPD) pattern, one example of which is provided in is provided in FIG. 12. Relatively prominent two-theta peaks were observed at about 3.5, about 6.9, about 10.3, about 16.9, about 20.6, and about 26.8 degrees. In some embodiments, the crystalline Form H of the invention has an XRPD pattern substantially as shown in FIG. 12 (two-theta values provided in Example 16), where the term "substantially" in this instance indicates that two-theta values for individual peaks can vary about ±0.2°. The relative intensities of the peaks can also vary, depending upon the sample preparation technique, the sample mounting procedure and the particular instrument employed. Powder X-ray diffraction two-theta data consistent with Form E is provided in Example 16 below. As discussed above, many factors can affect the 2-theta values. Therefore, the peak assignments listed in Example 16 can vary by plus or minus about 0.2°.

Crystalline Form H can be prepared by any of numerous methods in the art. In some embodiments, Form H can be prepared by adding an aqueous solution of a lactic acid salt of the compound of Formula I to a solvent at a temperature of about 0 to about 10° C., wherein the concentration of said aqueous solution is about 100 to about 350 mg/mL; and said solvent comprises acetonitrile. In some embodiments, Form H can be prepared by evaporating an aqueous solution of a lactic acid salt of the compound of Formula I at a temperature of about 20 to about 30° C.

An example method for preparing Form H is carried out by:

(a) adding an aqueous solution of a lactic acid salt of the compound of Formula I to a solvent at a temperature of about 0 to about 10° C. wherein the concentration of the aqueous solution is about 100 to about 350 mg/mL; and the solvent contains acetonitrile;

(b) keeping the resultant mixture in step (a) at a temperature of about 0 to about 10° C. for a period of time sufficient for the formation of Form H; and (c) isolating Form H.

The concentration of the aqueous solution can be about 100 to about 350 mg/mL. In some embodiments, the concentration of the aqueous solution is about 200 to about 350 mg/mL. In some embodiments, the concentration of the aqueous solution is about 300 to about 350 mg/mL.

The temperature in steps (a) and (b) can be about 0 to about 10° C. In some embodiments, the temperature is about 2 to about 8° C. In some embodiments, the temperature is about 2 to about 5° C. In some embodiments, the temperature is about 2° C.

In step (b), the mixture is kept at a temperature of about 0 to about 10° C. to allow the formation of Form H. In some embodiments, the mixture in step (b) is kept at a temperature of about 0 to about 10° C. (e.g., 2° C.) for at least about 24 hours.

Another example method for preparing Form H is carried out by:

evaporating an aqueous solution of a lactic acid salt of the compound of Formula I at a temperature of about 20 to about 30° C. for a period of time sufficient for the formation of Form H.

Evaporation can be carried out at ambient temperature, i.e., in a climatized laboratory at 23±2° C. In some embodiments, evaporation is carried out under a fast $N_2$ flow (e.g., flow rate of approximately 0.4 liters/min) or evaporation is carried out under a slow $N_2$ flow (e.g., approximately 0.03 liters/min) through a channel system as described in, for example, WO 03/026797 A2. The duration of the evaporation experiment was about 50 to about 75, or about 67 hours, and the resulting suspensions equilibrated for about 50 to about 75, or about 68 hours.

The methods for preparation of the mesomorphic form (Form H) provided herein can result in substantially a single pure form (e.g., compositions containing less than about 20%, about 10%, about 5%, or about 3% by weight of impurities, amorphous material and/or other crystalline forms) as well as mixtures enriched in a single pure form (e.g., mixtures containing greater than about 50% by weight Form H relative to, for example, impurities, amorphous material or other crystalline forms). Accordingly, the present invention further provides compositions containing Form H. In some embodiments, at least about 50%, at least about 70%, at least about 80%, at least about 90%, at least about 95%, or at least about 99% by weight of total solvate of lactic acid salt of the compound of formula I in a composition is present as Form H. Amounts of different crystalline forms of in a composition can be determined by routine spectroscopic methods, such as X-ray powder diffraction, DSC, and the like.

The instant invention also provides for solid compositions (i.e., formulations) containing the mesomorphic form (Form H) of a lactic acid salt of the compound of Formula I with pharmaceutically acceptable carriers, excipients, binders, diluents or the like, to treat or ameliorate a variety of disorders related to the activity of VEGF-RTK, more particularly for example, angiogenesis associated with cancer. Excipients, diluents, binders, carriers and the like include, but are not limited to, microcrystalline cellulose, lactose, dibasic calcium phosphate, tribasic calcium phosphate, sodium starch glycolate (NaSG), crospovidone, crosscarmellose (CC), sodium lauryl sulfate (SLS), Tween, polyethylene glycol (PEG), povidone, hydroxypropyl cellulose (HPMC), Mg stearate, Ca stearate, stearic acid, sodium stearate fumarate, and silicon dioxide. In some embodiments, the compositions are in powder form suitable for compaction, tableting, and/or oral administration.

Form I

In a fourth aspect, the present invention provides, inter alia, an intermediate state (Form I) of a crystalline hydrate of a lactic acid salt of a compound of Formula I, which was formed in an aqueous environment (e.g., a suspension containing substantial amounts of water). Accordingly, crystalline Form I comprises a high water content as suggested by Karl Fischer titration which indicated a water content of about 20%.

Figure 13:
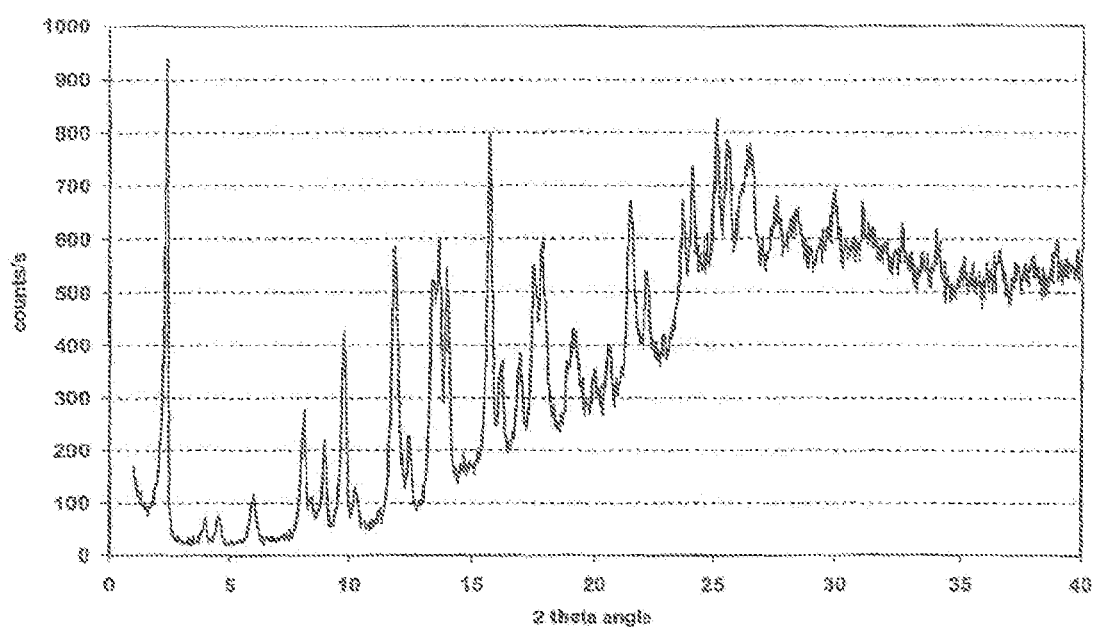
FIG. 13 shows an XRPD pattern characteristic of Form I.

Form I (as a wet semi solid) can be identified by its X-ray powder diffraction (XRPD) pattern, one example of which is provided in is provided in FIG. 13. Relatively prominent two-theta peaks were at about 2.3, about 4.0, about 4.6, about 6.0, about 8.1, about 9.0, about 9.8, about 10.3, about 11.9, about 12.5, about 13.4, about 13.6, about 14.0, about 15.7, about 16.2, about 17.0, about 17.6, about 17.8, about 19.2, about 20.0, about 20.6, about 21.5, about 22.2, about 23.7, about 24.1, about 25.1, about 25.5, about 26.5, and about 30.0 degrees. In some embodiments, the crystalline Form I of the invention has an XRPD pattern substantially as shown in FIG. 13 (two-theta values provided in Example 17), where the term "substantially" in this instance indicates that two-theta values for individual peaks can vary about ±0.2°. The relative intensities of the peaks can also vary, depending upon the sample preparation technique, the sample mounting procedure and the particular instrument employed. Powder X-ray diffraction two-theta data consistent with Form I is provided in Example 17 below. As discussed above, many factors can affect the 2-theta values. Therefore, the peak assignments listed in Example 17 can vary by plus or minus about 0.2°.

Crystalline Form I has a high water content. Karl Fischer titration of Form I samples indicates water content of about 20%.

Crystalline Form I can be prepared by any of numerous methods in the art. In some embodiments, Form I can be prepared by combining Form A with a solvent comprising at least about 50% by volume of water. One example of preparing Form I is as follows:

(a) adding Form A to a solvent comprising at least about 50% by volume of water, wherein the relative ratio of Form A to the Water is from about 100 mg/mL to about 350 mg/mL; and (b) keeping the mixture from step (a) at a temperature of about 20 to about 30° C. for a period of time of about 3 days or greater.

In some embodiments, the solvent contains at least about 50% by volume of water. In some embodiments, the solvent is water. The addition of Form A to water can result in an aqueous solution initially. In some embodiments, the amount of Form A in the water is from about 100 mg/mL to about 350 mg/mL. In some embodiments, the amount of Form A in the water is from about 100 mg/mL to about 200 mg/mL. In some embodiments, the amount of Form A in the water is from about 125 mg/mL to about 150 mg/mL. Depending on the relative ratio of Form A to the water, the initial solution turns into a thick and highly viscous paste after a period of time such as about 6 hours. The paste can be allowed to stand (optionally with stirring) for a period of time of about 2 days or greater. In some embodiments, the period of time of standing is about 3 days or greater to allow the formation of Form I. The resulting paste can be used for XRPD characterization without separation.

The methods for preparation of the intermediate state (Form I) of a crystalline hydrate of a lactic acid salt of a compound of Formula I, provided herein can result in substantially a single pure form (e.g., compositions containing less than about 20%, about 10%, about 5%, or about 3% by weight of impurities, amorphous material and/or other crystalline forms) as well as mixtures enriched in a single pure form (e.g., mixtures containing greater than about 50% by weight Form I relative to, for example, impurities, amorphous material or other crystalline forms). Accordingly, the present invention further provides compositions containing Form I. In some embodiments, at least about 50%, at least about 70%, at least about 80%, at least about 90%, at least about 95%, or at least about 99% by weight of total solvate of lactic acid salt of the compound of formula I in a composition is present as Form I. Amounts of different crystalline forms of in a composition can be determined by routine spectroscopic methods, such as X-ray powder diffraction, DSC, and the like.

The instant invention also provides for solid compositions (i.e., formulations) containing the intermediate state (Form I) of a lactic acid salt of the compound of Formula I with pharmaceutically acceptable carriers, excipients, binders, diluents or the like, to treat or ameliorate a variety of disorders related to the activity of VEGF-RTK, more particularly for example, angiogenesis associated with cancer. Excipients, diluents, binders, carriers and the like include, but are not limited to, microcrystalline cellulose, lactose, dibasic calcium phosphate, tribasic calcium phosphate, sodium starch glycolate (NaSG), crospovidone, crosscarmellose (CC), sodium lauryl sulfate (SLS), Tween, polyethylene glycol (PEG), povidone, hydroxypropyl cellulose (HPMC), Mg stearate, Ca stearate, stearic acid, sodium stearate fumarate, and silicon dioxide. In some embodiments, the compositions are in powder form suitable for compaction, tableting, and/or oral administration.

One embodiment of the invention is a method of treating a patient in need of an inhibitor of vascular endothelial growth factor receptor tyrosine kinase which includes administering an effective amount of a solid pharmaceutical formulation, containing the intermediate state (Foran I) of a crystalline hydrate of a lactic acid salt of a compound of Formula I, to a patient in need thereof. Preferably, the formulation is a powder formulation, suitable for oral administration.

One embodiment of the invention is a method for inhibiting tumor growth in a patient includes administering an effective amount of a solid pharmaceutical formulation, containing the intermediate state (Form I) of a crystalline hydrate of a lactic acid salt of a compound of Formula I, to a patient having a tumor. Preferably, the formulation is a powder formulation, suitable for oral administration.

One embodiment of the invention is a method for inhibiting the proliferation of capillaries in a patient which includes administering an effective amount of a solid pharmaceutical formulation, containing the intermediate state (Form I) of a crystalline hydrate of a lactic acid salt of a compound of Formula I, according to a patient in need. Preferably, the formulation is a powder formulation, suitable for oral administration.

One embodiment of the invention is a method of preparing solid pharmaceutical formulations which includes mixing the intermediate state (Form I) of a crystalline hydrate of a lactic acid salt of a compound of Formula I with a pharmaceutically acceptable carrier. Preferably, the formulation is a powder formulation, suitable for oral administration.

In further embodiments, the present invention provides a method of treating a patient with a solid formulation containing the intermediate state (Form I) of a crystalline hydrate of a lactic acid salt of a compound of Formula I, by oral administration of the formulation to the patient. In some embodiments, the intermediate state (Form I) of a crystalline hydrate form of a lactic acid salt of the compound of formula I is a mono-lactic acid salt. In some embodiments, the solid formulation is in the form of a powder. In some embodiments, the solid formulation can be prepared by compaction or other treatment of a powder containing the intermediate state (Form I) of a crystalline hydrate form of a lactic acid salt of the compound of formula I. In further embodiments, the solid formulation of can be prepared in the form of a pill, tablet, capsule, or a caplet.

In some embodiments, the crystalline form of the lactic acid salt of the compound of formula I which is present in the solid formulation remains substantially as Form I, under ambient conditions for a period greater than about 36 hours, greater than about 1 week, greater than about 1 month, greater than about 6 months, or greater than about 1 year.

According to embodiments of methods of treating a patient, the patient can be a cancer patient. In some embodiments, the patient is diagnosed with multiple myeloma (MM), acute myelogenous leukemia (AML), prostate cancer, breast cancer, colon cancer, or melanoma. In further embodiments, the patient is a refractory patient, such as a patient showing resistance to preexisting therapeutics or treatment regimens, including prescribed/clinical dosing schedules. In some embodiments, the patient can be treated with a dose that is less than the maximum tolerated dose (MTD), such as a dose of about 0.25 to 30 mg/kg of the lactic acid salt of the compound of formula I. "MTD," as used herein, refers to the highest dose during diagnostic, prophylactic or therapeutic procedures that a body can tolerate without substantial injury. The MTD is reviewed in context of alteration of physiological function which would be predicted to alter a patients life span. Factors include: no more than 10% decrease in body weight gain relative to controls, target organ toxicity, and significant alterations in clinical pathological parameters.

Solvates

In a fifth aspect, the present invention provides, inter alia, a crystalline solvate of a lactic acid salt of a compound of Formula I.

As used here, the term "solvate" is meant to refer to crystalline material containing non-aqueous solvent molecules (e.g., molecules other than or in addition to water such as organic solvents like, for example, 1,4-dioxane, benzene, toluene, anisole and the like.). In some embodiments, the solvate is a 1,4-dioxane-solvate or a benzene-solvate. In some embodiments, the solvate is a 1,4-dioxane-solvate. In some embodiments, the solvate is a benzene-solvate. In some embodiments of the solvates of the invention, the molar ratio of the solvent-content to the lactic acid salt of the compound of Formula I is about 0.5. In some embodiments, the solvate is hemi-solvate. In some embodiments, the lactic acid salt in the solvate is a mono-lactic acid salt.

1,4-Dioxane-Solvate: Form F

Figure 10:
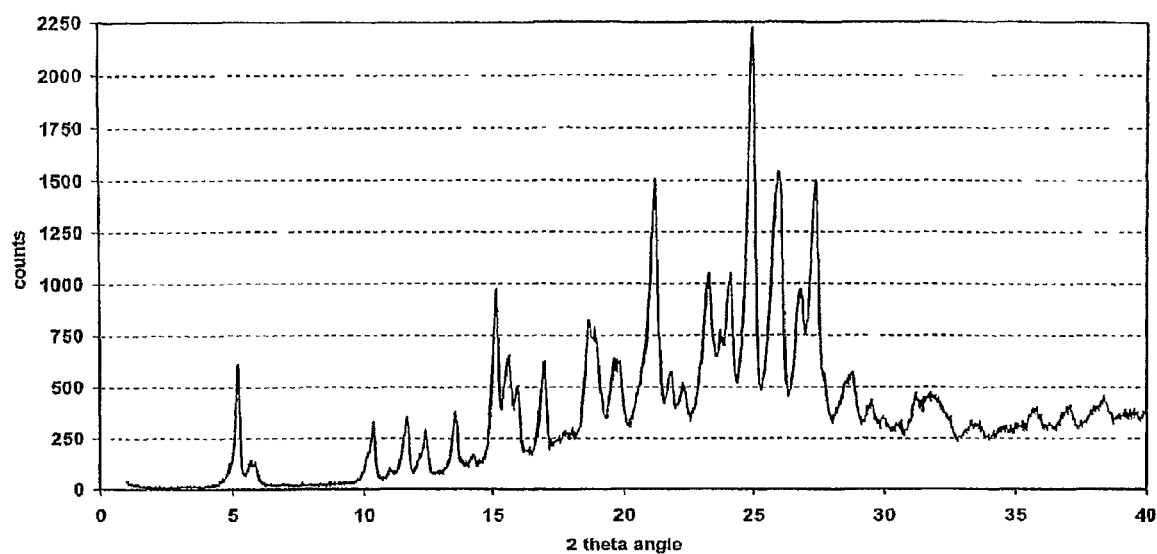
FIG. 10 shows an XRPD pattern characteristic of Form F.

In some embodiments, the crystalline solvate of a lactic acid salt of the compound of Formula I is a crystalline 1,4-dioxane-solvate. In some embodiments of the 1,4-dioxanesolvate, the solvate is a hemi-solvate. In some embodiments of the 1,4-dioxane-solvate, the lactic acid salt of the compound of Formula I is a mono-lactic salt. In some embodiments, the crystalline 1,4-dioxane-solvate of a lactic acid salt of the compound of Formula I is crystalline Form F. Crystalline Form F is characterized as a crystalline 1,4-dioxane-hemi-solvate of a lactic acid salt of the compound of formula I. In some embodiments of Form F, the lactic acid salt is a mono-lactic acid salt. Form F can be identified by its X-ray powder diffraction (XRPD) pattern, one example of which is provided in is provided in FIG. 10. Relatively prominent two-theta peaks were at about 5.2, about 5.7, about 10.4, about 11.7, about 12.4, about 13.6, about 15.2, about 15.6, about 16.0, about 17.0, about 18.6, about 18.9, about 19.7, about 21.2, about 21.8, about 22.2, about 23.3, about 24.1, about 25.0, about 26.0, about 26.8, about 27.4, about 28.8, about 31.2, and about 31.7 degrees. In some embodiments, the crystalline Form F of the invention has an XRPD pattern substantially as shown in FIG. 10 (two-theta values provided in Example 14), where the term "substantially" in this instance indicates that two-theta values for individual peaks can vary about ±0.2°. The relative intensities of the peaks can also vary, depending upon the sample preparation technique, the sample mounting procedure and the particular instrument employed. Powder X-ray diffraction two-theta data consistent with Form F is provided in Example 14 below. As discussed above, many factors can affect the 2-theta values. Therefore, the peak assignments listed in Example 14 can vary by plus or minus about 0.2°.

TG-FTIR analysis of Form F samples showed a weight loss of about 7.2% which is attributed to release of 1,4-dioxane. Release of the dioxane was found to occur mainly between about 50° C. and about 160° C. After release of the dioxane, the $^1$H-NMR analysis of the resultant sample confirmed the chemical integrity of the lactate salt of the compound of formula I. Since the theoretical 1,4-dioxane content of a hemisolvate is expected to be 8.4%, it is postulated that Form F is a 1,4-dioxane hemi-solvate.

Crystalline Form F can be prepared by any of numerous methods in the art. In some embodiments, Form F can be prepared by crystallizing Form F from a solution containing 1,4-dioxane. One example of preparing Form F is as follows:

(a) suspending Form A in a solution which contains 1,4-dioxane;

(b) allowing the resulting suspension to stir at a temperature and for a period of time sufficient for formation of Form F; and (c) isolating Form F.

The solution of step (a) contains 1,4-dioxane in a sufficient amount to afford Form F. In some embodiments, the solution contains 1,4-dioxane and an ether such as methyl t-butyl ether. In some embodiments, the solution contains 1,4-dioxane and methyl t-butyl ether. In some further embodiments, the ratio of 1,4-dioxane to methyl t-butyl ether is about 1:1 by volume.

The suspension is stirred at a temperature and for a period of time sufficient for formation of Form F. In some embodiments, the suspension is stirred at a temperature of about 2° C. to about 15° C. In some embodiments, the suspension is stirred at a temperature of about 2° C. to about 10° C. In some embodiments, the suspension is stirred at a temperature of about 2° C. to about 8° C. In some embodiments, the suspension is stirred at a temperature of about 5° C. In some embodiments, the suspension is stirred for a period of time of about 10 hours or longer. In some embodiments, the suspension is stirred for a period of time of about 15 hours or longer. In some embodiments, the suspension is stirred for a period of time of about 18 hours or longer.

Benzene-Solvate: Form G

Figure 11:
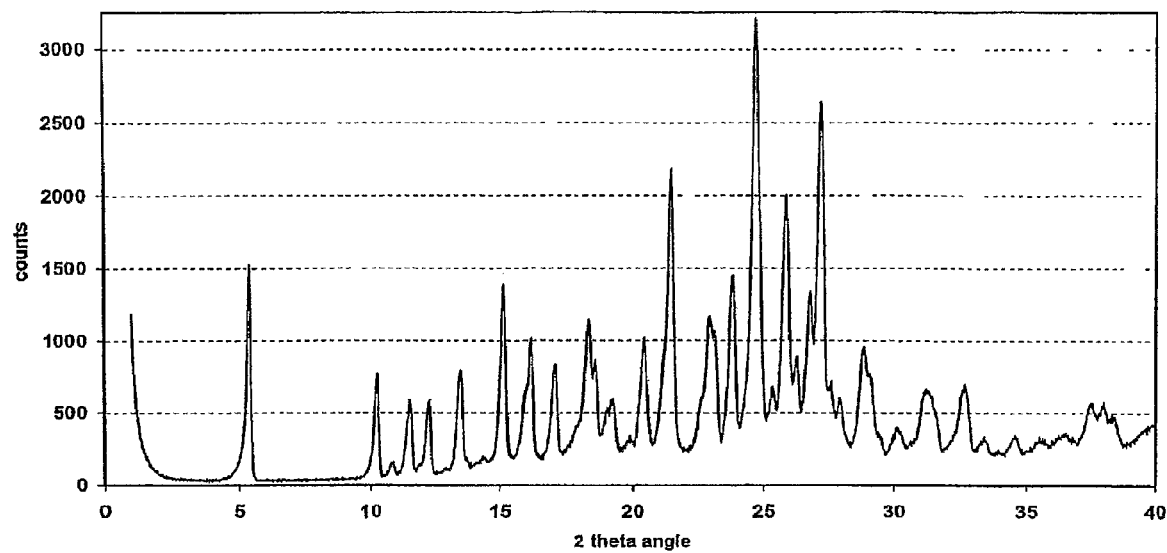
FIG. 11 shows an XRPD pattern characteristic of Form G.

In some embodiments, the crystalline solvate of a lactic acid salt of the compound of Formula I is a crystalline benzene-solvate. In some embodiments of the benzene-solvate, the solvate is a hemi-solvate. In some embodiments of the benzene-solvate, the lactic acid salt of the compound of Formula I is a mono-lactic salt. In some embodiments, the crystalline benzene-solvate of a lactic acid salt of the compound of Formula I is crystalline Form G. Crystalline Form G is characterized as a crystalline benzene-hemi-solvate of a lactic acid salt of the compound of formula I. In some embodiments of Form G, the lactic acid salt is a mono-lactic acid salt. Form G can be identified by its X-ray powder diffraction (XRPD) pattern, one example of which is provided in is provided in FIG. 11. Relatively prominent two-theta peaks were at about 5.4, about 10.3, about 11.5, about 12.3, about 13.5, about 15.2, about 16.2, about 17.1, about 18.4, about 18.6, about 19.3, about 20.5, about 21.5, about 22.9, about 23.8, about 24.7, about 25.9, about 26.3, about 26.8, about 27.3, about 28.9, about 31.2, and about 32.7 degrees. In some embodiments, the crystalline Form G of the invention has an XRPD pattern substantially as shown in FIG. 11 (two-theta values provided in Example 15), where the term "substantially" in this instance indicates that two-theta values for individual peaks can vary about 10.2°. The relative intensities of the peaks can also vary, depending upon the sample preparation technique, the sample mounting procedure and the particular instrument employed. Powder X-ray diffraction two-theta data consistent with Form G is provided in Example 15 below. As discussed above, many factors can affect the 2-theta values. Therefore, the peak assignments listed in Example 15 can vary by plus or minus about 0.2°.

TG-FTIR analysis of Form G samples revealed a weight loss of about 7.4% in the temperature range from about 140° C. to about 180° C., attributed to release of benzene. Since the theoretical benzene content for a hemisolvate is expected to be 7.5%, it is postulated that Form G is a benzene hemisolvate.

Crystalline Form G can be prepared by any of numerous methods in the art. In some embodiments, Form G can be prepared by crystallizing Form G from a solution containing benzene. One example of preparing Form G is as follows:

(a) suspending Form A in a solution which contains benzene;

(b) allowing the suspension to stir at a temperature and for a period of time sufficient for formation of Form G; and (c) isolating Form G.

The solution of step (a) contains a sufficient amount of benzene in order to afford Form G. In some embodiments, the solution contains at least 50% by volume of benzene. In some embodiments, the solution contains at least 80% by volume of benzene. In some embodiments, the solution contains at least 90% by volume of benzene. In some embodiments, the solution is benzene.

The suspension is stirred at a temperature and for a period of time sufficient for formation of Form G. In some embodiments, the suspension is stirred at a temperature of about 10° C. to about 30° C. In some embodiments, the suspension is stirred at a temperature of about 20° C. to about 30° C. In some embodiments, the suspension is stirred at a temperature of about 20° C. to about 25° C. In some embodiments, the suspension is stirred at a temperature of about 23° C. In some embodiments, the suspension is stirred for a period of time of about 15 hours or longer. In some embodiments, the suspension is stirred for a period of time of about 24 hours or longer. In some embodiments, the suspension is stirred for a period of time of about 48 hours or longer. In some embodiments, the suspension is stirred for a period of time of about 72 hours or longer.

The methods for preparation of the crystalline solvate forms (e.g., from F and Form G) provided herein can result in substantially a single pure form (e.g., compositions containing less than about 20%, about 10%, about 5%, or about 3% by weight of impurities, amorphous material and/or other crystalline forms) as well as mixtures enriched in a single pure form (e.g., mixtures containing greater than about 50% by weight Form F relative to, for example, impurities, amorphous material or other crystalline forms). Accordingly, the present invention further provides compositions containing Form F or Form G. In some embodiments, at least about 50%, at least about 70%, at least about 80%, at least about 90%, at least about 95%, or at least about 99% by weight of total solvate of lactic acid salt of the compound of formula I in a composition is present as Form F. In some embodiments, at least about 50%, at least about 70%, at least about 80%, at least about 90%, at least about 95%, or at least about 99% by weight of total solvate of lactic acid salt of the compound of formula I in a composition is present as Form G. Amounts of different crystalline forms of in a composition can be determined by routine spectroscopic methods, such as X-ray powder diffraction, DSC, and the like.

The instant invention also provides for solid compositions (i.e., formulations) containing a crystalline solvate form of a lactic acid salt of the compound of Formula I (e.g., Form F and Form G) with pharmaceutically acceptable carriers, excipients, binders, diluents or the like, to treat or ameliorate a variety of disorders related to the activity of VEGF-RTK, more particularly for example, angiogenesis associated with cancer. Excipients, diluents, binders, carriers and the like include, but are not limited to, microcrystalline cellulose, lactose, dibasic calcium phosphate, tribasic calcium phosphate, sodium starch glycolate (NaSG), crospovidone, crosscarmellose (CC), sodium lauryl sulfate (SLS), Tween, polyethylene glycol (PEG), povidone, hydroxypropyl cellulose (HPMC), Mg stearate, Ca stearate, stearic acid, sodium stearate fumarate, and silicon dioxide. In some embodiments, the compositions are in powder form suitable for compaction, tableting, and/or oral administration.

EXAMPLES

Example 1

Synthesis of 4-amino-5-fluoro-3-[6-(4-methylpiperazin-1-yl)-1H-benzimidazol-2-yl]-1H-quinolin-2-one, Lactic Acid Salt Thereof, and Form A

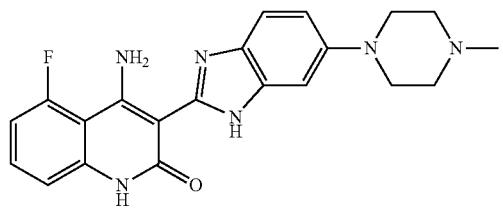 [SMILES: CN1CCN(c2ccc3nc(-c4c(N)c5c(F)cccc5[nH]c4=O)[nH]c3c2)CC1]

A. Synthesis of 5-(4-Methyl-piperazin-1-yl)-2-nitroaniline

Procedure A

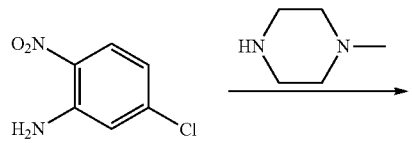

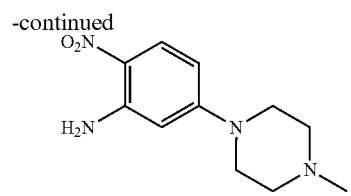

5-Chloro-2-nitroaniline (500 g, 2.898 mol) and 1-methyl piperazine (871 g, 8.693 mol) were placed in a 2000 mL flask fitted with a condenser and purged with $N_2$. The flask was placed in an oil bath at 100° C. and heated until the 5-chloro-2-nitroaniline was completely reacted (typically overnight) as determined by HPLC. After HPLC confirmed the disappearance of the 5-chloro-2-nitroaniline, the reaction mixture was poured directly (still warm) into 2500 mL of room temperature water with mechanical stirring. The resulting mixture was stirred until it reached room temperature and then it was filtered. The yellow solid thus obtained was added to 1000 mL of water and stirred for 30 minutes. The resulting mixture was filtered, and the resulting solid was washed with TBME (500 mL, 2×) and then was dried under vacuum for one hour using a rubber dam. The resulting solid was transferred to a drying tray and dried in a vacuum oven at 50° C. to a constant weight to yield 670 g (97.8%) of the title compound as a yellow powder.

Procedure B

5-Chloro-2-nitroaniline (308.2 g, 1.79 mol) was added to a 4-neck 5000 mL round bottom flask fitted with an overhead stirrer, condenser, gas inlet, addition funnel, and thermometer probe. The flask was then purged with $N_2$. 1-Methylpiperazine (758.1 g, 840 mL, 7.57 mol) and 200 proof ethanol (508 mL) were added to the reaction flask with stirring. The flask was again purged with $N_2$, and the reaction was maintained under $N_2$. The flask was heated in a heating mantle to an internal temperature of 97° C. (+/−5° C.) and maintained at that temperature until the reaction was complete (typically about 40 hours) as determined by HPLC. After the reaction was complete, heating was discontinued and the reaction was cooled to an internal temperature of about 20° C. to 25° C. with stirring, and the reaction was stirred for 2 to 3 hours. Seed crystals (0.20 g, 0.85 mmol) of 5-(4-methyl-piperazin-1-yl)-2-nitroaniline were added to the reaction mixture unless precipitation had already occurred. Water (2,450 mL) was added to the stirred reaction mixture over a period of about one hour while the internal temperature was maintained at a temperature ranging from about 20° C. to 30° C. After the addition of water was complete, the resulting mixture was stirred for about one hour at a temperature of 20° C. to 30° C. The resulting mixture was then filtered, and the flask and filter cake were washed with water (3×2.56 L). The golden yellow solid product was dried to a constant weight of 416 g (98.6% yield) under vacuum at about 50° C. in a vacuum oven.

Procedure C

5-Chloro-2-nitroaniline (401 g, 2.32 mol) was added to a 4-neck 12 L round bottom flask fitted with an overhead stirrer, condenser, gas inlet, addition funnel, and thermometer probe. The flask was then purged with $N_2$. 1-Methylpiperazine (977 g, 1.08 L, 9.75 mol) and 100% ethanol (650 mL) were added to the reaction flask with stirring. The flask was again purged with $N_2$, and the reaction was maintained under $N_2$. The flask was heated in a heating mantle to an internal temperature of 97° C. (+/−5° C.) and maintained at that temperature until the reaction was complete (typically about 40 hours) as determined by HPLC. After the reaction was complete, heating was discontinued and the reaction was cooled to an internal temperature of about 80° C. with stirring, and water (3.15 L) was added to the mixture via an addition funnel over the period of 1 hour while the internal temperature was maintained at 82° C. (+/−3° C.). After water addition was complete, heating was discontinued and the reaction mixture was allowed to cool over a period of no less than 4 hours to an internal temperature of 20-25° C. The reaction mixture was then stirred for an additional hour at an internal temperature of 20-30° C. The resulting mixture was then filtered, and the flask and filter cake were washed with water (1×1 L), 50% ethanol (1×μL), and 95% ethanol (1×1 L). The golden yellow solid product was placed in a drying pan and dried to a constant weight of 546 g (99% yield) under vacuum at about 50° C. in a vacuum oven.

B. Synthesis of [6-(4-Methyl-piperazin-1-yl)-1H-benzimidazol-2-yl]-acetic acid ethyl ester Procedure A

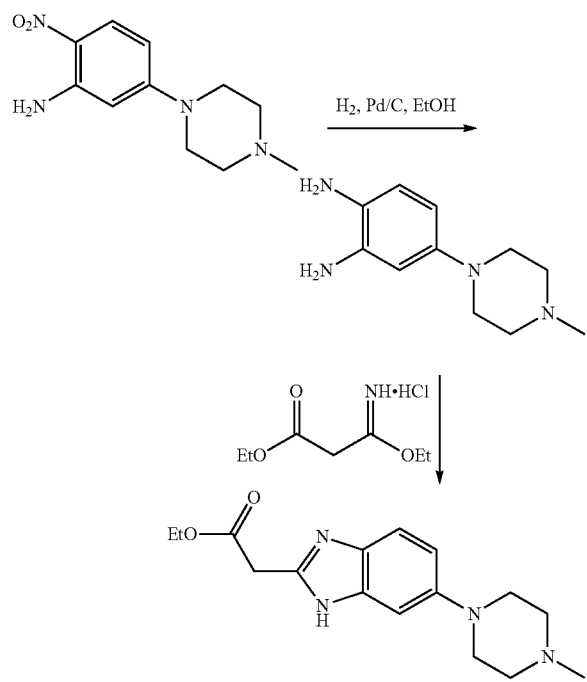

A 5000 mL, 4-neck flask was fitted with a stirrer, thermometer, condenser, and gas inlet/outlet. The equipped flask was charged with 265.7 g (1.12 mol. 1.0 eq) of 5-(4-methyl-piperazin-1-yl)-2-nitroaniline and 2125 mL of 200 proof EtOH. The resulting solution was purged with $N_2$ for 15 minutes. Next, 20.0 g of 5% Pd/C (50% $H_2O$ w/w) was added. The reaction was vigorously stirred at 40-50° C. (internal temperature) while $H_2$ was bubbled through the mixture. The reaction was monitored hourly for the disappearance of 5-(4-methyl-piperazin-1-yl)-2-nitroaniline by HPLC. The typical reaction time was 6 hours.

After all the 5-(4-methyl-piperazin-1-yl)-2-nitroaniline had disappeared from the reaction, the solution was purged with $N_2$ for 15 minutes. Next, 440.0 g (2.25 mol) of ethyl 3-ethoxy-3-iminopropanoate hydrochloride was added as a solid. The reaction was stirred at 40-50° C. (internal temperature) until the reaction was complete. The reaction was monitored by following the disappearance of the diamino compound by HPLC. The typical reaction time was 1-2 hours. After the reaction was complete, it was cooled to room temperature and filtered through a pad of Celite filtering material. The Celite filtering material was washed with absolute EtOH (2×250 mL), and the filtrate was concentrated under reduced pressure providing a thick brown/orange oil. The resulting oil was taken up in 850 mL of a 0.37% HCl solution. Solid NaOH (25 g) was then added in one portion, and a precipitate formed. The resulting mixture was stirred for 1 hour and then filtered. The solid was washed with $H_2O$ (2×400 mL) and dried at 50° C. in a vacuum oven providing 251.7 g (74.1%) of [6-(4-methyl-piperazin-1-yl)-1H-benzoimidazol-2-yl]-acetic acid ethyl ester as a pale yellow powder.

Procedure B

A 5000 mL, 4-neck jacketed flask was fitted with a mechanical stirrer, condenser, temperature probe, gas inlet, and oil bubbler. The equipped flask was charged with 300 g (1.27 mol) of 5-(4-methyl-piperazin-1-yl)-2-nitroaniline and 2400 mL of 200 proof EtOH (the reaction may be and has been conducted with 95% ethanol and it is not necessary to use 200 proof ethanol for this reaction). The resulting solution was stirred and purged with $N_2$ for 15 minutes. Next, 22.7 g of 5% Pd/C (50% $H_2O$ w/w) was added to the reaction flask. The reaction vessel was purged with $N_2$ for 15 minutes. After purging with $N_2$, the reaction vessel was purged with $H_2$ by maintaining a slow, but constant flow of $H_2$ through the flask. The reaction was stirred at 45-55° C. (internal temperature) while $H_2$ was bubbled through the mixture until the 5-(4-methyl-piperazin-1-yl)-2-nitroaniline was completely consumed as determined by HPLC. The typical reaction time was 6 hours.

After all the 5-(4-methyl-piperazin-1-yl)-2-nitroaniline had disappeared from the reaction, the solution was purged with $N_2$ for 15 minutes. The diamine intermediate is air sensitive so care was taken to avoid exposure to air. 500 g (2.56 mol) of ethyl 3-ethoxy-3-iminopropanoate hydrochloride was added to the reaction mixture over a period of about 30 minutes. The reaction was stirred at 45-55° C. (internal temperature) under $N_2$ until the diamine was completely consumed as determined by HPLC. The typical reaction time was about 2 hours. After the reaction was complete, the reaction was filtered while warm through a pad of Celite. The reaction flask and Celite were then washed with 200 proof EtOH (3×285 mL). The filtrates were combined in a 5000 mL flask, and about 3300 mL of ethanol was removed under vacuum producing an orange oil. Water (530 mL) and then 1M HCL (350 mL) were added to the resulting oil, and the resulting mixture was stirred. The resulting solution was vigorously stirred while 30% NaOH (200 mL) was added over a period of about 20 minutes maintaining the internal temperature at about 25-30° C. while the pH was brought to between 9 and 10. The resulting suspension was stirred for about 4 hours while maintaining the internal temperature at about 20-25° C. The resulting mixture was filtered, and the filter cake was washed with $H_2O$ (3×300 mL). The collected solid was dried to a constant weight at 50° C. under vacuum in a vacuum oven providing 345.9 g (90.1%) of [6-(4-methyl-piperazin-1-yl)-1H-benzoimidazol-2-yl]-acetic acid ethyl ester as a pale yellow powder. In an alternative work up procedure, the filtrates were combined and the ethanol was removed under vacuum until at least about 90% had been removed. Water at a neutral pH was then added to the resulting oil, and the solution was cooled to about 0° C. An aqueous 20% NaOH solution was then added slowly with rapid stirring to bring the pH up to 9.2 (read with pH meter). The resulting mixture was then filtered and dried as described above. The alternative work up procedure provided the light tan to light yellow product in yields as high as 97%.

Method for Reducing Water Content of [6-(4-Methyl-piperazin-1-yl)-1H-benzoimidazol-2-yl]-acetic acid ethyl ester

[6-(4-Methyl-piperazin-1-yl)-1H-benzimidazol-2-yl]acetic acid ethyl ester (120.7 grams) that had been previously worked up and dried to a water content of about 8-9% $H_2O$ was placed in a 2000 mL round bottom flask and dissolved in absolute ethanol (500 mL). The amber solution was concentrated to a thick oil using a rotary evaporator with heating until all solvent was removed. The procedure was repeated two more times. The thick oil thus obtained was left in the flask and placed in a vacuum oven heated at 50° C. overnight. Karl Fisher analysis results indicated a water content of 5.25%. The lowered water content obtained by this method provided increased yields in the procedure of Example 4. Other solvents such as toluene and THF may be used in place of the ethanol for this drying process.

C. Synthesis of 4-Amino-5-fluoro-3-[6-(4-methyl-piperazin-1-yl)-1H-benzimidazol-2-yl]-1H-quinolin-2-one Procedure A

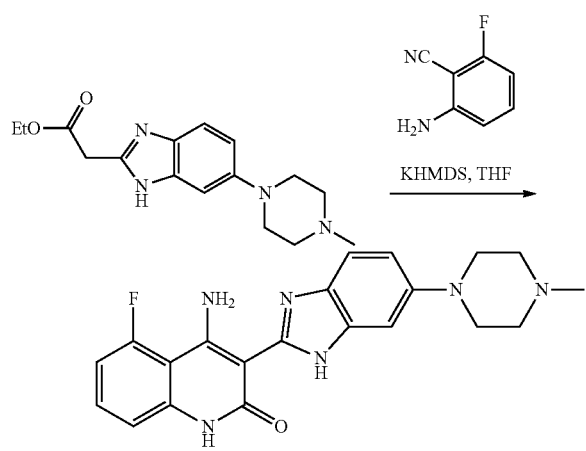

[6-(4-Methyl-piperazin-1-yl)-1H-benzimidazol-2-yl]acetic acid ethyl ester (250 g, 820 mmol) (dried with ethanol as described above) was dissolved in THF (3800 mL) in a 5000 mL flask fitted with a condenser, mechanical stirrer, temperature probe, and purged with argon. 2-Amino-6-fluoro-benzonitrile (95.3 g, 700 mmol) was added to the solution, and the internal temperature was raised to 40° C. When all the solids had dissolved and the solution temperature had reached 40° C., solid KHMDS (376.2 g, 1890 mmol) was added over a period of 5 minutes. When addition of the potassium base was complete, a heterogeneous yellow solution was obtained, and the internal temperature had risen to 62° C. After a period of 60 minutes, the internal temperature decreased back to 40° C., and the reaction was determined to be complete by HPLC (no starting material or uncyclized intermediate was present). The thick reaction mixture was then quenched by pouring it into $H_2O$ (6000 mL) and stirring the resulting mixture until it had reached room temperature. The mixture was then filtered, and the filter pad was washed with water (1000 mL 2×). The bright yellow solid was placed in a drying tray and dried in a vacuum oven at 50° C. overnight providing 155.3 g (47.9%) of the desired 4-amino-5-fluoro-3-[6-(4-methyl-piperazin-1-yl)-1H-benzimidazol-2-yl]-1H-quinolin-2-one.

Procedure B

A 5000 mL 4-neck jacketed flask was equipped with a vacuum distillation apparatus, a temperature probe, a $N_2$ gas inlet, an addition funnel, and a mechanical stirrer. [6-(4-Methyl-piperazin-1-yl)-1H-benzimidazol-2-yl]-acetic acid ethyl ester (173.0 g, 570 mmol) was charged into the reactor, and the reactor was purged with $N_2$ for 15 minutes. Dry THF (2600 mL) was then charged into the flask with stirring. After all the solid had dissolved, solvent was removed by vacuum distillation using heat as necessary. After 1000 mL of solvent had been removed, distillation was stopped and the reaction was purged with $N_2$. 1000 mL of dry THF was then added to the reaction vessel, and when all solid was dissolved, vacuum distillation was again conducted until another 1000 mL of solvent had been removed. This process of adding dry THF and solvent removal was repeated at least 4 times after which a 1 mL sample was removed for Karl Fischer analysis to determine water content. If the analysis showed that the sample contained less than 0.20% water, then reaction was continued as described in the next paragraph. However, if the analysis showed more than 0.20% water, then the drying process described above was continued until a water content of less than 0.20% was achieved.

After a water content of less than or about 0.20% was achieved using the procedure described in the previous paragraph, the distillation apparatus was replaced with a reflux condenser, and the reaction was charged with 2-amino-6-fluoro-benzonitrile (66.2 g, 470 mmol). The reaction was then heated to an internal temperature of 38-42° C. When the internal temperature had reached 38-42° C., KHMDS solution (1313 g, 1.32 mol, 20% KHMDS in THF) was added to the reaction via the addition funnel over a period of 5 minutes maintaining the internal temperature at about 38-50° C. during the addition. When addition of the potassium base was complete, the reaction was stirred for 3.5 to 4.5 hours while maintaining the internal temperature at from 38-42° C. A sample of the reaction was then removed and analyzed by HPLC. If the reaction was not complete, additional KHMDS solution was added to the flask over a period of 5 minutes and the reaction was stirred at 38-42° C. for 45-60 minutes (the amount of KHMDS solution added was determined by the following: If the IPC ratio is <3.50, then 125 mL was added; if 10.0≥IPC ratio≥3.50, then 56 mL was added; if 20.0≥IPC ratio≥10, then 30 mL was added. The IPC ratio is equal to the area corresponding to 4-amino-5-fluoro-3-[6-(4-methyl-piperazin-1-yl)-1H-benzimidazol-2-yl]-1H-quinolin-2-one) divided by the area corresponding to the uncyclized intermediate). Once the reaction was complete (IPC ratio>20), the reactor was cooled to an internal temperature of 25-30° C., and water (350 mL) was charged into the reactor over a period of 15 minutes while maintaining the internal temperature at 25-35° C. The reflux condenser was then replaced with a vacuum distillation apparatus and solvent was removed by distillation using heat as required. After 1500 mL of solvent had been removed, distillation was discontinued and the reaction was purged with $N_2$. Water (1660 mL) was then added to the reaction flask while maintaining the internal temperature at 20-30° C. The reaction mixture was then stirred at 20-30° C. for 30 minutes before cooling it to an internal temperature of 5-10° C. and then stirring for 1 hour. The resulting suspension was filtered, and the flask and filter cake were washed with water (3×650 mL). The solid thus obtained was dried to a constant weight under vacuum at 50° C. in a vacuum oven to provide 103.9 g (42.6% yield) of 4-amino-5-fluoro-3-[6-(4-methyl-piperazin-1-yl)-1H-benzimidazol-2-yl]-1H-quinolin-2-one as a yellow powder.

Procedure C

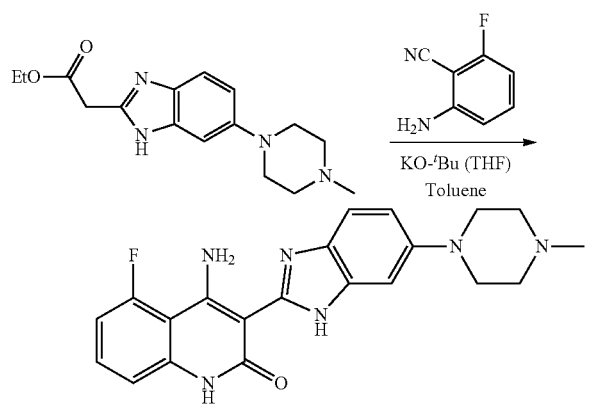

[6-(4-Methyl-piperazin-1-yl)-1H-benzimidazol-2-yl]acetic acid ethyl ester (608 g, 2.01 mol) (dried) and 2-amino-6-fluoro-benzonitrile (274 g, 2.01 mol) were charged into a 4-neck 12 L flask seated on a heating mantle and fitted with a condenser, mechanical stirrer, gas inlet, and temperature probe. The reaction vessel was purged with $N_2$, and toluene (7.7 L) was charged into the reaction mixture while it was stirred. The reaction vessel was again purged with $N_2$ and maintained under $N_2$. The internal temperature of the mixture was raised until a temperature of 63° C. (+/−3° C.) was achieved. The internal temperature of the mixture was maintained at 63° C. (+/−3° C.) while approximately 2.6 L of toluene was distilled from the flask under reduced pressure (380+/−10 torr, distilling head t=40° C. (+/−10° C.) (Karl Fischer analysis was used to check the water content in the mixture. If the water content was greater than 0.03%, then another 2.6 L of toluene was added and distillation was repeated. This process was repeated until a water content of less than 0.03% was achieved). After a water content of less than 0.03% was reached, heating was discontinued, and the reaction was cooled under $N_2$ to an internal temperature of 17-19° C. Potassium t-butoxide in THF (20% in THF; 3.39 kg, 6.04 moles potassium t-butoxide) was then added to the reaction under $N_2$ at a rate such that the internal temperature was kept below 20° C. After addition of the potassium t-butoxide was complete, the reaction was stirred at an internal temperature of less than 20° C. for 30 minutes. The temperature was then raised to 25° C., and the reaction was stirred for at least 1 hour. The temperature was then raised to 30° C., and the reaction was stirred for at least 30 minutes. The reaction was then monitored for completion using HPLC to check for consumption of the starting materials (typically in 2-3 hours, both starting materials were consumed (less than 0.5% by area % HPLC)). If the reaction was not complete after 2 hours, another 0.05 equivalents of potassium t-butoxide was added at a time, and the process was completed until HPLC showed that the reaction was complete. After the reaction was complete, 650 mL of water was added to the stirred reaction mixture. The reaction was then warmed to an internal temperature of 50° C. and the THF was distilled away (about 3 L by volume) under reduced pressure from the reaction mixture. Water (2.6 L) was then added dropwise to the reaction mixture using an addition funnel. The mixture was then cooled to room temperature and stirred for at least 1 hour. The mixture was then filtered, and the filter cake was washed with water (1.2 L), with 70% ethanol (1.2 L), and with 95% ethanol (1.2 L). The bright yellow solid was placed in a drying tray and dried in a vacuum oven at 50° C. until a constant weight was obtained providing 674 g (85.4%) of the desired 4-amino-5-fluoro-3-[6-(4-methyl-piperazin-1-yl)-1H-benzimidazol-2-yl]-1H-quinolin-2-one.

Purification of 4-Amino-5-fluoro-3-[6-(4-methyl-piperazin-1-yl)-1H-benzimidazol-2-yl]-1H-quinolin-2-one A 3000 mL 4-neck flask equipped with a condenser, temperature probe, $N_2$ gas inlet, and mechanical stirrer was placed in a heating mantle. The flask was then charged with 4-amino-5-fluoro-3-[6-(4-methyl-piperazin-1-yl)-1H-benzimidazol-2-yl]-1H-quinolin-2-one (101.0 g, 0.26 mol), and the yellow solid was suspended in 95% ethanol (1000 mL) and stirred. In some cases an 8:1 solvent ratio is use The suspension was then heated to a gentle reflux (temperature of about 76° C.) with stirring over a period of about 1 hour. The reaction was then stirred for 45-75 minutes while refluxed. At this point, the heat was removed from the flask and the suspension was allowed to cool to a temperature of 25-30° C. The suspension was then filtered, and the filter pad was washed with water (2×500 mL). The yellow solid was then placed in a drying tray and dried in a vacuum oven at 50° C. until a constant weight was obtained (typically 16 hours) to obtain 97.2 g (96.2%) of the purified product as a yellow powder.

D. Preparation of Lactic Acid Salt of 4-Amino-5-fluoro-3-[6-(4-methyl-piperazin-1-yl)-1H-benzimidazol-2-yl]-1H-quinolin-2-one, Form A

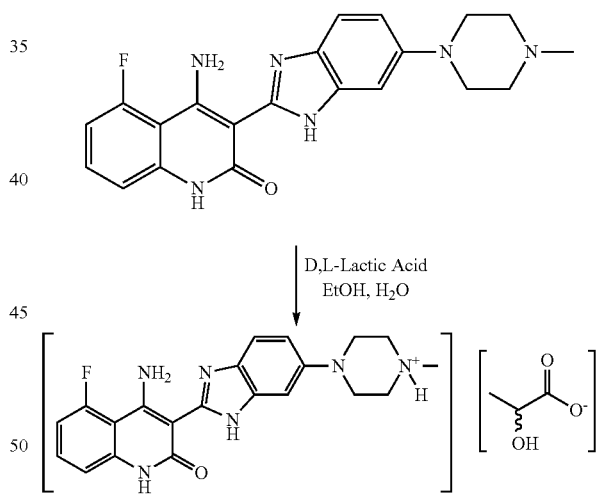

A 3000 mL 4-necked jacketed flask was fitted with a condenser, a temperature probe, a $N_2$ gas inlet, and a mechanical stirrer. The reaction vessel was purged with $N_2$ for at least 15 minutes and then charged with 4-amino-5-fluoro-3-[6-(4-methyl-piperazin-1-yl)-1H-benzimidazol-2-yl]-1H-quinolin-2-one (484 g, 1.23 mol). A solution of D,L-Lactic acid (243.3 g, 1.72 mol of monomer-see the following paragraph), water (339 mL), and ethanol (1211 mL) was prepared and then charged to the reaction flask. Stirring was initiated at a medium rate, and the reaction was heated to an internal temperature of 68-72° C. The internal temperature of the reaction was maintained at 68-72° C. for 15-45 minutes and then heating was discontinued. The resulting mixture was filtered through a 10-20 micron frit collecting the filtrate in a 12 L flask. The 12 L flask was equipped with an internal temperature probe, a reflux condenser, an addition funnel, a gas inlet an outlet, and an overhead stirrer. The filtrate was then stirred at a medium rate and heated to reflux (internal temperature of about 78° C.). While maintaining a gentle reflux, ethanol (3,596 mL) was charged to the flask over a period of about 20 minutes. The reaction flask was then cooled to an internal temperature ranging from about 64-70° C. within 15-25 minutes and this temperature was maintained for a period of about 30 minutes. The reactor was inspected for crystals. If no crystals were present, then crystals of the lactic acid salt of 4-amino-5-fluoro-3-[6-(4-methyl-piperazin-1-yl)-1H-benzimidazol-2-yl]-1H-quinolin-2-one (484 mg, 0.1 mole %) were added to the flask, and the reaction was stirred at 64-70° C. for 30 minutes before again inspecting the flask for crystals. Once crystals were present, stirring was reduced to a low rate and the reaction was stirred at 64-70° C. for an additional 90 minutes. The reaction was then cooled to about 0° C. over a period of about 2 hours, and the resulting mixture was filtered through a 25-50 micron fritted filter. The reactor was washed with ethanol (484 mL) and stirred until the internal temperature was about 0° C. The cold ethanol was used to wash the filter cake, and this procedure was repeated 2 more times. The collected solid was dried to a constant weight at 50° C. under vacuum in a vacuum oven yielding 510.7 g (85.7%) of the crystalline yellow lactic acid salt of 4-amino-5-fluoro-3-[6-(4-methyl-piperazin-1-yl)-1H-benzimidazol-2-yl]-1H-quinolin-2-one. A rubber dam or inert conditions were typically used during the filtration process. While the dry solid did not appear to be very hygroscopic, the wet filter cake tends to pick up water and become sticky. Precautions were taken to avoid prolonged exposure of the wet filter cake to the atmosphere.

Commercial lactic acid generally contains about 8-12% w/w water, and contains dimers and trimers in addition to the monomeric lactic acid. The mole ratio of lactic acid dimer to monomer is generally about 1.0:4.7. Commercial grade lactic acid may be used in the process described in the preceding paragraph as the monolactate salt preferentially precipitates from the reaction mixture.

Example 2

X-Ray Analysis of Lactic Acid Salt, Form A

Preliminary Crystallinity Studies

Preliminary XRPD (X-ray powder diffraction) analyses were carried out on a Shimadzu XRD-6000 X-ray powder diffractometer using Cu Kα radiation. The instrument is equipped with a fine focus X-ray tube. The tube voltage and amperage were set to 40 kV and 40 mA, respectively. The divergence and scattering slits were set at 1° and the receiving slit was set at 0.15 mm. Diffracted radiation was detected by a NaI scintillation detector. A theta-two theta continuous scan at 3°/minute (0.4 seconds/0.02° step) from 2.5 to 40° C. was used. 4-Amino-5-fluoro-3-[6-(4-methylpiperazin-1-yl)-1H-benzimidazol-2-yl]-1H-quinolin-2-one lactic acid salt was found to exhibit a high degree of crystallinity and have a distinct powder X-ray diffraction.

Further XRPD Characterization of 4-Amino-5-fluoro-3-[6-(4-methylpiperazin-1-yl)-1H-benzimidazol-2-yl]-1H-quinolin-2-one Lactic Acid, Form A XRPD was carried out with a Philips X'Pert powder diffractometer (Copper Kα radiation). Metallic sample holders of 0.4 or 0.8 mm depth were used (TTK type). Due to the high potency of the investigated drug substance, the sample holders were covered with a thin Kapton foil after preparation in a laminar flow bench. The wavelength of the CuKα1 radiation is 1.54060 Å. The X-ray tube was operated at a voltage of 40 kV, and a current of 40 mA. A step size of 0.02°, and a counting time of 2.0 to 2.4 s per step were applied. Due to packing density of the powder in the sample holder, the recorded intensity may be variable, and a small amorphous background resulting from the Kapton foil is difficult to distinguish from any amorphous drug substance that might be present in a sample obtained from a crystallization experiment.

The XRPD pattern of Form A is provided in FIG. 1. Relatively prominent two-theta peaks were observed at about 5.7, about 11.3, about 12.4, about 15.3, about 15.9, about 17.0, about 19.1, about 19.7, about 20.5, about 20.9, about 22.8, about 23.4, about 23.7, about 24.7, about 25.0, about 25.9, about 26.9, and about 31.2 degrees.

Example 3

Hygroscopicity of Form A

Investigation of 4-amino-5-fluoro-3-[6-(4-methylpiperazin-1-yl)-1H-benzimidazol-2-yl]-1H-quinolin-2-one lactic acid, Form A, in a DVS experiment shows that below about 80% r.h. the investigated Form A is not hygroscopic. All DVS measurements were carried out at 2.5% relative humidity change per hour. However, exposure to r.h. conditions above 90% led to a significant water uptake, which was not completely reversible during the applied measurement time. Furthermore, the water uptake was not complete when at 4500 minutes the relative humidity was scanned back from 95% to 50%. The results of the DVS measurement are shown in FIGS. 3 and 4.

The aqueous solubility of Form A in water was determined at 23° C. to be greater than 400 mg/ml (non equilibrium situation).

TABLE 1

Moisture Induced Weight Change in Lactate Salts of 4-Amino-5-fluoro-3-[6-(4-methylpiperazin-1-yl)-1H-benzimidazol-2-yl]-1H-quinolin-2-one

| Salt Form | Moisture induced % weight change | | |
|---|---|---|---|
| | 55% RH | 85% RH | 95% RH |
| Lactate-trial 1 | 0.61 | 1.39 | 12.84 |
| Lactate-trial 2 | 0.13 | 0.42 | 2.76 |
| Lactate-trial 3 | 0.08 | 0.15 | 0.24 |

Example 4

Chemical Stability

Dry powder samples of free base and Form A were maintained in open flasks under stress conditions at 30° C./60% relative humidity and 40° C./70% relative humidity. Solution samples of the free base and Form A were stored in sealed vials under ambient temperature. Samples were pulled at pre-determined time-points and analyzed for chemical stability. Samples were pulled at pre-determined time-points and assayed by HPLC with UV-visible multiple wavelength detector Two tables comparing the solid state and solution state chemical stability of the various salts are given below.

TABLE 2

Solid State Stability/HPLC Analysis of 4-amino-5-fluoro-
3-[6-(4-methylpiperazin-1-yl)-1H-benzimidazol-2-yl]-1H-
quinolin-2-one Free Base and Lactate Salts

| Salt | Area % at Time = 0 | Area % at Time = 6 weeks | Storage Condition |
|---|---|---|---|
| Free base | 97.38 | 97.83 | 30° C./60% Relative humidity |
| Lactate | 98.41 | 99.04 | 30° C./60% Relative humidity |
| Free base | 97.77 | 98.23 | 40° C./70% Relative humidity |
| Lactate | 98.46 | 98.55 | 40° C./70% Relative humidity |
| Bis-lactate | 98.99 | 97.92 | 40° C./70% Relative humidity |

TABLE 3

Solution State Stability/HPLC Analysis of Lactate
Salt of 4-Amino-5-fluoro-3-[6-(4-methylpiperazin-
1-yl)-1H-benzimidazol-2-yl]-1H-quinolin-2-one

| Salt | Area % at Time = 0 | Area % at Time = 7 days | Storage Condition |
|---|---|---|---|
| Lactate | 98.80 | 98.60 | 5° C. |
| Lactate | 98.80 | 98.71 | ambient temperature |

Example 5

Compaction Studies 200 mg of powdered 4-amino-5-fluoro-3-[6-(4-methylpiperazin-1-yl)-1H-benzimidazol-2-yl]-1H-quinolin-2-one Form A was preweighed and filled into a 0.8 cm diameter die and compressed at 5000 psi using a Carver Press (hold for 1 minute). The resulting tensile strength and thickness of the compacts were measured using a VK 200 Tablet Hardness Tester and Mitutoyo thickness gauge. When compressed the lactate salt forms strong compacts without a tendency to cap or chip.

TABLE 4

Compaction of 4-amino-5-fluoro-3-[6-(4-methylpiperazin-
1-yl)-1H-benzimidazol-2-yl]-1H-quinolin-2-one Lactate Salt

| | Compact (200 mg at 5000 psi) | | |
|---|---|---|---|
| Salt Form | Forms Compact | Thickness (mm) | Tensile strength (SC—Strong Cobb) |
| Lactate-trial 1 | Yes | 3.06 | 13.8 |
| Lactate-trial 2 | Yes | 2.92 | 17.9 |
| Lactate-trial 3 | Yes | 2.97 | 16.1 |

Example 6

Morphology of Form A

The crystal morphology of 4-amino-5-fluoro-3-[6-(4-methylpiperazin-1-yl)-1H-benzimidazol-2-yl]-1H-quinolin-2-one lactate salt was determined using a Nikon Eclipse 6600 POL polarized light microscope at 10× and 40× magnification. The lactate salt has plate shape crystal morphology which typically is preferred to needle shape crystals because of better flow properties, which positively affects formulation blending, filling, and tableting.

Example 7

DSC of Form A

Differential scanning calorimetry (DSC) was carried out on 4-amino-5-fluoro-3-[6-(4-methylpiperazin-1-yl)-1H-benzimidazol-2-yl]-1H-quinolin-2-one lactic acid, Form A, with a Perkin Elmer DSC7 (gold sample pan sealed in air). Using a heating rate of 10K/min reveals an endothermic signal of Form A near 211° C. (peak maximum), which was immediately followed by a thermal effect that possibly corresponded to the start of decomposition of the lactic acid. The observed endothermic signal was about 90 J/g, which would correspond to a typical enthalpy of fusion for a crystalline form of a drug substance. Repeating the DSC experiment at a heating rate of 20K/min resulted in a slight shift of the observed endothermic signal to 214° C. (corrected for different heating rate). This result suggested that decomposition of the lactate salt started to take place above 200° C. After reaching a temperature of 230° C. the sample was quenched to −50° C., and a second scan was performed. This second scan showed two small steps both corresponding to $\Delta C_p$ of about 0.1 J/gK. The first step was found near 2° C., and the second step was found to be at about 94° C. and shows a rather strong relaxation peak. While the first step was attributed to decomposition products formed during the first scan, the second step might correspond to the glass transition of the amorphous form which is described in Example 9. A representative DSC thermogram is shown in FIG. 2.

Example 8

The Amorphous Form of 4-Amino-5-fluoro-3-[6-(4-methylpiperazin-1-yl)-1H-benzimidazol-2-yl]-1H-quinolin-2-one Lactic Acid The amorphous form of 4-amino-5-fluoro-3-[6-(4-methylpiperazin-1-yl)-1H-benzimidazol-2-yl]-1H-quinolin-2-one lactic acid salt, was produced by lyophilization of an aqueous solution as follows: 580 mg of Form A were dissolved in 5.0 ml of water. The solution was filtered through a 0.22 μm Millipore filtration unit, and transferred into a 100 ml round-bottomed glass flask at 23±2° C. In order to avoid contamination of the lyophilizer a G2 glass filter was placed between lyophilization unit and sample flask. The clear solution was frozen in a bed of dry ice (solid $CO_2$) at −78° C., and subsequently the glass flask with the frozen solution was connected to a lyophilizer. Lyophilizer type: CHRIST, BETA 2-8 LD-2. The initial pressure of was 0.04 mbar, and the cold trap temperature was −90° C. After about 17.5 hours, the lyophilization was found to be complete and the flask was disconnected. The obtained yellow solid powder was characterized by powder X-ray diffraction, Raman spectroscopy, and $^1$H-NMR. XRPD was carried out to determine the XRPD patterns of the amorphous form in a similar fashion as described for Form A in Example 2. The XRPD measurement of the amorphous form shown in FIG. 5 demonstrates that the yellow solid powder is essentially amorphous (i.e., no prominent peaks); however, at least three small peaks (two-theta peaks are at about 3.6°, about 25.0°, and about 28.6°) indicate that crystallization into a crystalline form, different from Form A, might be starting to take place. Nevertheless, the amorphous form is stable under ambient conditions. It was further determined to be stable at 75% relative humidity and at 40° C. for more than 2 days.

Example 9

DSC of the Amorphous Form

Differential scanning calorimetry (DSC) was carried out on 4-amino-5-fluoro-3-[6-(4-methylpiperazin-1-yl)-1H-benzimidazol-2-yl]-1H-quinolin-2-one lactic acid, the amorphous form, with a Perkin Elmer DSC7 (gold sample pan sealed in air). A heating rate of 20K/min revealed an endothermic signal of the amorphous form near 87° C. (peak maximum), which corresponded to the glass transition of the amorphous form. Subsequent exothermic events between 110° C. and 150° C. (major exotherm at about 132° C.) followed by an endothermic signal (at about 179° C.), which might be attributed to the existence of a melting point somewhere near 180° C. (ΔH~43 J/g, under decomposition) suggested a recrystallization into a new form. The endothermic signal was again followed by an exothermic event (at about 185° C.) which could be attributed to a phase transformation (ΔH~−7 J/g) and a further endothermic signal (at about 201° C.) which possibly corresponded to Form A.

Example 10

Hydrate of Lactic Acid Salt of 4-Amino-5-fluoro-3-[6-(4-methyl-piperazin-1-yl)-1H-benzimidazol-2-yl]-1H-quinolin-2-one, Form B A. Preparation of Form B Form B was obtained by all of the following procedures.

Form A (202 mg) was suspended in 2.0 ml ethanol-water (9/1, v/v) at R.T. for 42 hours with stirring. The suspension was filtered and solid obtained was dried in air at room temperature. The final solid was characterized by X-ray and/or DSC as Form B.

From A (115 mg) was suspended in 2.0 ml MEK—water (9/1, v/v) at R.T. for 21 hours with stirring. The suspension was filtered and solid obtained was dried in air at room temperature. The final solid was characterized by X-ray and/or DSC as Form B.

From A (250 mg) was suspended in 2.1 ml acetonitrile—water (20/1, v/v) at 50° C. for about 24 hours with stirring. The suspension was filtered and solid obtained was dried in air at room temperature. The final solid was characterized by X-ray and/or DSC as Form B.

B. X-Ray Analysis of Form B

XRPD was carried out to determine the XRPD patterns of Form B in a similar fashion as described for Form A in Example 2. One example of the XRPD pattern of Form B is provided in FIG. 6. Relatively prominent two-theta peaks were at about 10.2, about 11.3, about 11.6, about 11.9, about 12.9, about 15.3, about 15.6, about 16.1, about 17.6, about 18.5, about 19.3, about 22.3, about 23.3, about 23.5, about 23.9, about 26.0, about 28.2, about 29.3, about 29.8, about 30.7, about 32.2, about 32.6, about 33.1 and about 34.3°.

C. Analysis of Hydrate Water Content in Form B

TG-FTIR analysis of Form B samples revealed a weight loss of about 3.7%. At a heating rate of 10 K/min the weight loss started just above ambient temperature and the 3.7% of water were completely removed near 150° C. Further analysis of the water content by Karl Fischer titration (also determined to be about 3.7%) confirmed that the weight loss in the TG-FTIR likely corresponded to the water content. Although not wishing to be bound by any particular theory, Form B is characterized as a monohydrate, since the theoretically expected water content of a monohydrate of the mono-lactic acid salt of the compound of formula I is 3.7%. The TG-FTIR analysis was carried out with a Netzsch Thermo-Microbalance TG 209 coupled to a Bruker FTIR Spectrometer Vector 22 (sample pans with a pinhole, $N_2$ atmosphere, heating rate 10 K/min). The same instruments were used in all the examples described herein when TG-FTIR analysis was carried out.

D. DSC of Form B

Differential scanning calorimetry (DSC) was carried out on Form B samples, with a Perkin Elmer DSC7 (gold sample pan sealed in air). Using a heating rate of 20° C./min reveals an endothermic signal of Form B near 155° C. (peak maximum) with a ΔH~100 J/g. No other apparent phase transitions are found below 200° C.

E. Hygroscopicity of Form B

DVS showed that Form B does not readily adsorb additional water to form a higher hydrate, but the (hydrate)-water was completely removed under nitrogen (0% r.h.) within a few hours at room temperature. Scanning the relative humidity back to 50% showed that the previously lost water was readsorbed when a relative humidity of about 20 to 30% was reached.

Although not wishing to be bound by any particular theory, the behavior of Form B in the DVS investigation reflects the properties of a typical channel hydrate. In order to substantiate this thesis the following experiment was carried out: 1) Form B was stored under dry nitrogen for about 1 day and XRPD of the dried sample was measured under dry nitrogen. The found XRPD pattern matched the XRPD pattern of the initially prepared Form B. 2) After the XRPD measurement, the dried sample of Form B was exposed to a relative humidity of 53% for about 4 days and a XRPD pattern was recorded under ambient conditions. Again, the XRPD pattern corresponded to Form B. 3) Karl Fischer titration of the humidified sample showed a water content of 3.7%, which corresponds to the monohydrate.

Example 11

Hydrate of Lactic Acid Salt of 4-Amino-5-fluoro-3-[6-(4-methyl-piperazin-1-yl)-1H-benzimidazol-2-yl]-1H-quinolin-2-one, Form C A. Preparation of Form C Form C was obtained by all of the following procedures. To a concentrated solution of 4-amino-5-fluoro-3-[6-(4-methylpiperazin-1-yl)-1H-benzimidazol-2-yl]-1H-quinolin-2-one lactic acid salt in water, was diffused of acetonitrile vapor at 5° C. Additional acetonitrile was added to the resulting slurry. The mixture was filtered and the solid obtained was dried in air at room temperature. The final solid was characterized by XRPD and/or DSC as Form C.

The amorphous faun (about 200 mg) was placed under 75% r.h. (relative humidity) at 40° C. for about 4 days. The resulting solid was characterized by XRPD and/or DSC as Form C. Although not wishing to be bound to any particular theory, it is postulated that under such conditions the amorphous form crystallizes into Form H (a transient mesomorphic form described in Example 18 herein after), which then transforms into Form C.

B. X-Ray Analysis of Form C

XRPD was carried out to determine the XRPD patterns of Form C in a similar fashion as described for Form A in Example 2. One example of the XRPD pattern of Form C is provided in FIG. 11. Relatively prominent two-theta peaks were at from about 3.2 to about 3.6, at from about 6.5 to about 7.1, at from about 9.8 to about 10.6, at from about 13.3 to about 14.1, at from about 17.6 to about 17.8, at about 18.8, at about 20.2, at from about 24.7 to about 24.9, at about 27.3 to about 27.5, at about 28.0, and at from about 29.0 to about 29.3°.

Small variation was noted for the XRPD patterns of Form C, suggesting that Form C can adsorb variable amounts of water. A higher water content is likely to lead to a slight lattice expansion (larger d-spacings) with a concurrent shift of the XRPD peaks to smaller angles. For example, in a separate XRPD for Form C, the three peaks at the low 2θ values are located at 2θ=3.25, 6.5, and 9.75°. Presumed that these peaks can be indexed as 1/0/0, 2/0/0, and 3/0/0, it is readily conceivable that a lattice expansion and contraction occurs in one dimension as the water content changes.

C. Analysis of Hydrate Water Content in Form C

TG-FTIR analysis of Form C samples revealed a weight loss of about 4.6%, which corresponds to an amount that lies between the mono- and the sesquihydrate. At a heating rate of 10 K/min the weight loss started just above ambient temperature and the 4.6% of water were completely removed near 150° C.

D. DSC of Form C

Differential scanning calorimetry (DSC) was carried out on Form C samples, with a Perkin Elmer DSC7 (gold sample pan sealed in air) using a heating rate of 20° C./min. The DSC investigation of Form C showed a very small exothermic signal between about 48° C. and 80° C., this exothermic signal was attributed to crystallization of a small amount of residual amorphous form. Between about 78 and 138° C. several small endothermic signals (at about 109° C., about 115° C., and about 127° C.) and one small exothermic signal (at about 123° C.) suggested that multiple phase transitions are taking place. These effects were followed by a strong endothermic signal (ΔH=35 J/g) with a peak near 150° C.

E. Hygroscopicity of Form C

Investigation of one sample of Form C in a DVS experiment revealed a water content of about 6.5% at the start of the measurement and about 4.8% at the end of the measurement. While the apparent irreversibility of the water sorption was noted, the Raman spectrum of the recovered sample still corresponded essentially to Form C. Although not wishing to be bound by any particular theory, the reason for the irreversibility found for Form C may be due to some remaining amorphous material that is crystallizing during the measurement. If this thesis is correct, then the true water content of Form C would be about 4.6%, as found for the sample used in the DSC experiment as shown herein above. This amount of water would correspond to 4/3 water molecules per formula unit. The fact that Form C can adsorb more than 15% of water may mean that either a reversible phase transition into a higher hydrate takes place, or that Form C consists of a structure with larger channel that can accommodate such high amounts of water.

Example 12

Hydrate of Lactic Acid Salt of 4-Amino-5-fluoro-3-[6-(4-methyl-piperazin-1-yl)-1H-benzimidazol-2-yl]-1H-quinolin-2-one, Form D A. Preparation of Form D Form D was obtained by the following procedure. The amorphous form (about 100 mg) was placed under nitrogen at 120° C. for about 5 hours. The resulting solid was characterized by XRPD and/or DSC as Form D.

B. X-Ray Analysis of Form D

XRPD was carried out to determine the XRPD patterns of Form D in a similar fashion as described for Form A in Example 2. One example of the XRPD pattern of Form D is provided in FIG. 8. Relatively prominent two-theta peaks were at about 4.0, about 8.0, about 11.5, about 12.0, about 14.3, about 15.8, about 16.4, about 20.1, about 21.2, about 22.0, about 23.6, about 27.2 and about 27.9 degrees.

C. Analysis of Hydrate Water Content in Form D

When a freshly prepared sample of Form D was analyzed by TG-FTIR a weight loss of about 2% with a clear step in the temperature range between 70° C. and about 110° C. was found. This weight loss was attributed to water. However, a subsequent water analysis by Karl Fischer titration showed a water content of 3.4% which suggested a monohydrate rather than a hemihydrate. It is likely that the additional water uptake occurred between the two analysis. Since samples of the amorphous form obtained from lyophilizations are generally hygroscopic, it is conceivable that water adsorbed by the amorphous form is the reason that a hydrate was formed even under exclusion of atmospheric moisture. The discrepancy between the TG result and the water analysis by Karl Fischer titration may also be an indication that a very hygroscopic anhydrate was initially obtained.

D. DSC of Form D

Differential scanning calorimetry (DSC) was carried out on Form D samples, with a Perkin Elmer DSC7 (gold sample pan sealed in air) using a heating rate of 20° C./min. The DSC investigation of Form D revealed multiple transitions with an endothermic signal near 75° C. (ΔH~13 J/g), followed by a second endothermic signal near 147° C. (ΔH~27 J/g) and an exothermic signal near 163° C., and a further endothermic signal near 191° C. (ΔH~31 J/g).

E. Hygroscopicity of Form D

Dynamic vapor sorption of a sample of Form D showed an additional water uptake from 3.6% to about 9% when the humidity was raised to 90%, and the (hydrate)-water was completely released when r.h. was scanned to 0% and kept there for 12 hours. However, scanning from 0 to 50% r.h. resulted in a water uptake of about 4.3%, which was near the value found at the end of the measurement of Form C.

The DVS investigation of Form D is consistent with the result from the Karl Fischer titration (hydrate-water content suggests a monohydrate rather than a hemihydrate, in Example 12.C hereinabove); however, the sample recovered at the end of the DVS measurement again showed a Raman spectrum that still substantially corresponded to Form D with slightly variance. It is expected that such a sample would also show a slight variation in XRPD pattern.

Example 13

Hydrate of Lactic Acid Salt of 4-Amino-5-fluoro-3-[6-(4-methyl-piperazin-1-yl)-1H-benzimidazol-2-yl]-1H-quinolin-2-one, Form E A. Preparation of Form E Form E was obtained by all of the following procedures.

Form A (390 mg) was suspended in 2.0 ml of water at room temperature (R.T.) for about 24 hours with stirring. Sample number one was taken from the slurry. After about 48 hours, the suspension was filtered and solid obtained was dried in air at room temperature. Both the sample number one and the final solid was characterized by XRPD and/or DSC as Form E.

From A (400 mg) was dissolved in 2.0 ml water and the solution was seeded with 80 mg of Form E. Suspension was stirred for 3 days at 23° C. The resulting suspension was filtered and the solid obtained characterized by XRPD and/or DSC as Form E.

From A (460 mg) was dissolved in 2.0 ml water and the solution was seeded with 20 mg of Form E. The suspension was stirred for 3 days at 23° C. and a thick paste was obtained. The resulting paste was diluted with 1.0 ml water, and slightly warmed up. A solution was obtained. The solution was seeded again with about 10 mg of Form E and the resulting suspension stirred for about 66 hours at 23° C. The resulting suspension was filtered and the solid obtained characterized by XRPD and/or DSC as Form E.

A solution of the amorphous form (328 mg) in 1.0 ml was added to 5.0 ml THF. Subsequently, ethyl acetate (10 ml) was added to the resulting mixture at 2° C. The resulting suspension was stirred for about 24 hours at 2° C., then filtered. The solid obtained was dried in air at R.T. and was characterized by XRPD and/or DSC as Form E.

Form A (189 mg) was dissolved in 12 ml of THF and 1.0 ml THF-water (1:1, v/v, further containing 2% lactic acid) at an elevated temperature near the boiling temperature of the solution. The solution was cooled to 1° C. and precipitation occurred after about 2 hours. Stirring of the mixture continued at 1° C. for about 2 hours, then filtered. The solid obtained was dried in air at R.T. and was characterized by XRPD and/or DSC as Form E.

The amorphous form (210 mg) was suspended in a mixture of 2.0 ml acetonitrile with 0.1 ml water, at 5° C. for about 5 days with stirring. Then the suspension was filtered and solid obtained was dried in air at room temperature. The final solid was characterized by XRPD and/or DSC as Form E.

The $^1$H-NMR analysis of Form E samples confirmed the chemical integrity of the lactate salt of the compound of formula I in Form E.

B. X-Ray Analysis of Form E

XRPD was carried out to determine the XRPD patterns of Form E in a similar fashion as described for Form A in Example 2. One example of the XRPD pattern of Form E is provided in FIG. 9. Relatively prominent two-theta peaks were at about 6.1, about 8.4, about 8.7, about 12.1, about 13.4, about 14.9, about 18.1, about 19.0, about 20.1, about 21.1 about 21.5, about 22.6, about 24.1, about 24.5, about 25.0, about 25.5, about 27.7, about 30.1, and about 30.6 degrees.

C. Analysis of Hydrate Water Content in Form E

TG analysis of Form E samples revealed a weight loss of from about 9% to about 18%. At a heating rate of 10 K/min the weight loss started just above ambient temperature and all the water is completely removed near 160° C. Samples containing 18% weight loss (corresponding to hydrate water loss) suggests that Form E is a hexahydrate D. DSC of Form E Differential scanning calorimetry (DSC) was carried out on Form E samples, with a Perkin Elmer DSC7 (gold sample pan sealed in air) using a heating rate of 20° C./min.

DSC of Form E revealed multiple transitions: The most prominent peak corresponded to an endothermic signal near 78° C. (ΔH~71 J/g), which was followed by a very small endothermic and a very small exothermic signal at about 90° C. and about 93° C., respectively), and a stronger endothermic signal near 130° C. (ΔH~36 J/g).

E. Hygroscopicity of Form E

Investigation of one sample of Form E in a DVS experiment reveals that Form E absorbs about one additional percent of water when the relative humidity was increased to 90%. A water content of 18% at 90% r.h. would suggest the existence of a hexahydrate at high relative humidity. When r.h. was scanned to 0% and kept at this condition for a few hours substantially all the hydrate water was desorbed. However, when scanning back to 50% r.h. the water uptake within the investigated time scale was only about 6%. Such an irreversibility suggests a phase transformation. Although not wishing to be bound by any particular theory, it is postulated that Form E, upon dehydration, is likely to become the amorphous form. However, the amorphous form is unstable under humid conditions and at a high temperature, and likely to crystallizes into Form I (the mesomorphic form, described in Example 17 herein after) or other forms, and eventually into forms C or D.

F. Aqueous solubility of Form E

The aqueous solubility of Form E in water was determined at 23° C. to 68±10 mg/ml.

Example 14

1,4-Dioxane Hemi-Solvate of Lactic Acid Salt of 4-Amino-5-fluoro-3-[6-(4-methyl-piperazin-1-yl)-1H-benzimidazol-2-yl]-1H-quinolin-2-one, Form F A. Preparation of Form F Form A (about 100 mg) was suspended in 3.0 ml of a mixture of 1,4-dioxane and methyl t-butyl ether (i.e., MTBE) (3.0 ml; 1/1, v/v). The suspension was stirred at 5° C. for about 18 hours and then was filtered. The solid obtained was dried in air at R.T. and was characterized by XRPD as Form F.

The $^1$H-NMR analysis of Form F samples confirmed the chemical integrity of the lactate salt of the compound of formula I in Form F.

B. X-Ray Analysis of Form F

XRPD was carried out to determine the XRPD patterns of Form F in a similar fashion as described for Form A in Example 2. One example of the XRPD pattern of Form F is provided in FIG. 10. Relatively prominent two-theta peaks were at about 5.2, about 5.7, about 10.4, about 11.7, about 12.4, about 13.6, about 15.2, about 15.6, about 16.0, about 17.0, about 18.6, about 18.9, about 19.7, about 21.2, about 21.8, about 22.2, about 23.3, about 24.1, about 25.0, about 26.0, about 26.8, about 27.4, about 28.8, about 31.2, and about 31.7 degrees.

C. Analysis of 1,4-Dioxane Content in Form F

TG-FTIR analysis of Form F samples showed a weight loss of about 7.2% which was attributed to release of 1,4-dioxane. Release of the dioxane was found to occur mainly between about 50° C. and 160° C. After the release of the dioxane, the $^1$H-NMR analysis of the resultant sample confirmed the chemical integrity of the lactate salt of the compound of Formula I. Since the theoretical 1,4-dioxane content of a hemisolvate is expected to be 8.4%, it is postulated that Form F is a 1,4-dioxane hemisolvate.

Example 15

Benzene Hemi-Solvate of Lactic Acid Salt of 4-Amino-5-fluoro-3-[6-(4-methyl-piperazin-1-yl)-1H-benzimidazol-2-yl]-1H-quinolin-2-one, Form G A. Preparation of Form G Form A (about 206 mg) was suspended in 2.0 ml of benzene. The suspension was stirred at room temperature for about 3 days and then was filtered. The solid obtained was dried in air at R.T. for about 20 minutes and was characterized by XRPD as Form G.

The $^1$H-NMR analysis of Form G samples confirmed the chemical integrity of the lactate salt of the compound of formula I in Form G.

B. X-Ray Analysis of Form G

XRPD was carried out to determine the XRPD patterns of Form G in a similar fashion as described for Form A in Example 2. One example of the XRPD pattern of Form G is provided in FIG. 11. Relatively prominent two-theta peaks were at about 5.4, about 10.3, about 11.5, about 12.3, about 13.5, about 15.2, about 16.2, about 17.1, about 18.4, about 18.6, about 19.3, about 20.5, about 21.5, about 22.9, about 23.8, about 24.7, about 25.9, about 26.3, about 26.8, about 27.3, about 28.9, about 31.2, and about 32.7 degrees.

C. Analysis of 1,4-Dioxane Content in Form G

TG-FTIR analysis of Form G samples revealed a weight loss of about 7.4% in the temperature range from about 140° C. to 180° C., all essentially attributed to release of benzene. Since the theoretical benzene content for a hemisolvate is expected to be 7.5%, it is postulated that Form G is a benzene hemisolvate.

Example 16

Mesomorphic Form of Lactic Acid Salt of 4-Amino-5-fluoro-3-[6-(4-methyl-piperazin-1-yl)-1H-benzimidazol-2-yl]-1H-quinolin-2-one, Form H A. Preparation of Form H A solution of the amorphous form (328 mg) in 1.0 ml was added to 10.0 ml of acetonitrile at 2° C. The resulting suspension was stirred for about 24 hours at 2° C., then filtered. The solid obtained was dried in air at R.T. and was characterized by XRPD as Form H.

An evaporation experiment was carried out at ambient temperature, i.e., in a climatized laboratory at 23±2° C. Evaporation under a fast $N_2$ flow was performed at a flow rate of approximately 0.4 liters/min and evaporation under a slow $N_2$ flow was performed at a flow rate of approximately 0.03 liters/min through the channel system as described in WO 03/026797 A2. The duration of the evaporation experiment was about 67 hours, and the suspensions were equilibrated for about 68 hours. An evaporation experiment with 200 mg of Form A in 3.0 ml water gave Form H which was subsequently characterized and confirmed by XRPD.

B. X-Ray Analysis of Form H

XRPD was carried out to determine the XRPD patterns of Form H in a similar fashion as described for Form A in Example 2. One example of the XRPD pattern of Form F is provided in FIG. 12. Relatively prominent two-theta peaks were observed at about 3.5, about 6.9, about 10.3, about 16.9, about 20.6, and about 26.8 degrees.

Example 17

Intermediate State of Hydrate of Lactic Acid Salt of 4-Amino-5-fluoro-3-[6-(4-methyl-piperazin-1-yl)-1H-benzimidazol-2-yl]-1H-quinolin-2-one, Form I A. Preparation of Form I Form A (482 mg) was dissolved in 800 μl of water, and the appearance of the mixture was followed over time. The initial solution turned into a thick and highly viscous paste after about 6 hours. 0.5 ml of water was added to the paste, and again a solution was obtained. However, within 3 days, this solution again turned in to a thick and highly viscous paste, which was not suitable for filtration. The aqueous paste was measured by XRPD and determined to be Form I. $^1$H-NMR analysis of Form I samples confirmed integrity of the lactate salt. Karl Fischer titration of Form I sample indicates water content of about 20%.

B. X-Ray Analysis of Form I

XRPD was carried out to determine the XRPD patterns of Form I (as a wet semi solid) in a similar fashion as described for Form A in Example 2. One example of the XRPD pattern of Form I is provided in FIG. 13. Relatively prominent two-theta peaks were at about 2.3, about 4.0, about 4.6, about 6.0, about 8.1, about 9.0, about 9.8, about 10.3, about 11.9, about 12.5, about 13.4, about 13.6, about 14.0, about 15.7, about 16.2, about 17.0, about 17.6, about 17.8, about 19.2, about 20.0, about 20.6, about 21.5, about 22.2, about 23.7, about 24.1, about 25.1, about 25.5, about 26.5, and about 30.0 degrees.

C. Aqueous Solubility of Form I

The aqueous solubility of Form I in water was determined at 23° C. to 127±10 mg/ml (equilibrium after at least 3 day at R.T.).

Various modifications of the invention, in addition to those described herein, will be apparent to those skilled in the art from the foregoing description. Such modifications are also intended to fall within the scope of the appended claims. Each reference, including all patents, patent applications, and journal literature, cited in the present application is incorporated herein by reference in its entirety.

What is claimed is:

1. Crystalline hydrate Form B of a lactic acid salt of a compound of Formula I or a tautomer thereof:

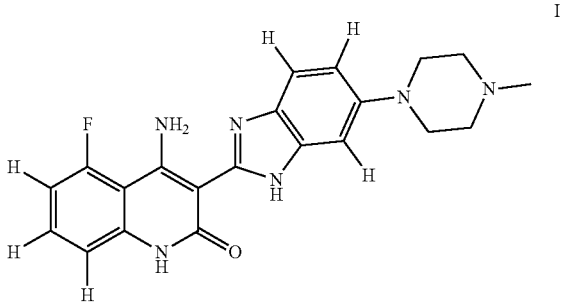 [SMILES: CN1CCN(c2ccc3nc(-c4c(N)c5c(F)cccc5[nH]c4=O)[nH]c3c2)CC1]

having
an X-ray powder diffraction pattern comprising characteristic peaks, in terms of 2θ at substantially 10.2, substantially 11.3, substantially 11.6, substantially 11.9, substantially 12.9, substantially 15.3, substantially 15.6, substantially 16.1, substantially 17.6, substantially 18.5, substantially 19.3, substantially 22.3, substantially 23.3, substantially 23.5, substantially 23.9, substantially 26.0, substantially 28.2, substantially 29.3, substantially 29.8, substantially 30.7, substantially 32.2, substantially 32.6, substantially 33.1 and substantially 34.3 degrees.

2. The crystalline form of claim 1, which is a mono-lactic acid.

3. The crystalline form of claim 1, having a differential scanning calorimetry thermogram comprising an endotherm at about 155° C.

4. A composition comprising the crystalline form of claim 1.

5. A composition comprising at least 50% by weight of the crystalline form of claim 1.

6. A composition comprising at least 70% by weight of the crystalline form of claim 1.

7. A composition comprising at least 80% by weight of the crystalline form of claim 1.

8. A composition comprising at least 90% by weight of the crystalline form of claim 1.

9. A composition composing at least 95% by weight of the crystalline form of claim 1.

10. A composition comprising at least 99% by weight of the crystalline form of claim 1.

11. The composition of claim 4, further comprising a pharmaceutically acceptable carrier.

12. A solid formulation for oral administration comprising the crystalline hydrate form of claim 1.

13. The formulation of claim 12 in the form of a powder.

14. The formulation of claim 12 wherein said crystalline form remains substantially intact under ambient conditions for a period greater than about 38 hours.

15. The formulation of claim 12 wherein said crystalline hydrate form remains substantially intact under ambient conditions for a period greater than about 1 week.

16. The formation of claim 12 wherein said crystalline hydrate form remains substantially intact under ambient conditions for a period greater than about 1 month.

17. The formulation of claim 12 wherein said crystalline hydrate form remains substantially intact under ambient conditions for a period greater than about 6 months.

18. The formulation of claim 12 wherein said crystalline hydrate form remains substantially intact under ambient conditions for a period greater than about 1 year.

19. A dosage form comprising a formulation according to claim 12.

20. The dosage form of claim 19, wherein said dosage form is a powder, pill, tablet, capsule, caplet pellets, or granules.

21. A method of treating cancer in a patient, which comprises administering to the patient an effective amount of the crystalline hydrate form of claim 1.

22. The method of claim 21, wherein the cancer is selected from multiple myeloma (MM), acute myelogenous leukemia (AML), prostate cancer, breast cancer, colon cancer, or melanoma.

23. The method of claim 21, wherein said patent a refractory patent.

24. The method of claim 21, wherein the crystalline form is prepared with a unit dose comprising 0.25 to 30 mg/kg of the lactic acid salt of the compound of formula I or a tautomer thereof.

25. A method for preparing the crystalline hydrate form of claim 1, comprising suspending Form A in a solution comprising water and an organic solvent at a temperature of about 20° C. to about 60° C., wherein said water is present in said solution in an amount of about 5% to about 20% by volume, wherein Form A is a crystalline form of lactic acid salt of the compound of Formula I or a tautomer thereof, having an X-ray powder diffraction pattern comprising characteristic peaks, in terms of 2θ at about 5.7, about 11.3, about 12.4, about 15.3, about 15.9, about 17.0, about 19.1, about 19.7, about 20.5, about 20.9, about 22.8, about 23.4, about 23.7, about 24.7, about 25.0, about 25.9, about 26.9, and about 31.2 degrees.

26. The method of claim 21, wherein said organic solvent comprises an alcohol, a ketone, an organic nitrile, or mixture thereof.

27. The method of claim 21, wherein said organic solvent comprises one or more of ethanol, acetone, methyl ethyl ketone, acetonitrile.

* * * * *